United States Patent
Haga et al.

(10) Patent No.: US 10,835,572 B2
(45) Date of Patent: Nov. 17, 2020

(54) COMPOSITION FOR EXTERNAL APPLICATION

(71) Applicant: ROHTO PHARMACEUTICAL CO., LTD., Osaka (JP)

(72) Inventors: Masatoshi Haga, Osaka (JP); Keiko Oyamada, Osaka (JP); Rumi Matsushita, Osaka (JP); Yuya Hayashi, Osaka (JP); Kyoko Nakajima, Osaka (JP); Yuko Kouda, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 219 days.

(21) Appl. No.: 15/322,779

(22) PCT Filed: Jun. 30, 2015

(86) PCT No.: PCT/JP2015/068804
§ 371 (c)(1),
(2) Date: Mar. 29, 2017

(87) PCT Pub. No.: WO2016/002767
PCT Pub. Date: Jan. 7, 2016

(65) Prior Publication Data
US 2017/0209522 A1    Jul. 27, 2017

(30) Foreign Application Priority Data

Jun. 30, 2014  (JP) ................. 2014-134940
Jun. 30, 2014  (JP) ................. 2014-134941
(Continued)

(51) Int. Cl.
*A61K 8/44*    (2006.01)
*A61K 38/05*   (2006.01)
(Continued)

(52) U.S. Cl.
CPC .......... *A61K 38/05* (2013.01); *A61K 8/34* (2013.01); *A61K 8/44* (2013.01); *A61K 8/4946* (2013.01);
(Continued)

(58) Field of Classification Search
CPC ........................................................ A61K 8/44
See application file for complete search history.

(56) References Cited

U.S. PATENT DOCUMENTS 4,640,943 A * 2/1987 Meguro ................. A61K 8/19
                                                106/414
5,503,776 A   4/1996 Murase et al.
(Continued)

FOREIGN PATENT DOCUMENTS

EP   0500332 A2   8/1992
EP   1297830 A1   4/2003
(Continued)

OTHER PUBLICATIONS

Yasutomo Nishimori, "Photoaging and wrinkles, Correlative changes of dermal collagen fiber bundles and wrinkles.", Fragrance Journal, 4, pp. 36-37, 1998 (English translation: abstract only).
(Continued)

*Primary Examiner* — Benjamin J Packard
(74) *Attorney, Agent, or Firm* — Riverside Law LLP

(57) ABSTRACT

An object of the present invention is to provide an external use composition having a novel composition that has a superior effect promoting collagen production and is able to suppress, prevent or improve wrinkles and sagging of the skin with aging.
The present invention relates to an external use composition for anti-aging, comprising (A) a lipopeptide represented by the following formula (1), or a pharmaceutically acceptable salt thereof:

(Continued)

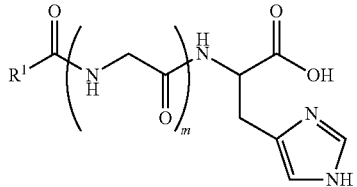

(1)

(wherein, $R^1$ represents a saturated aliphatic group, or aliphatic group having a single unsaturated bond, having 9 to 19 carbon atoms, and m represents 0 or 1).

18 Claims, 13 Drawing Sheets

(30) Foreign Application Priority Data

Jun. 30, 2014 (JP) .................. 2014-134942
Jun. 30, 2014 (JP) .................. 2014-134943

(51) Int. Cl.

| | | |
|---|---|---|
| A61K 9/08 | (2006.01) | |
| A61K 31/7034 | (2006.01) | |
| A61Q 17/04 | (2006.01) | |
| A61K 31/506 | (2006.01) | |
| A61K 8/49 | (2006.01) | |
| A61K 31/122 | (2006.01) | |
| A61K 31/12 | (2006.01) | |
| A61K 8/64 | (2006.01) | |
| A61K 8/34 | (2006.01) | |
| A61K 8/67 | (2006.01) | |
| A61K 9/00 | (2006.01) | |
| A61K 31/045 | (2006.01) | |
| A61K 31/375 | (2006.01) | |
| A61K 45/06 | (2006.01) | |
| A61K 47/10 | (2017.01) | |
| A61Q 11/00 | (2006.01) | |
| A61Q 15/00 | (2006.01) | |
| A61Q 19/08 | (2006.01) | |

(52) U.S. Cl.
CPC .............. *A61K 8/64* (2013.01); *A61K 8/676* (2013.01); *A61K 9/0014* (2013.01); *A61K 9/0048* (2013.01); *A61K 9/08* (2013.01); *A61K 31/045* (2013.01); *A61K 31/12* (2013.01); *A61K 31/122* (2013.01); *A61K 31/375* (2013.01); *A61K 31/506* (2013.01); *A61K 31/7034* (2013.01); *A61K 45/06* (2013.01); *A61K 47/10* (2013.01); *A61Q 11/00* (2013.01); *A61Q 15/00* (2013.01); *A61Q 17/04* (2013.01); *A61Q 19/08* (2013.01)

(56) References Cited

U.S. PATENT DOCUMENTS

| | | | |
|---|---|---|---|
| 5,785,978 A | | 7/1998 | Porter et al. |
| 6,312,450 B1 * | | 11/2001 | Yavitz .............. A61B 18/203 |
| | | | 424/400 |
| 2004/0132667 A1 | | 7/2004 | Lintner |
| 2006/0172059 A1 | | 8/2006 | Takeuchi |
| 2011/0183913 A1 | | 7/2011 | Miyamoto et al. |
| 2012/0258059 A1* | | 10/2012 | Iwama .............. A61K 8/64 |
| | | | 424/59 |
| 2013/0084305 A1 | | 4/2013 | Iwama et al. |
| 2013/0267610 A1 | | 10/2013 | Miyamoto |
| 2014/0303080 A1 | | 10/2014 | Yu et al. |
| 2015/0080291 A1 | | 3/2015 | Zhang et al. |

FOREIGN PATENT DOCUMENTS

| | | | |
|---|---|---|---|
| EP | 2180027 A1 | 4/2010 | |
| EP | 2692335 A1 | 2/2014 | |
| JP | H05-065275 A | 3/1993 | |
| JP | H-07194375 A | 8/1995 | |
| JP | H10-508856 A | 9/1998 | |
| JP | 2000309521 A | 11/2000 | |
| JP | 2001206835 A | 7/2001 | |
| JP | 2005239645 A | 9/2005 | |
| JP | 2005263794 A | 9/2005 | |
| JP | 2007515381 A | 6/2007 | |
| JP | 2008001661 A | 1/2008 | |
| JP | 2009179599 A | 8/2009 | |
| JP | 2011-057620 A | 3/2011 | |
| JP | 2015051961 A | 3/2015 | |
| WO | 2004056216 A1 | 7/2004 | |
| WO | 2010013555 A1 | 2/2010 | |
| WO | 2011052613 A1 | 5/2011 | |
| WO | 2012096276 A1 | 7/2012 | |
| WO | 2012128438 A1 | 9/2012 | |
| WO | 2013063615 A2 | 5/2013 | |
| WO | 2013142088 A1 | 9/2013 | |

OTHER PUBLICATIONS

Takeo Mitsui edition, New Cosmetology, 2nd edition, Nanzan dou, 2001, pp. 42-50 and its partial English translation.
Lever, Kumar and Marks, "Topical retinoic acid for treatment of solar damage", British Journal of Dermatology, 122, pp. 91-98, 1990.
Miyachi et al. "Research & Development for Cosmetics, Toiletries & Allied Industries", Fragrance Journal, pp. 54-60 and 127 with cover page, 2014. (English translation: abstract only).
English translation of IPRP issued on Jan. 12, 2017 for the corresponding PCT application No. PCT/JP2015/068804.
Castelletto, et al. "Self-Assembly of Palmitoyl Lipopeptides Used in Skin Care Products," Langmuir, https://doi.org/10.1021/la401771j, 2013, vol. 29, pp. 9149-9155.
Japanese Office Action (including English translation) issued in JP2015130876, dated Jun. 11, 2019, 4 pages.
Japanese Office Action (including English translation) issued in JP2015130995, dated Jun. 4, 2019, 6 pages.
Japanese Office Action (including English translation) issued in JP2015130996, dated Jun. 4, 2019, 6 pages.
Japanese Decision of Refusal (with English language translation) for Application No. JP2015-130875, dated Dec. 17, 2019, 5 pages.
Yoshida et al., "New surfactants derived from amino acids and fatty acids", Organic synthetic chemistry, 1975, vol. 33, No. 9, pp. 671-678 (partial English language translation included) (9 pages).

* cited by examiner

COMPOSITION FOR EXTERNAL APPLICATION

CROSS-REFERENCE TO RELATED APPLICATIONS

The present application is a 35 U.S.C. § 371 national phase application from International Application PCT/JP2015/068804, filed on Jun. 30, 2015, which claims the benefit of priority to JP application number 2014-134940, filed on Jun. 30, 2014; JP application number 2014-134941, filed on Jun. 30, 2014; JP application number 2014-134942, filed on Jun. 30, 2014; and JP application number 2014-134943, filed on Jun. 30, 2014 each of which applications are incorporated by reference herein in their entirety.

TECHNICAL FIELD

The following provides explanations of the first present invention to the fourth present invention in that order.

The first present invention relates to an external use composition.

BACKGROUND ART

Aging of skin appears in the form of surface changes such as wrinkles, sagging, dullness or age spots. These changes occur due to decreased proliferation of epidermal cells, reduced epidermal thickness, thickening of the keratin layer or fewer collagen fibers present in the dermis accompanying aging.

Collagen is an important protein that composes the connective tissue of animals, and accounts for nearly 30% of all proteins in the human body in particular. Since the primary function of collagen is to form the framework structures of body tissue, it is widely distributed throughout the skin, cartilage tissue, cornea, heart and liver as the main component composing the framework structures of animal morphology. Since collagen specifically acts on adhesion of various cells as well as cell differentiation and growth, fulfilling the role of a regulatory factor of cell function, a reduction in the level of collagen may cause various diseases including corneal disorders such as corneal ulcer, arthritis (such as arthritis deformans or osteoarthritis), joint disorders such as rheumatoid arthritis, and inflammatory diseases.

Collagen fibers maintain tissue morphology by forming mesh-like bundles in the extracellular matrix of the skin's dermis. Collagen fibers form thick, straight fiber bundles as crosslinking proceeds while they mature and proliferate, and impart a suitable degree of resiliency in young skin. In aged skin, however, the amount of collagen fibers present in the extracellular matrix of the dermis decreases considerably, thereby causing the skin to lose its resiliency and no longer demonstrate elasticity. As a result, wrinkles and sagging are formed in the skin. Detailed studies have been conducted on changes in the structure of collagen fiber bundles induced by photoaging in hairless mice (see Non-Patent Document 1), and it was shown that wrinkles form, the structure of collagen fiber bundles is disrupted as if to coincide with wrinkle formation, and skin elasticity ends up decreasing in hairless mice subjected to UVB irradiation. In addition, collagen is also known to have a superior moisture retention function.

The aforementioned aging of the skin can be suppressed and improved to a certain extent by cosmetics and pharmaceuticals (see Non-Patent Document 2), and for example, cosmetics incorporating hyaluronic acid or the aforementioned collagen, herbal extracts having moisturizing action or coating formation action, or cosmetics incorporating chemically synthesized substances are used. In addition, attempts have also been made to promote the production of hyaluronic acid and collagen by improving the metabolism of the skin per se.

Known examples of substances that promote collagen production include retinoic acid (see Non-Patent Document 3), three types of amino acids consisting of glycine, proline and alanine (see Patent Document 1), plant extracts such as those of licorice, mulberry bark, aloe, field horsetail, Japanese honeysuckle, phellodendron bark, mugwort or gentian (see Patent Document 2), TGF-β, ascorbic acid and collagen degradation products (see Patent Document 3). Moreover, the action of promoting collagen synthesis has been reported to be enhanced by combining the use of ascorbic acid with a low molecular weight betaine (see Patent Document 4), combining with the use of δ-tocopheryl retinoate (see Patent Document 5), and combining with the use of a specific peptide having a specific amino acid sequence (see Patent Document 6).

In addition, although Patent Document 7 describes a gelling agent composed of a specific lipopeptide, there is no specific description regarding an external use composition using this gelling agent, nor is there any description or suggestion whatsoever regarding the specific lipopeptide having the effect of promoting collagen production.

PRIOR ART DOCUMENTS

Patent Documents

[Patent Document 1] Japanese Unexamined Patent Publication No. H7-194375
[Patent Document 2] Japanese Unexamined Patent Publication No. 2001-206835
[Patent Document 3] Japanese Unexamined Patent Publication No. 2000-309521
[Patent Document 4] Japanese Unexamined Patent Publication No. 2005-239645
[Patent Document 5] Japanese Unexamined Patent Publication No. 2005-263794
[Patent Document 6] Japanese Unexamined Patent Publication No. 2008-1661
[Patent Document 7] International Publication No. WO 2010/013555

Non-Patent Documents

[Non-Patent Document 1] Fragrance Journal, 4, p. 36-37, 1998
[Non-Patent Document 2] Mitsui, T., ed., Shin-Keshohin-gaku (New Cosmetology), 2nd edition, Nanzando Co., Ltd., 2001, p. 42-50
[Non-Patent Document 3] R. Marks, et al., British Journal of Dermatology, 122, 91-98, 1990

DISCLOSURE OF THE INVENTION

Problems to be Solved by the Invention

With the foregoing in view, an object of the first present invention is to provide an external use composition having a novel composition for anti-aging that has a superior collagen production promoting effect and is able to suppress, prevent or improve wrinkles and sagging of the skin accompanying aging.

Means for Solving the Problems

The gist of the invention for solving the aforementioned problems, namely the gist of the first present invention, is as indicated below.

<1> An external use composition for anti-aging, comprising (A) a lipopeptide represented by the following formula (1), or a pharmaceutically acceptable salt thereof (to also be referred to as "Component (A)"):

[Chemical 1]

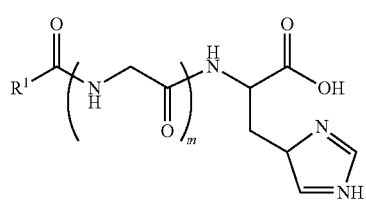

(1)

(wherein, $R^1$ represents a saturated aliphatic group, or aliphatic group having a single unsaturated bond, having 9 to 19 carbon atoms, and m represents 0 or 1).

<2> The external use composition described in <1>, further containing vitamin C.

<3> The external use composition described in <1> or <2>, which is for suppressing, improving or preventing wrinkling or sagging of the skin.

<4> The external use composition described in <1> or <2>, which is for suppressing, improving or preventing decreases in skin resiliency and elasticity.

<5> The external use composition described in any of <1> to <4>, which is for promoting collagen production.

<6> A method for promoting collagen production, comprising the use of (A) a lipopeptide represented by the following formula (1), or pharmaceutically acceptable salt thereof:

[Chemical 2]

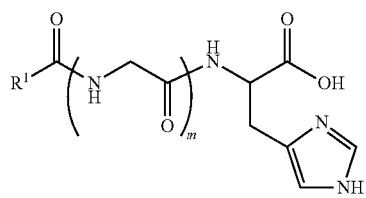

(1)

(wherein, $R^1$ represents a saturated aliphatic group, or aliphatic group having a single unsaturated bond, having 9 to 19 carbon atoms, and m represents 0 or 1).

Effects of the Invention

The external use composition of the first present invention has a superior collagen production promoting effect and is able to suppress, prevent or improve wrinkles and sagging of the skin accompanying aging. In addition, the external use composition of the first present invention is able to effectively suppress aging caused by deterioration of skin condition by also demonstrating a superior ability to promote cell proliferation and activating cells. In this manner, the external use composition of the first present invention is an external use composition having a novel composition for anti-aging not found in the prior art that demonstrates both a superior collagen production promoting effect and cell activating effect. In addition, since Component (A) also acts as a gelling agent, the external use composition of the first present invention can be prepared in a suitable form as necessary. As a result of having such properties, the external use composition of the first present invention can be widely used in cosmetics, quasi drugs and/or pharmaceuticals as an external use composition for anti-aging that demonstrates a collage production promoting effect and cell activating effect.

BRIEF DESCRIPTION OF THE DRAWINGS

FIG. 1-2 is a graph indicating the cell proliferation promoting effect of one embodiment of the first present invention in the form of an external use composition.

FIG. 2-1 is a graph indicating the anti-*Propionibacterium acnes* effect of one embodiment of the second present invention in the form of an external use composition.

FIG. 2-2 is a graph indicating the anti-*Staphylococcus aureus* effect of one embodiment of the second present invention in the form of an external use composition.

FIG. 2-3 is a graph indicating the anti-*Streptococcus mutans* effect of one embodiment of the second present invention in the form of an external use composition.

FIG. 2-4 is a graph indicating the anti-*Escherichia coli* effect of one embodiment of the second present invention in the form of an external use composition.

FIG. 2-5 is a graph indicating the anti-*Pseudomonas aeruginosa* effect of one embodiment of the second present invention in the form of an external use composition.

FIG. 2-6 is a graph indicating the anti-*Malassezia* effect of one embodiment of the second present invention in the form of an external use composition.

FIG. 2-7 is a graph indicating the anti-*Candida* effect of one embodiment of the second present invention in the form of an external use composition.

FIG. 3-1 is a graph indicating the results of a percutaneous absorption test of ascorbic acid on external use compositions of Example 3-1 and Comparative Example 3-1 in an example of the third present invention.

FIG. 3-2 is a graph indicating the results of a percutaneous absorption test of ascorbic acid on external use compositions of Example 3-2 and Comparative Example 3-2 in an example of the third present invention.

FIG. 3-3 is a graph indicating the results of a percutaneous absorption test of ascorbic acid on external use compositions of Example 3-3 and Comparative Example 3-3 in an example of the third present invention.

FIG. 3-4 is a graph indicating the results of a percutaneous absorption test of ascorbic acid on external use compositions of Example 3-4 and Comparative Example 3-4 in an example of the third present invention.

FIG. 3-5 is a graph indicating the results of a percutaneous absorption test of ascorbic acid on external use compositions of Example 3-5 and Comparative Example 3-5 in an example of the third present invention.

FIG. 3-6 is a graph indicating the results of a percutaneous absorption test of ascorbic acid on external use compositions of Example 3-6 and Comparative Example 3-6 in an example of the third present invention.

FIG. 3-7 is a graph indicating the results of a percutaneous absorption test of ascorbic acid on external use compositions of Example 3-7 and Comparative Examples 3-7 to 3-9 in an example of the third present invention.

FIG. 3-8 is a graph indicating the results of a percutaneous absorption test of ascorbic acid on external use compositions of Examples 3-8 to 3-11 and Comparative Examples 3-10 and 3-11 in an example of the third present invention.

FIG. 3-9 is a graph indicating the results of a percutaneous absorption test of ethyl ascorbic acid on external use compositions of Example 3-12 and Comparative Examples 3-12 to 3-14 in an example of the third present invention.

FIG. 3-10 is a graph indicating the results of a percutaneous absorption test of terbinafine hydrochloride on external use compositions of Example 3-13 and Comparative Examples 3-15 and 3-16 in an example of the third present invention.

FIG. 3-11 is a graph indicating the results of a percutaneous absorption test of minoxidil on external use compositions of Example 3-14 and Comparative Example 3-17 in an example of the third present invention.

FIG. 4-1 is a graph indicating the rate of increase in ΔE*ab of the compositions of Examples 4-1 to 4-3 and Comparative Examples 4-1 to 4-3 following storage at 40° C. in an example of the fourth present invention.

FIG. 4-2 is a graph indicating the rate of increase in ΔE*ab of the compositions of Examples 4-1 to 4-3 and Comparative Examples 4-1 to 4-3 following storage at 50° C. in an example of the fourth present invention.

FIG. 4-3 is a graph indicating the rate of increase in ΔE*ab of the compositions of Examples 4-1 to 4-3 and Comparative Examples 4-1 to 4-3 following storage at 60° C. in an example of the fourth present invention.

FIG. 4-4 is a graph indicating the rate of increase in ΔE*ab of the compositions of Example 4-4 and Comparative Example 4-4 following storage at various temperatures in an example of the fourth present invention.

FIG. 4-5 is a graph indicating the rate of increase in ΔE*ab of the compositions of Example 4-5 and Comparative Example 4-5 following storage at various temperatures in an example of the fourth present invention.

FIG. 4-6 is a graph indicating the rate of increase in ΔE*ab of the compositions of Examples 4-6 to 4-9 and Comparative Example 4-6 to 4-9 following storage at various temperatures in an example of the fourth present invention.

FIG. 4-7 is a graph indicating the rate of increase in ΔE*ab of the compositions of Example 4-10 and Comparative Example 4-10 following storage at various temperatures in an example of the fourth present invention.

FIG. 4-8 is a graph indicating the rate of increase in ΔE*ab of the compositions of Comparative Examples 4-3 and 4-11 following storage at 60° C. in an example of the fourth present invention.

BEST MODE FOR CARRYING OUT THE INVENTION

Figure 1:
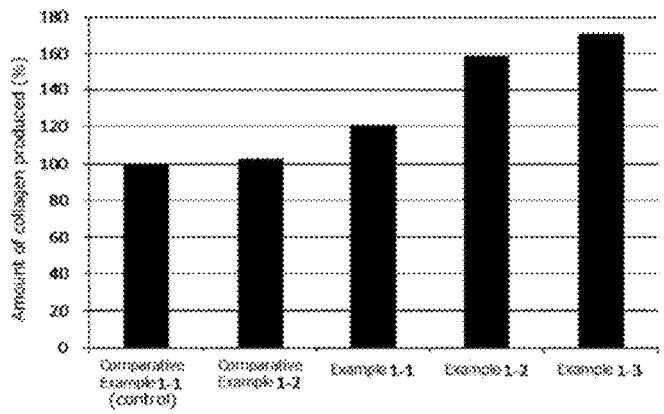
FIG. 1-1 is a graph indicating the collagen production promoting effect of one embodiment of the first present invention in the form of an external use composition.

The following provides a detailed explanation of the first present invention.
<External Use Composition>

The external use composition of the first present invention comprises a lipopeptide represented by the following formula (1), or a pharmaceutically acceptable salt thereof (Component (A)). As a result of comprising Component (A), the external use composition of the first present invention demonstrates a collagen production promoting effect and a cell activating effect in addition to being able to be in the form of a gel. According to the external use composition of the first present invention, decreases in skin resiliency and elasticity can be suppressed, improved or prevented, and wrinkles, sagging of the skin and laugh lines can be suppressed, prevented or improved. In addition, due to the collagen production promoting effect, smoothness of the skin can be retained, and skin texture and softness can be maintained or improved. Furthermore, the external use composition of the first present invention may also contain a solvent or various optional components other than Component (A) for the purpose of improving the effects of the first present invention. The following provides an explanation of Component (A), solvents and optional components.

Here, the "collagen production promoting effect" refers to the effect of increasing the amount of collagen produced in the case of allowing the external use composition to act on cells or skin in comparison with the case of not allowing the external use composition to act thereon. In addition, the "cell activating effect" refers to an effect of promoting cell growth to a greater degree in the case of allowing the external use composition to act on cells in comparison with the case of not allowing the external use composition to act thereon. Furthermore, in a specific aspect, fibroblasts, and particularly skin fibroblasts, are used for the aforementioned cells.

[Component (A)]

Component (A) is a lipopeptide represented by the following formula (1), or a pharmaceutically acceptable salt thereof, and is constructed from a moiety composed of a lipid having a highly liposoluble long chain (alkylcarbonyl group), and a moiety composed of a peptide. Moreover, the moiety composed of a peptide is composed of histidine or glycine-histidine.

[Chemical 3]

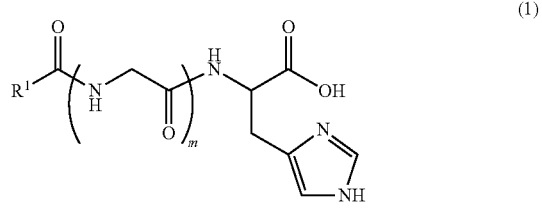

In the above formula, $R^1$ represents a saturated aliphatic group, or aliphatic group having a single unsaturated bond, having 9 to 19 carbon atoms. In addition, m is 0 or 1.

$R^1$ is preferably a saturated aliphatic group or aliphatic group having a single unsaturated bond having 11 to 17 carbon atoms, more preferably a saturated aliphatic group having 11 to 17 carbon atoms, and even more preferably a linear saturated aliphatic group having 11 to 17 carbon atoms from the viewpoints of the collagen production promoting effect and cell activating effect of the external use composition of the first present invention.

Examples of $R^1$ include a nonyl group, decanyl (capryl) group, undecanyl group, dodecanyl group (lauryl group), tridecanyl group, tetradecanyl group (myristyl group), pentadecanyl group, hexadecanyl group (palmityl group), heptadecanyl group, octadecanyl group (stearyl group), nonadecanyl group, nonenyl group, decenyl group, undecenyl group, dodecenyl group, tridecenyl group, tetradecenyl group, pentadecenyl group, hexadecenyl group, heptadecenyl group, octadecenyl group and nonadecenyl group.

Among these, a tetradecanyl group (myristyl group), hexadecanyl group (palmityl group) and octadecanyl group (stearyl group) are preferable from the viewpoints of the collagen production promoting effect and cell activating effect of the external use composition of the first present invention.

Preferable examples of Component (A) in the external use composition of the first present invention in the case m is 0 include N-nonylhistidine, N-decanoylhistidine, N-undecanoylhistidine, N-lauroylhistidine, N-tridecanoylhistidine, N-myristoylhistidine, N-pentadecanoylhistidine, N-palmitoylhistidine, N-heptadecanoylhistidine, N-stearoylhistidine, N-nonadecanoylhistidine and N-eicosanoylhistidine.

In addition, preferable examples in the case m is 1 include N-nonylglycinyl-histidine, N-decanoylglycinyl-histidine, N-undecanoylglycinyl-histidine, N-lauroylglycinyl-histidine, N-tridecanoylglycinyl-histidine, N-myristoylglycinyl-histidine, N-pentadecanoylglycinyl-histidine, N-palmitoyl-glycinyl-histidine, N-heptadecanoylglycinyl-histidine, N-stearoylglycinyl-histidine, N-nonadecanoylglycinyl-histidine and N-eicosanoylglycinyl-histidine.

Furthermore, either L-form or R-form optically active histidine can be used for the histidine moiety in Component (A). Since the external use composition of the first present invention is preferably used in a cosmetic, quasi drug or pharmaceutical, a lipopeptide having the L-form of histidine present in the body is used particularly preferably.

Examples of pharmaceutically acceptable salts of the lipopeptide represented by the aforementioned formula (1) include salts corresponding to the carboxyl group of histidine in the manner of alkaline metal salts such as lithium salts, sodium salts, potassium salts or calcium salts, and salts corresponding to the imidazole group of histidine in the manner of salts of inorganic acids such as hydrochlorides, sulfates or phosphates, and salts of organic acids such as acetates, carbonates, citrates or succinates.

Component (A) in the form of a lipopeptide or pharmaceutically acceptable salt as described above can be produced according to a method known among persons with ordinary skill in the art. For example, Component (A) can be produced by linking an amino acid composing a lipopeptide by peptide solid-phase synthesis, reacting the N-terminal of the amino acid located on the end as viewed from the solid phase with the fatty acid serving as the lipid moiety, and then forming into a salt as necessary. In addition, Component (A) can be produced by starting from a fatty acid, linking an amino acid thereto and then forming into a salt as necessary using a liquid phase method.

In the first present invention, one type of Component (A) may be used alone or two or more types may be used in an arbitrary combination. The content of Component (A) in the entire external use composition (in 100% by weight thereof) of the first present invention is normally 0.0001% to 5% by weight, preferably 0.0005% to 3% by weight, and more preferably 0.001% to 1.5% by weight from the viewpoints of the collagen production promoting effect and cell activating effect.

[Solvent]

The external use composition of the first present invention comprises water, alcohol, hydrophilic organic solvent, fatty acid, higher fatty acid ester, glyceride, or hydrophobic organic solvent or a mixed solvent miscible therewith. When Component (A) is added to these solvents at a specific ratio, gelling occurs and an external use composition can be obtained having a suitable viscosity that enables it to favorably work into the skin.

The preferable solvent functions as a base or carrier in the external use composition, and examples thereof include aqueous solvents such as water, hydrocarbons in the manner of liquid paraffin, squalane, Vaseline, gelling hydrocarbons (such as plastibase), ozokerite, α-olefin oligomers or light liquid paraffin, silicone oils in the manner of methylpolysiloxanes such as poly(methylsilsesquioxane), crosslinked methyl polysiloxane, highly polymerized methyl polysiloxane, cyclic silicone, alkyl-modified silicone, crosslinked alkyl-modified silicone, amino-modified silicone, polyether-modified silicone, polyglycerin-modified silicones such as lauryl dimethicone polyglycerin-3 crosspolymer, crosslinked polyether-modified silicone, crosslinked alkyl polyether-modified silicone, silicone-alkyl chain-co-modified polyether-modified silicone, silicone-alkyl chain-co-modified polyglycerin-modified silicone, polyether-modified branched silicone, polyglycerin-modified branched silicone, acrylsilicone, phenyl-modified silicone or silicon oil such as silicone resin, higher alcohols in the manner of cetanol, cetostearyl alcohol, stearyl alcohol or behenyl alcohol, cellulose derivatives in the manner of ethyl cellulose, hydroxypropyl cellulose or hydroxypropyl methyl cellulose, polyvinylpyrrolidone, carrageenan, polyvinylbutyrate, polyethylene glycol, dioxane, butylene glycol polyester adipate, esters in the manner of isopropyl myristate, octyldodecyl myristate, isopropyl palmitate, cetyl palmitate, octyl palmitate, isononyl isononanoate, pentaerythritol tetra(2-ethylhexanoate), glyceryl tri(2-ethylhexanoate) or jojoba oil, polysaccharides in the manner of dextrin or maltodextrin, and alcohols in the manner of ethanol or isopropanol. Among these, aqueous solvents are preferable and water is particularly preferable.

In the case the external use composition of the first present invention comprises water, although the amount incorporated therein can be suitably selected in consideration of the feel on the skin during use and the effects of the first present invention, it is, for example, 0.001% to 99.5% by weight, preferably 0.01% to 90% by weight, more preferably 0.1% to 60% by weight and most preferably 1% to 20% by weight based on the total weight of the external use composition of the first present invention.

[Optional Components]

The external use composition of the first present invention preferably further comprises a vitamin in addition to the Component (A) for the purpose of improving the effects of the first present invention. Furthermore, one type of vitamin may be used alone or two or more types may be used in an arbitrary combination. In addition, disinfectants, polyvalent alcohols, glycol ether or thickeners and the like may also be used as optional components in addition to those listed above within a range that does not impair the effects of the first present invention. Furthermore, in the case compounds indicated as specific examples of each component are duplicated, any of those components may be contained.

(Vitamins)

Examples of the aforementioned vitamins include vitamin A compounds such as retinol, retinol derivatives such as retinol acetate or retinol palmitate, retinal, retinoic acid, methyl retinoate, ethyl retinoate, retinol retinoate, d-δ-tocopheryl retinoate, α-tocopheryl retinoate or β-tocopheryl retinoate, provitamin A compounds such as β-carotene, α-carotene, γ-carotene, δ-carotene, lycopene, zeaxanthin, cryptoxanthin or echinenone, vitamin E compounds such as δ-tocopherol, α-tocopherol, β-tocopherol, dl-α-tocopherol succinate, calcium dl-α-tocopherol succinate, S-tocopherol or tocopherol nicotinate, vitamin B2 compounds such as riboflavin, flavin mononucleotide, flavin adenine dinucleotide, riboflavin butyrate, riboflavin tetrabutyrate, riboflavin 5'-phosphate sodium or riboflavin tetranicotinate, nicotinic acids such as methyl nicotinate, nicotinic acid or nicotinic acid amide, vitamin C compounds such as ascorbyl stearate, L-ascorbyl dipalmitate, ascorbyl tetraisopalmitate (ascorbyl tetra-2-hexyldecanoate), ascorbic acid, sodium ascorbate, dehydroascorbic acid, sodium ascorbyl phosphate, magnesium ascorbyl phosphate, ascorbyl glucoside or 3-O-ethyl ascorbic acid, vitamin D compounds such as methyl hesperidin, ergocalciferol or cholecalciferol, vitamin K compounds such as phylloquinone or farnoquinone, vitamin B1 compounds such as dibenzoylthiamine, dibenzoylthiamine hydrochloride, thiamine hydrochloride, thiamine cetyl hydrochloride, thiamine thiocyanate, thiamine lauryl hydrochloride, thiamine nitrate, thiamine monophosphate, thiamine diphosphate, thiamine triphosphate, thiamine monophosphate ester phosphate, thiamine monophosphate ester, thiamine diphosphate ester, thiamine triphosphate ester hydrochloride, thiamine triphosphate ester or thiamine triphosphate ester monophosphate, vitamin B6 compounds such as pyridoxine hydrochloride, pyridoxine acetate, pyridoxal hydrochloride, pyridoxal 5'-phosphate or pyridoxamine hydrochloride, vitamin B12 compounds such as cyanocobalamin, hydroxocobalamin or deoxyadenosylcobalamin, folic acid compounds such as folic acid or pteroylglutamic acid, pantothenates such as pantothenic acid, calcium pantothenate, pantothenyl alcohol (panthenol), D-pantetheine, D-pantethine, coenzyme A or pantothenyl ethyl ether, biotins such as biotin or biocytin, and other vitamin-like agents such as carnitine, ferulic acid, α-lipoic acid, orotic acid or γ-oryzanol.

Among these, vitamin C compounds such as ascorbyl stearate, L-ascorbyl dipalmitate, ascorbyl tetraisopalmitate (ascorbyl tetra-2-hexyldecanoate), ascorbic acid, sodium ascorbate, dehydroascorbic acid, sodium ascorbyl phosphate, magnesium ascorbyl phosphate or ascorbyl glucoside are preferable and L-ascorbic acid is more preferable from the viewpoint of demonstrating a potent effect of enhancing the collagen production promoting effect of the external use composition of the first present invention. Furthermore, among these vitamin C compounds, a portion of vitamin C derivatives thereof act by being converted to vitamin C by an enzyme in the body. For example, ascorbyl glucoside is decomposed to ascorbic acid and glucose in the body, and the resulting ascorbic acid is thought to act so as to enhance the collagen production promoting effect.

In the case of incorporating a vitamin, although the amount used can be suitably selected in consideration of the feel on the skin during use, the collagen production promoting effect and the cell activating effect, the amount of vitamin used is, for example, 0.0001% to 30% by weight, preferably 0.0005 to 25% by weight and more preferably 0.001% to 20% by weight based on the total weight of the external use composition of the first present invention.

(Disinfectant)

The external use composition of the first present invention can contain a disinfectant in the form of a 1,2-alkanediol. Examples of 1,2-alkanediols used in the first present invention include 1,2-alkanediols represented by the following formula (2).

$$R^2-CH(OH)-CH_2-OH \quad (2)$$

In the above formula, $R^2$ represents an alkyl group having 2 to 8 carbon atoms. The alkyl group may be linear or branched.

Examples of the 1,2-alkanediol contained in the external use composition of the first present invention include 1,2-butanediol, 1,2-pentanediol, 1,2-hexanediol, 1,2-heptanediol, 1,2-octanediol and 1,2-decanediol. Among these, 1,2-hexanediol and 1,2-octanediol are preferable, and 1,2-octanediol is more preferable.

The content of the 1,2-alkanediol in the entire external use composition (100% by weight) of the first present invention is preferably 0.01% to 15% by weight and more preferably 0.1% to 10% by weight from the viewpoint of antibacterial activity.

The external use composition of the first present invention can contain a disinfectant in the form of a quaternary ammonium salt-based disinfectant. Examples of quaternary ammonium salt-based disinfectants used in the first present invention include quaternary ammonium salts represented by the following formula (3).

[Chemical 4]

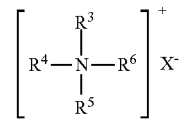

(3)

In formula (3) above, $R^3$ and $R^4$ respectively and independently represent an alkyl group having 1 to 3 carbon atoms. $R^5$ represents a group represented by the following formula (4). $R^6$ represents an alkyl group or alkenyl group having 1 to 4 carbon atoms. $X^-$ represents a chloride ion or bromide ion.

[Chemical 5]

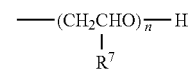

(4)

In formula (4) above, $R^7$ represents an alkyl group having 1 to 4 carbon atoms. n represents an integer of 3 to 60.

The aforementioned $R^7$ is preferably a methyl group and n is preferably an integer of 9 to 41. Preferable examples of the quaternary ammonium salt-based disinfectant contained in the external use composition of the first present invention include those in which $R^5$ in the aforementioned formula (3) is a polyoxypropylene group that is a polymer having 9 to 41 oxypropylene units, such as polyoxypropylene (9) methyl diethyl ammonium chloride, polyoxypropylene (25) methyl diethyl ammonium chloride or polyoxypropylene (40) methyl diethyl ammonium chloride. Examples of commercially available products thereof include Emcol CC-9, CC-36 and CC-42 manufactured by Witco Chemical Company, and Adekacol EC-CC-9, EC-CC-36 and EC-CC=42 manufactured by Asahidenka Kogyo(Corp). Moreover, other preferable examples include cetylpyridinium chloride, benzalkonium chloride and benzethonium chloride.

Among these, cetylpyridinium chloride, benzalkonium chloride and benzethonium chloride are preferable from the viewpoints of antibacterial activity and safety.

The external use composition of the first present invention can use a poorly water-soluble active disinfectant as a disinfectant. Here, a poorly water-soluble active disinfectant refers to a substance demonstrating both bactericidal and bacteriostatic action and having solubility in water at 25° C. of less than 1% by weight (w/v). These poorly water-soluble active disinfectants are broadly classified into phenol-based substances and alcohol-based substances.

Examples of phenol-based substances include triclosan, trichlorocarbanilide, methylparaben, ethylparaben, propylparaben and isopropyl methylphenol. Examples of alcohol-based substances include dodecyl alcohol and decyl alcohol.

The poorly water soluble active disinfectant may be composed of a single substance, may be composed by mixing a plurality of phenol-based substances, may be composed by mixing a plurality of alcohol-based substances, or may be composed by mixing a phenol-based substance and an alcohol-based substance.

A disinfectant used as a disinfectant of a cosmetic, quasi drug or pharmaceutical can be used without restriction for the other disinfectant used in the external use composition of the first present invention. Examples thereof include dequalinium chloride, chlorhexidine hydrochloride, chlorhexidine gluconate, alkyldiaminoethylglycine hydrochloride, cetylpyridinium chloride, sodium benzoate, chlorobutanol, salicylic acid, gluconic acid, thymol, hexachlorophene, berberine, terbinafine hydrochloride, lysozyme chloride, salicylic acid, salicylate, sulfur or sulfur compounds, hinokitiol, triclosan, trichlorocarbanilide, halocarban, chlorphenesin, sorbic acid, potassium sorbate, sodium dehydroacetate, methyl paraoxybenzoate, ethyl paraoxybenzoate, propyl paraoxybenzoate, butyl paraoxybenzoate, oxyquinoline sulfate, phenethyl alcohol, benzyl alcohol and biguanide compounds.

Among these other disinfectants, methyl paraoxybenzoate, ethyl paraoxybenzoate, propyl paraoxybenzoate, butyl paraoxybenzoate, dequalinium chloride, chlorhexidine hydrochloride, chlorhexidine gluconate, cetylpyridinium chloride and thymol are preferable from the viewpoints of antibacterial activity and safety. Furthermore, the content of other disinfectants in the external use composition of the first present invention is a concentration of 0.0001% to 1% by weight in the entire external use composition (100% by weight) of the first present invention.

(Polyvalent Alcohol)

The external use composition of the first present invention can contain a polyvalent alcohol. A polyvalent alcohol used in cosmetics, quasi drugs or pharmaceuticals can be used without restriction as the polyvalent alcohol used in the external use composition of the first present invention. Examples thereof include glycols (such as ethylene glycol, diethylene glycol, propylene glycol, isopropylene glycol, dipropylene glycol, polypropylene glycol, polyethylene glycol, 1,3-butylene glycol or pentylene glycol), glycerin, diglycerin, triglycerin, polyglycerin, sorbitol and alkanediols (such as propanediol, 3-methyl-1,3-butanediol or pentanediol). Among these, propylene glycol, dipropylene glycol, 1,3-butylene glycol, pentylene glycol, glycerin, diglycerin, sorbitol and alkanediols (propanediol, pentanediol and hexanediol) are preferable from the viewpoints of formulating in consideration of feel on the skin during use, while dipropylene glycol, 1,3-butylene glycol and pentylene glycol are more preferable. One type of these polyvalent alcohols can be used alone or two or more types can be used in combination.

The content of polyvalent alcohol in the external use composition of the first present invention is preferably 0.01% by weight or more, more preferably 0.1% by weight or more, and even more preferably 0.5% by weight or more in the entire external use composition (100% by weight) of the first present invention. In addition, the content of polyvalent alcohol in the entire external use composition (100% by weight) of the first present invention is preferably 97% by weight or less, more preferably 50% by weight or less and even more preferably 30% by weight or less. If within the aforementioned ranges, moisture retention and a favorable feel on the skin during use can be imparted to the external use composition in addition to the effects of the first present invention.

(Glycol Ether)

The external use composition of the first present invention can further contain glycol ether. A glycol ether used in cosmetics, quasi drugs or pharmaceuticals can be used without restriction as the glycol ether used in the external use composition of the first present invention. Examples thereof include ethylene glycol-based glycol ethers in the manner of ethylene glycol monomethyl ether, ethylene glycol monoethyl ether and ethylene glycol monopropyl ether, diethylene glycol-based glycol ethers in the manner of diethylene glycol monomethyl ether, diethylene glycol monoethyl ether and diethylene glycol monopropyl ether, propylene glycol-based glycol ethers in the manner of propylene glycol monoethyl ether and propylene glycol monopropyl ether, and dipropylene glycol-based glycol ethers in the manner of dipropylene glycol monoethyl ether and dipropylene glycol monopropyl ether. Among these, ethylene glycol-based glycol ethers and diethylene glycol-based glycol ethers are preferable, ethylene glycol monomethyl ether and diethylene glycol monoethyl ether are more preferable, and diethylene glycol monoethyl ether is particularly preferable. One type of these glycol ethers can be used alone or two or more types can be used in combination.

The content of glycol ether in the entire external use composition (100% by weight) of the first present invention is preferably 0.01% by weight or more, more preferably 0.1% by weight or more and even more preferably 0.5% by weight or more. In addition, the content of glycol ether in the entire external use composition (100% by weight) is preferably 97% by weight or less, more preferably 75% by weight or less and even more preferably 50% by weight or less. If within the aforementioned ranges, moisture retention and a favorable feel on the skin during use can be imparted to the external use composition in addition to the effects of the first present invention.

(Thickener)

The external use composition of the first present invention can further contain a thickener. As a result, an external use composition demonstrating superior adaptability with skin and superior feel on the skin during use can be obtained.

A thickener used as a thickener of a cosmetic, quasi drug or pharmaceutical can be used without restriction for the thickener used in the external use composition of the first present invention. Examples thereof include agar, gellan gum, gua gum, locust bean gum, carrageenan, xanthan gum, dextran, methyl cellulose, ethyl cellulose, carboxymethyl cellulose, hydroxymethyl cellulose, hydroxyethyl cellulose, hydroxypropyl cellulose, hydroxypropyl methyl cellulose, carboxymethyl cellulose, carboxyethyl cellulose, sodium alginate, propylene alginate glycol ester, dextran, polyvinyl alcohol, polyvinylpyrrolidone, polyvinyl methyl ether, carboxyvinyl polymer, acrylic acid-alkyl methacrylate copolymer, sodium polyacrylate, polyethylene glycol, bentonite, dextrin fatty acid ester, pectin, hydroxyethyl acrylate-sodium acryloyldimethyl taurate copolymer, dimethyl distearyl ammonium hectorite, ammonium acryloyldimethyl taurate-vinylpyrrolidone copolymer, ammonium acryloyldimethyl taurate-beheneth-25 methacrylate crosspolymer ammonium acryloyldimethyltaurate-steareth-25 methacrylate crosspolymer, polyethylene glycol distearate, ethylene glycol triisostearate and polyoxyethylene (20) triisostearate methyl glucoside. Among these, methyl cellulose, ethyl cellulose, hydroxyethyl cellulose, hydroxymethyl cellulose, hydroxypropyl cellolose, hydroxypropyl methyl cellulose, carboxymethyl cellulose, carboxyethyl cellulose, xanthan gum, acrylic acid-alkyl methacrylate copolymer, hydroxyethyl acrylate-sodium acryloyldimethyl taurate copolymer and ammonium acryloyldimethyl taurate-vinylpyrrolidone copolymer are more preferable. One type of these thickeners may be used alone or two or more types may be used in an arbitrary combination.

The content of thickener in the external use composition of the first present invention is preferably 0.0001% to 20% by weight, more preferably 0.001% to 10% by weight and even more preferably 0.05% to 5% by weight in the entire external use composition (100% by weight) of the first present invention. If the content of thickener is within the aforementioned ranges, an external use composition can be obtained that demonstrates superior adaptability with skin and superior feel on the skin during use.

(Other Components)

The external use composition of the first present invention may incorporate one type or two or more types of various other optional components in addition to the components described above in order to add other useful effects, examples of which include an ultraviolet scattering component, ultraviolet absorbing component, component having action that prevents and/or repairs damaged DNA, whitening component, anti-inflammatory component, cell activating component, astringent component, antioxidant component, anti-aging component, moisturizing component, keratin softening component, circulation promoting component, sebaceous matter absorbing component and hair growth component. Any arbitrary component able to be used in the pharmaceutical, quasi drug and cosmetic fields can be suitably selected and used for each of these components without any particular limitations. In addition, components corresponding to a plurality of the components indicated below can be added as components having an arbitrary effect thereof.

Examples of the aforementioned ultraviolet scattering component include inorganic compounds such as zinc oxide, titanium oxide, iron oxide, cerium oxide, zirconium oxide, titanium silicate, zinc silicate, silicic anhydride, cerium silicate or hydrated silicic acid, ultraviolet scattering components obtained by coating these inorganic compounds with an inorganic powder such as hydrated silicic acid, aluminum hydroxide, mica or talc, ultraviolet scattering components obtained by compounding into a resin powder such as polyamide, polyethylene, polyester, polystyrene or nylon, and ultraviolet scattering components obtained by treating these inorganic compounds with silicone oil or fatty acid aluminum salts. Among these, inorganic compounds such as zinc oxide, titanium oxide or iron oxide, and these inorganic compounds coated with an inorganic powder, such as aluminum hydroxide, hydrated silicic acid, mica or talc, or silicone oil are preferable.

In the case of incorporating an ultraviolet scattering component, although the amount used thereof can be suitably selected in consideration of the feel on the skin during use and the effect thereof, the amount used is, for example, 0.001% to 35% by weight and preferably 1% to 25% by weight based on the total weight of the external use composition of the first present invention.

Examples of the aforementioned ultraviolet absorbing component include 2-ethylhexyl para-methoxycinnamate, hexyl 2-[4-(diethylamino)-2-hydroxybenzoyl]benzoate, 2,4,6-tris[4-(2-ethylhexyloxycarbonyl)anilino]-1,3,5-triazine, 2-ethylhexyl dimethoxybenzylidene oxoimidazolidine propionate and 2,4-bis[{4-(2-ethylhexyloxy)-2-hydroxy}-phenyl]-6-(4-methoxyphenyl)-1,3,5-triazine.

In the case of incorporating an ultraviolet absorbing component, although the amount used thereof can be suitably selected in consideration of the feel on the skin during use and the effect thereof, the amount used is, for example, 0.01% to 20% by weight and preferably 0.1% to 15% by weight based on the total weight of the external use composition of the first present invention.

Examples of the aforementioned whitening component include hydroquinone, placenta extract, arbutin, kojic acid, ellagic acid, phytic acid, tranexamic acid, 4-n-butylresorcinol, chamomile extract, and vitamins such as vitamin A and derivatives thereof or pantothenic acid and derivatives thereof. Moreover, a plant component having whitening action may also be used as a whitening component, and examples of such plant components include components derived from iris, almond, aloe, ginkgo, oolong tea, rose fruit, scutellaria root, coptis, St. John's wort, deadnettle, kelp, pueraria root, gardenia, sophora root, chlorella, gallnut wheat, rice, rice germ, oryzanol, rice bran, asiasarium root, pepper, perilla, peony, cnidium, mulberry bark, soybean, fermented soybean, angelica root, calendula, garlic, witch hazel, safflower, moutan bark, coix, angelica root, amethyst, gambir, bracken fern, Buddhist pine, hackberry, persimmon (Dispyros kaki), catalpa, black soybean, gentian, scrophularia, sarsaparilla, green bean, windmill palm, sage, peucedanum root, radish, azalea, bush clover, barrenwort, bitterwood, parsley, holly, hop, leafy lespedeza, clove, licorice and grapefruit. Preferable examples include components derived from iris, aloe, ginkgo, oolong tea, rose fruit, scutellaria root, coptis, St. John's wort, deadnettle, kelp, pueraria root, gardenia, sophora root, gallnut, wheat, rice, rice bran, asiasarium root, pepper, perilla, peony, cnidium, mulberry bark, tea, angelica root, pot marigold, witch hazel, safflower, moutan bark, coix, amethyst, gambir, hackberry, persimmon (Dispyros kaki), catalpa, black soybean, gentian, sarsaparilla, green bean, windmill palm, sage, peucedanum root, radish, azalea, bush clover, barrenwort, bitterwood, parsley, holly, hop, clove, licorice, grapefruit and angelica root, while more preferable examples include components derived from iris, aloe, ginkgo, rose fruit, scutellaria root, coptis, St. John's wort, gardenia, sophora root, rice, rice bran, asiasarium root, peony, cnidium, mulberry bark, tea, angelica root, pot marigold, witch hazel, safflower, moutan bark, amethyst, gambir, hackberry, persimmon (Dispyros kaki), sage, radish, azalea parsley, hop, licorice, grapefruit and coix. Among these, an iris-derived component in the form of iris root extract and kelp-derived components in the form of brown algae extract or sugar kelp extract, and aloe extract are more preferable.

In the case of using these plant components in the external use composition of the first present invention, although there are no particular limitations on the form the plant components, the plant components are normally used in the form of a plant extract or essential oil thereof. Furthermore, terms indicated in parentheses in the descriptions of the aforementioned plant components refer to the scientific name, alternative name or herbal medicine name of that plant. In the case of incorporating a whitening component as explained above in the external use composition of the first present invention, although the amount used thereof can be suitably selected in consideration of the feel on the skin during use and effect thereof, the amount used is, for example, 0.0003% to 10% by weight and preferably 0.01% to 5% by weight based on the total weight of the external use composition. In the case of using a plant extract, the amount used as the amount of extract is 0.00001% to 20% by weight, preferably 0.0001% to 15% by weight and more preferably 0.001% to 10% by weight based on the total weight of the external use composition.

Examples of the aforementioned anti-inflammatory component include allantoin, calamine, tranexamic acid, glycyrrhizic acid, derivatives thereof or salts thereof, glycyrrhetic acid, derivatives thereof or salts thereof, zinc oxide, guaiazulene, tocopherol acetate, pyridoxine hydrochloride, menthol, camphor, terpene oil, indomethacin, and salicylic acid or derivatives thereof. Preferable examples include glycyrrhizic acid, derivatives thereof or salts thereof (such as dipotassium glycyrrhizate, glycyrrhetic acid, derivatives thereof or salts thereof and zinc oxide. In the case of incorporating an anti-inflammatory component, although the amount used thereof can be suitably selected in consideration of the feel on the skin during use and the effect thereof, the amount used is, for example, 0.0003% to 10% by weight and preferably 0.01% to 5% by weight based on the total weight of the external use composition of the first present invention.

Examples of the aforementioned cell activating component include amino acids such as γ-aminobutyric acid or ε-aminocaproic acid, α-hydroxy acids such as glycolic acid or lactic acid, tannin, flavonoids, saponin, allantoin and photosensitizer 301. In the case of incorporating a cell activating component, although the amount used thereof can be suitably selected in consideration of feel on the skin during use and the effect thereof, the amount used is, for example, 0.0003% to 10% by weight and preferably 0.01% to 5% by weight based on the total weight of the external use composition of the first present invention.

Examples of the aforementioned astringent component include metal salts such as alum, aluminum chlorohydrate, aluminum chloride, allantoin aluminum salt, zinc sulfate or potassium aluminum sulfate, and organic acids such as tannic acid, citric acid, lactic acid or succinic acid.

In the case of incorporating an astringent component, although the amount used thereof can be suitably selected in consideration of the feel on the skin during use and the effect thereof, the amount used is, for example, 0.0003% to 10% by weight and preferably 0.01% to 5% by weight based on the total weight of the external use composition of the first present invention.

Examples of the aforementioned antioxidant component include butylhydroxyanisole, dibutylhydroxytoluene, sodium hydrogen sulfite, sodium pyrosulfite, flavonoids, glutathione, glutathione peroxidase, glutathione-S-transferase, catalase, superoxide dismutase, thioredoxin, taurine, thiotaurine, hypotaurine, L-cysteine hydrochloride and astaxanthin. In the case of incorporating an antioxidant component, although the amount used thereof can be suitably selected in consideration of the feel on the skin during use and the effect thereof, the amount used 0.00001% to 10% by weight, preferably 0.0001% to 5% by weight and more preferably 0.001% to 5% by weight based on the total weight of the external use composition of the first present invention.

Examples of the aforementioned anti-aging component include pangamic acid, ursolic acid, turmeric extract, sphingosine derivatives, silicon, silicic acid, N-methyl-L-serine and mevalonolactone. In the case of incorporating an anti-aging component, although the amount used thereof can be suitably selected in consideration of the feel on the skin during use and the effect thereof, the amount used is, for example, 0.0003% to 10% by weight and preferably 0.01% to 5% by weight based on the total weight of the external use composition of the first present invention.

Examples of the aforementioned moisturizing component include amino acids such as alanine, serine, leucine, isoleucine, threonine, glycine, trimethylglycine, proline, hydroxyproline, glucosamine, theanine and derivatives thereof, polyvalent alcohols such as glycerin, sugar-alcohols such as sorbitol, phospholipids such as lecithin or hydrogenated lecithin, NMF-derived components such as lactic acid, sodium pyrrolidone carboxylate or urea, and vegetable oil-derived components such as lavender oil or glasswort extract. In the case of incorporating a moisturizing component, although the amount used thereof can be suitably selected in consideration of feel on the skin during use and the effect thereof, the amount used is, for example, 0.1% to 10% by weight and preferably 0.5% to 5% by weight based on the total weight of the external use composition of the first present invention.

Examples of the aforementioned keratin softening component include lanolin, urea, phytic acid, lactic acid, lactate, glycolic acid, salicylic acid, malic acid and citric acid.

In the case of incorporating a keratin softening component, although the amount used thereof is suitably selected in consideration of the feel on the skin during use and the effect thereof, the amount used is, for example, 0.0001% to 50% by weight, preferably 0.001% to 50% by weight and more preferably 0.05% to 25% by weight based on the total weight of the external use composition of the first present invention.

Examples of the aforementioned circulation promoting component include components derived from vegetable (such as Asian ginseng, Angelica keiskei, mountain arnica, gingko, fennel, Isodonis japonicus, Dutch oak, chamomile, Roman chamomile, Daucus carota sativa, gentian, burdock, rice, Japanese hawthorn, shiitake mushroom, English hawthorn, juniper, cnidium, thyme, clove, citrus unshiu, angelica root, peach kernel, spruce, carrot, garlic, butcher's broom, grape, peony, horse chestnut, lemon balm, yuzu, coix, rosemary, rose hip, citrus unshiu, angelica, spruce, peach, apricot, walnut or corn), tocopherol nicotinate, glucosyl hesperidin and hesperidin.

In the case of incorporating a circulation promoting component, although the amount used thereof can be suitably selected in consideration of the feel on the skin during use and the effect thereof, the amount used is, for example, 0.00001% to 10% by weight, preferably 0.0001% to 5% by weight, and more preferably 0.001% to 5% by weight based on the total weight of the external use composition of the first present invention. The amount used in the case of using a component derived from a vegetable as the amount of extract and the like is 0.00001% to 20% by weight, preferably 0.0001% to 15% by weight and more preferably 0.001% to 10% by weight based on the total weight of the external use composition.

Examples of the aforementioned sebaceous matter adsorbing component include talc, mica, hydroxyapatite, zinc oxide and aluminum silicate. Among these, mica, hydroxyapatite and zinc oxide are preferable, while mica is particularly preferable. In the case of incorporating a sebaceous matter adsorbing component, although the amount used thereof can be suitably selected in consideration of the feel on the skin during use and the effect thereof, the amount used is, for example, 0.001% to 35% by weight and preferably 0.1% to 25% by weight based on the total weight of the external use composition of the first present invention.

Examples of the aforementioned hair growth component include procyanidin, dipotassium glycyrrhizate, carpronium chloride, cepharanthine, menthol, hinokitiol, L-hydroxyproline, acetyl hydroxyproline, fucoidan, capsicum tincture, cepharanthine, swertiamarin, panax ginseng, flavonosteroid, minoxidil, FGF-10, Isodonis japonicus extract, Swertia herb extract, ribbon weed extract, five-leaf ginseng extract, St. John's wort extract, gentian extract, sage extract, peppermint extract, hop extract, coix extract, persimmon leaf extract, rehmannia root extract, carrot extract, Bohdi tree extract, moutan bark extract and tree bark extract.

In addition, the external use composition of the first present invention may also suitably incorporate components ordinarily used in the fields of pharmaceuticals, quasi drugs and cosmetics corresponding to the application or drug form thereof in addition to each of the aforementioned components. There are no particular limitations on components that can be incorporated, and examples of additives that can be incorporated include a surfactant, preservative, pH adjuster, chelating agent, stabilizer, irritation reducing agent, colorant, dispersant and fragrance. Furthermore, one type of these components can be incorporated alone or two or more types can be arbitrarily combined. In addition, the amounts used can be suitably determined within a range extending from the range of the prior art that does not impair the effects of the first present invention.

Examples of the aforementioned surfactant include various types of nonionic surfactants in the manner of sorbitan esters such as sorbitan stearate, PEG sorbitan stearate, sorbitan monooleate, sorbitan monoisostearate and sorbitan monolaurate, POE-sorbitan monooleate, polyoxyethylene hydrogenated castor oil (HCO-10), glycerin fatty acid esters such as glycerin monooleate, glycerin monostearate or glycerin monomyristate, glycerin alkyl ethers such as monoisostearyl glyceryl ether or monomyristyl glyceryl ether, and polyglycerin fatty acid esters such as polyglyceryl stearate, polyglyceryl-10 isostearate, diglyceryl monostearate, decaglyceryl decastearate, decaglyceryl decaisostearate or diglyceryl diisostearate, and naturally derived surfactants such as lecithin, hydrogenated lecithin, saponin, surfactin sodium salt, cholesterol or bile acid.

Examples of the aforementioned preservative include benzoic acid, sodium benzoate, dehydroacetic acid, sodium dehydroacetate, isobutyl paraoxybenzoate, isopropyl paraoxybenzoate, butyl paraoxybenzoate, ethyl paraoxybenzoate, propyl paraoxybenzoate, benzyl paraoxybenzoate, methyl paraoxybenzoate and phenoxyethanol.

Examples of the aforementioned pH adjuster include inorganic acids (such as hydrochloric acid or sulfuric acid), organic acids (such as lactic acid, sodium lactate, citric acid, sodium citrate, succinic acid or sodium succinate), inorganic bases (such as potassium hydroxide or sodium hydroxide), and organic bases (such as triethanolamine, diisopropanolamine or triisopropanolamine).

Examples of the aforementioned chelating agent include ethylenediamine tetraacetic acid (edetic acid), ethylenediamine tetraacetate (such as sodium salt (sodium edetate: Japanese Pharmacopeia, EDTA-2Na) or potassium salt), phytic acid, gluconic acid, polyphosphoric acid or metaphosphoric acid. Among these, sodium edetate is preferable.

Examples of the aforementioned stabilizer include magnesium sulfate, sodium polyacrylate, dibutylhydroxytoluene and butylhydroxyanisole.

Examples of the aforementioned irritation reducing agent include licorice extract, gum arabic, polyvinylpyrrolidone and sodium alginate.

Examples of the aforementioned colorant include inorganic pigments and natural pigments.

Examples of the aforementioned dispersant include sodium pyrophosphate, sodium hexametaphosphate, polyvinyl alcohol, polyvinylpyrrolidone, methyl vinyl ether-maleic anhydride copolymer and organic acids.

[pH]

Although the external use composition of the first present invention may normally be provided with liquidity and have a pH of 2.0 to 9.0, pH is preferably 3.0 to 8.5 and more preferably 3.5 to 8.0 from the viewpoints of reduced irritation of the skin and mucous membranes and favorable feel on the skin during use.

[Form and Preparations]

There are no particular limitations on the form of the external use composition of the first present invention, and can be in the form of a liquid, fluid or semi-solid. In addition, examples of preparation forms that can be adopted include a liquid, suspension, emulsion, cream, milky lotion, ointment, gel, liniment, lotion and sheet obtained by impregnating a non-woven fabric with a drug. Among these, an emulsion, cream, milky lotion, ointment, gel and lotion are preferable, and a cream, milky lotion, ointment and gel are particularly preferable.

Furthermore, a container of a known shape can be used without restriction for the container into which the external use composition of the first present invention is filled. There are also no limitations on the material of the container, and for example, the external use composition of the first present invention can be provided by filling into a container made of a material made of plastic or glass in the manner of polyethylene terephthalate, polyethylene naphthalate, polyarylate, polycarbonate, polyethylene or polypropylene. Polyethylene terephthalate, polyethylene naphthalate or polyarylate is particularly preferable for the material of the container.

<Production Method of External Use Composition>

There are no particular limitations on the method used to produce the external use composition of the first present invention, and can be produced by suitably selecting Component (A), an optional component as previously described and other components followed by mixing in a solvent. For example, in order to obtain a gel-like composition, it is necessary to temporarily heat the components to 60° C. to 95° C. during the aforementioned mixing followed by allowing to stand at room temperature.

The external use composition of the first present invention is an external use composition having a novel composition not found in the prior art that has a superior collagen production promoting effect and cell activating effect, and is able to suppress, improve or prevent wrinkling and sagging of the skin accompanying aging. In addition, the external use composition of the first present invention is able to suppress, improve or prevent decreases in skin resiliency and elasticity. Moreover, since Component (A) also has the action of a gelling agent, the external use composition of the first present invention can be obtained in a suitable form as necessary. As a result of having such properties, the external use composition of the first present invention can be preferably used in the field of cosmetics, quasi drugs or pharmaceuticals as an external use composition for preventing aging, an external use composition for promoting collagen production and activating cells, or as an external use composition for preventing wrinkling and sagging of the skin.

<Collagen Production Promoter>

The collagen production promoter of the first present invention comprises a lipopeptide represented by the aforementioned formula (1) or a pharmaceutically acceptable salt thereof (Component (A)). The collagen production promoter of the first present invention can suitably and arbitrarily incorporate components ordinarily used in cosmetics, quasi drugs or pharmaceuticals within a range that does not impair the collagen production promoting effect thereof. In addition, the collagen production promoter of the first present invention can also be effectively used as a composition for preventing or treating joint disorders or as a composition for preventing or treating inflammatory diseases. The explanation of Component (A) in the external use composition of the first present invention can be applied to the explanation of Component (A) contained in the collagen production promoter of the first present invention. In addition, the collagen production promoter of the first present invention can be produced by incorporating Component (A) and other components in accordance with ordinary methods. The collagen production promoter of the first present invention is able to suppress, prevent or improve wrinkling and sagging of the skin accompanying aging, and can be widely applied to a cosmetic, quasi drug or pharmaceutical used for aging care or to a drug for preventing or treating joint disorders or inflammatory diseases and the like.

<Cell Activator>

The cell activator of the first present invention comprises a lipopeptide represented by the aforementioned formula (1) or a pharmaceutically acceptable salt thereof (Component (A)). The cell activator of the first present invention can suitably and arbitrarily incorporate components ordinarily used in cosmetics, quasi drugs or pharmaceuticals within a range that does not impair the effects of the first present invention. The explanation of Component (A) in the external use composition of the first present invention can be applied to the explanation of Component (A) contained in the cell activator of the first present invention. In addition, the cell activator of the first present invention can be produced by incorporating Component (A) and other components in accordance with ordinary methods. The cell activator of the first present invention is able to suppress, prevent or improve wrinkling and sagging of the skin accompanying aging, and can be widely applied to a cosmetic, quasi drug or pharmaceutical used for aging care.

<Cosmetic>

The cosmetic of the first present invention has a collagen production promoting effect and cell activating effect. Consequently, it can be widely and preferably used as a cosmetic or cosmetic for aging care for suppressing, preventing or improving wrinkling and sagging of the skin accompanying aging.

<Quasi Drug and Pharmaceutical>

The quasi drug or pharmaceutical of the first present invention comprises the collagen production promoter or cell activator of the first present invention. Consequently, the quasi drug or pharmaceutical of the first present invention demonstrates superior collagen production promoting and cell activating effects and can be preferably used as an external use preparation. In addition, it can also be effectively used as a drug for preventing or treating joint disorders or as a drug for preventing or treating inflammatory diseases.

<Method for Promoting Collagen Production>

The first present invention includes a method for promoting production of collagen that uses Component (A) having a superior collagen production promoting effect. For example, the use of an external use composition, cosmetic or drug that incorporates Component (A) makes it possible to promote collagen production in cells that compose the skin. As a result, suppression, prevention or improvement of wrinkling and sagging of the skin accompanying aging can be realized.

Examples of First Present Invention

Although the following provides a more detailed explanation of the first present invention based on examples thereof, the first present invention is not limited to these examples.

[Preparation of External Use Composition]

External use compositions of the examples and comparative examples (test preparations) were prepared using ordinary methods in accordance with the formulations described in the following Tables 1-1 and 1-2. The units of the numerical values indicated in the tables are in percent by weight (%) unless specifically indicated otherwise. Each of the external use compositions was evaluated by subjecting to the tests indicated below.

Test Examples

<Collagen Production Test>

A collagen production test was carried out in accordance with the method indicated below using each external use composition of the comparative examples and examples prepared in accordance with the formulations described in the following Table 1-1.

The collagen production of each external use composition was tested in the manner indicated below. Normal human dermal fibroblasts (NHDF) were cultured in a 48-well culture plate. More specifically, the fibroblasts were inoculated into the plate at a density of $1.0 \times 10^4$ cells/well followed by culturing for 2 days in an environment at 37° C., 5% carbon dioxide gas and 95% air. A medium in which fetal bovine serum (FBS) was contained in Dulbecco's Modified Eagle Medium (DMEM) at a concentration of 10% by weight was used at 400 µl per well for the culture broth. Next, the medium was replaced with culture broth to which was added a small amount of FBS, namely DMEM medium containing 0.5% FBS, followed by additionally culturing for 6 hours. Subsequently, the culture broth was removed and replaced with 400 µl of DMEM medium containing 0.5% FBS in which the test samples indicated in the following Table 1-1 were dissolved at each concentration followed by continuing culturing. On the other hand, culture broth to which had been added 400 µl of DMEM medium containing 0.5% FBS without adding a test sample was used as a control. After culturing for 3 weeks, the culture broth was collected and the concentration of type I collagen that had been secreted into the culture broth was quantified by enzyme-linked immunoassay (Anti-Human Procollagen Type I C-Peptide EIA Kit, Takara Bio) followed by calculating the resulting values as the amount of collagen per cell. The amount of collagen in each test culture broth (external use composition) was then calculated based on a value of 100% for the amount of type I collagen in the control culture broth based on the results of quantification. The results are shown in Table 1-1 and FIG. 1-1.

TABLE 1-1

| | Test sample (µg/mL) | | Amount of collagen |
|---|---|---|---|
| | L-ascorbic acid | Pal-GH | production (%) |
| Comp. Ex. 1-1 (control) | 0 | 0 | 100 |
| Comp. Ex. 1-2 | 17.6 | 0 | 103 |
| Example 1-1 | 0 | 10 | 121 |

TABLE 1-1-continued

| | Test sample (μg/mL) | | Amount of collagen |
|---|---|---|---|
| | L-ascorbic acid | Pal-GH | production (%) |
| Example 1-2 | 0 | 100 | 159 |
| Example 1-3 | 17.6 | 10 | 171 |

Pal-GH: Palmitoyl dipeptide-18 (INCI nomenclature)

As shown in Table 1-1 and FIG. 1-1, the external use compositions of the examples demonstrated a collagen production promoting effect. On the basis thereof, the external use compositions of the examples were considered to have an anti-wrinkle effect.

<Growth Promotion Test of Dermal Fibroblasts>

A growth promotion test was carried out on dermal fibroblasts in accordance with the method indicated below using each of the external use compositions of the comparative examples and examples prepared in accordance with the formulations described in the following Table 1-2.

Normal human dermal fibroblasts (NHDF, CRL-2089) were cultured in a 96-well culture plate. More specifically, the fibroblasts were inoculated into the plate at a density of $1.0 \times 10^4$ cells/well followed by culturing for 24 hours in an environment at 37° C., 5% carbon dioxide gas and 95% air. A medium in which fetal bovine serum (FBS) was contained in Dulbecco's Modified Eagle Medium (DMEM) at a concentration of 10% by weight was used at 100 μl per well for the culture broth. Subsequently, the culture broth was removed and replaced with 100 μl of serum-free medium in which the test samples indicated in the following table were dissolved at each concentration followed by continuing culturing. In addition, culture broth to which had been added 100 μl of serum-free medium but to which a test sample had not been added was used as a control. After additionally culturing for 24 hours, the number of viable cells in each well was measured using the neutral red (NR) method. The percentage of viable cells (%) in each group to which test sample had been added based on a value of 100% for the number of viable cells of the control was taken to be the cell growth rate (%) based on the measurement results. The results are shown in Table 1-2 and FIG. 1-2.

TABLE 1-2

| | Test sample (μg/mL) | |
|---|---|---|
| No. | Pal-GH | Cell growth rate (%) |
| Comp. Ex. 1-3 | 0 | 100 |
| Example 1-4 | 1 | 126 |
| Example 1-5 | 10 | 115 |

Pal-GH: Palmitoyl dipeptide-18 (INCI nomenclature)

Figures 1, 2:
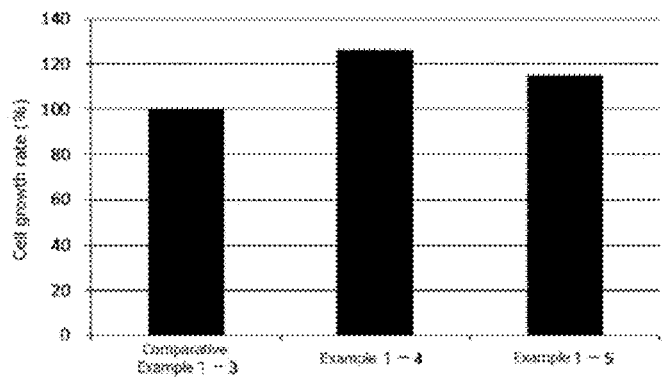

As shown in Table 1-2 and FIG. 1-2, the external use compositions of the examples demonstrated a growth promoting effect (cell activating effect) on dermal fibroblasts.

External use compositions for skin having the compositions indicated below (Formulation Examples 1-1 to 1-13) were prepared according to an ordinary method.

Formulation 1-1: Whitening Essence

TABLE 1-3

| Component | Content (%) |
|---|---|
| L-ascorbic acid | 20 |
| Diethylene glycol monoethyl ether | 30 |

TABLE 1-3-continued

| Component | Content (%) |
|---|---|
| Propylene glycol | 20 |
| Glycerin | 4 |
| Lactic acid | 1.5 |
| Iris root extract | 0.01 |
| Grapefruit extract | 0.5 |
| Glasswort extract | 0.5 |
| Fragrance | 0.1 |
| Pal-GH | 0.5 |
| Purified water | Balance |
| Total | 100 |

Formulation Example 1-2: Whitening Milky Lotion

TABLE 1-4

| Component | Content (%) |
|---|---|
| L-ascorbic acid | 20 |
| Polyglyceryl stearate | 1 |
| Ethylene glycol monoethyl ether | 40 |
| Sodium lactate | 0.1 |
| Stearyl alcohol | 1 |
| Squalane | 1 |
| Lavender oil | 0.5 |
| Chamomile extract | 0.5 |
| Sakhalin kelp extract | 0.5 |
| Pal-GH | 0.5 |
| Purified water | Balance |
| Total | 100 |

Formulation Example 1-3: Whitening Cream

TABLE 1-5

| Component | Content (%) |
|---|---|
| L-ascorbic acid | 20 |
| Ethylene glycol monoethyl ether | 30 |
| Sorbitan stearate | 0.7 |
| PEG sorbitan stearate | 1 |
| Paraffin | 5 |
| Cetanol | 2 |
| Glycerin | 3 |
| 1,3-butylene glycol | 5 |
| Allantoin | 0.1 |
| Xanthan gum | 0.1 |
| Pal-GH | 0.5 |
| Purified water | Balance |
| Total | 100 |

Formulation Example 1-4: Spray Cosmetic

TABLE 1-6

| Component | Content (%) |
|---|---|
| L-ascorbic acid | 8 |
| Diethylene glycol monoethyl ether | 50 |
| Ethanol | 10 |

TABLE 1-6-continued

| Component | Content (%) |
| --- | --- |
| Aloe extract | 0.1 |
| Pal-GH | 1 |
| Purified water | Balance |
| Total | 100 |

Formulation Example 1-5: External Skin Preparation

TABLE 1-7

| Component | Content (%) |
| --- | --- |
| L-ascorbic acid | 5 |
| Dipropylene glycol monopropyl ether | 40 |
| Polyoxyethylene sorbitan fatty acid ester | 1 |
| Jojoba oil | 5 |
| Witch hazel extract | 0.1 |
| Carboxyvinyl polymer | 0.5 |
| Triethanolamine | 0.3 |
| Pal-GH | 1 |
| Purified water | Balance |
| Total | 100 |

Formulation Example 1-6: Sunscreen

TABLE 1-8

| Component | Content (%) |
| --- | --- |
| Arbutin | 3 |
| Trimethylglycine | 1 |
| 2-ethylhexyl para-methoxycinnamate | 10 |
| Decamethylcyclopentasiloxane | 20 |
| Octyl palmitate | 10 |
| Polyoxyethylene-methylpolysiloxane copolymer | 3 |
| Methyl hydrogenpolysiloxane-treated low temperature-fired zinc oxide | 15 |
| Alkyl polyacrylate | 5 |
| Concentrated glycerin | 5 |
| Absolute ethanol | 5 |
| 1,3-butylene glycol | 3 |
| Panthenol | 0.1 |
| Fragrance | 0.1 |
| Phytic acid | 0.05 |
| Pal-GH | 0.5 |
| Purified water | Balance |
| Total | 100 |

Formulation Example 1-7: Whitening Milky Lotion

TABLE 1-9

| Component | Content (%) |
| --- | --- |
| Arbutin | 3 |
| Trimethylglycine | 2 |
| Polyglyceryl-10 isostearate | 2 |
| Polyoxyethylene hydrogenated castor oil (HCO-10) | 0.5 |
| Squalane | 5 |
| Carboxyvinyl polymer | 0.2 |
| Triethanolamine | 0.1 |
| Concentrated glycerin | 5 |
| Magnesium sulfate | 0.1 |

TABLE 1-9-continued

| Component | Content (%) |
| --- | --- |
| Sodium edetate | 0.05 |
| Methyl paraoxybenzoate | 0.2 |
| Pal-GH | 0.5 |
| Purified water | Balance |
| Total | 100 |

Formulation Example 1-8: Whitening Cream

TABLE 1-10

| Component | Content (%) |
| --- | --- |
| Arbutin | 3 |
| Trimethylglycine | 2 |
| Lauryl dimethicone polyglycerin-3 crosspolymer-glyceryl tri(2-ethylhexanoate) | 5 |
| Crosslinked methylpolysiloxane-methylpolysiloxane | 5 |
| Crosslinked alkyl-modified silicon-glyceryl tri(2-ethylhexanoate) | 3 |
| Decamethylcyclopentasiloxane | 15 |
| Polymethylsilsesquioxane | 3 |
| (Dimethicone-vinyl dimethicone-methicone) crosspolymer | 1 |
| Alkyl polyacrylate | 5 |
| Concentrated glycerin | 10 |
| Magnesium sulfate | 0.1 |
| Sodium edetate | 0.05 |
| Cyanocobalamin | 0.01 |
| Methyl paraoxybenzoate 0.05 | 0.2 |
| Pal-GH | 0.5 |
| Purified water | Balance |
| Total | 100 |

Formulation Example 1-9: Whitening Essence

TABLE 1-11

| Component | Content (%) |
| --- | --- |
| Hydroquinone | 1 |
| Diethylene glycol monoethyl ether | 30 |
| Hyaluronic acid | 0.05 |
| 1,3-butylene glycol | 50 |
| Methyl paraoxybenzoate | 0.05 |
| Pal-GH | 0.5 |
| Purified water | Balance |
| Total | 100 |

Formulation Example 1-10: Aging Care Cream

TABLE 1-12

| Component | Content (%) |
| --- | --- |
| Astaxanthin | 0.1 |
| Trimethylglycine | 0.1 |
| Pentaerythritol tetra(2-ethylhexanoate) | 5 |
| White Vaseline | 2 |
| Polyoxyethylene sorbitan stearate | 2 |
| Carboxyvinyl polymer | 0.1 |
| 1,3-butylene glycol | 5 |
| Cetanol | 0.5 |
| Concentrated glycerin | 5 |
| Cyanocobalamin | 0.01 |

TABLE 1-12-continued

| Component | Content (%) |
|---|---|
| L-arginine | 0.1 |
| Xanthan gum | 0.1 |
| Hydroxyethyl cellulose | 0.1 |
| Sodium alginate | 0.1 |
| Methyl paraoxybenzoate | 0.2 |
| Propyl paraoxybenzoate | 0.05 |
| Pal-GH | 1 |
| Purified water | Balance |
| Total | 100 |

Formulation Example 1-11: Aging Care Essence

TABLE 1-13

| Component | Content (%) |
|---|---|
| Astaxanthin | 0.5 |
| Trimethylglycine | 3 |
| Sodium ascorbate | 10 |
| Hyaluronic acid | 0.05 |
| 1,3-butylene glycol | 5 |
| Polyoxyethylene hydrogenated castor oil 80 | 1 |
| Methyl paraoxybenzoate | 0.05 |
| Pal-GH | 0.5 |
| Purified water | Balance |
| Total | 100 |

Formulation Example 1-12: Whitening Essence

TABLE 1-14

| Component | Content (%) |
|---|---|
| 3-O-ethyl ascorbic acid | 3 |
| Diethylene glycol monoethyl ether | 30 |
| Propylene glycol | 20 |
| Glycerin | 4 |
| Lactic acid | 1.5 |
| Iris root extract | 0.01 |
| Grapefruit extract | 0.5 |
| Glasswort extract | 0.5 |
| Brown algae extract | 0.1 |
| Pal-GH | 0.5 |
| Purified water | Balance |
| Total | 100 |

Formulation Example 1-13: Topical Hair Tonic

TABLE 1-15

| Component (content %) | Formulation Example 1-13-1 | Formulation Example 1-13-2 | Formulation Example 1-13-3 | Formulation Example 1-13-4 |
|---|---|---|---|---|
| Minoxidil | 0.5 | 1 | 0.1 | — |
| Resorcin | 1 | — | — | — |
| Pantothenyl ethyl ether | 0.1 | — | 0.5 | 0.2 |
| Hinokitiol | — | 0.05 | — | — |
| L-menthol | 0.01 | 0.1 | 1 | — |
| DL-camphor | — | — | — | 0.01 |
| Swertia japonica extract | 0.1 | 1 | 2 | — |
| Carrot extract | — | 0.1 | 2 | 1 |
| Tocopherol acetate | — | 0.5 | — | — |
| Dipotassium glycyrrhizate | 0.05 | — | 0.1 | 2 |
| Ethanol | 40 | 30 | 10 | — |
| Propylene glycol | 10 | — | 5 | — |
| Dipropylene glycol | — | 10 | 5 | 2 |
| Diethylene glycol monoethyl ether | — | 10 | 20 | 30 |
| Xanthan gum | — | 0.1 | — | — |
| Polyoxyethylene hydrogenated castor oil 60 | 1 | — | — | — |
| Pal-GH | 0.5 | 0.5 | 1 | 5 |
| Purified water | Balance | Balance | Balance | Balance |
| Total | 100 | 100 | 100 | 100 |

This completes the explanation of the first present invention. Continuing, an explanation of the second present invention is provided.

The Second Present Invention

The second present invention relates to an external use composition, an ophthalmic composition, antibiotics and an antibacterial method.

BACKGROUND ART

In cosmetics, the medical supplies, antibiotics and antiseptic agent are widely used to prevent the pollution of products occurring from microbes and changes in quality and to secure the preservative stability of products (cf. patent literature 2-1). Also, in cosmetics and medical supplies having antibacterial action such as antiacne, antifungus, antibiotics and antiseptic agent are used equally. For example, benzoic acid, salicylic acid, sorbic acid, dehydro acetic acid and salines thereof, paraoxybenzoic acid, para chlor meta cresol are used, in the territory of cosmetics, and in the territory of medical supplies, benzoic acid, sodium benzoate, benzalkonium chloride, benzethonium chloride, cresol, chlorobutanol, thymol are used as antibiotics and antiseptic agents. However, generally irritation is high in most of these materials, and there are toxic agents among them. Also, some agents become the allergen causing allergy to the skin or the whole body.

Thus the effort for preparing cosmetics and medical supplies comprising enough antimicrobial action without such conventional antibiotics and antiseptic agent is made. For example, a method to combine alcohol, a method to combine phenoxyethanol, a method using antibacterial polyol, and a method using the antibacterial component or extract derived from animals and plants are known. However, products may be decayed or mold may grow during use at room temperature without obtaining enough antimicrobial action by these methods in some cases.

Also, patent literature 2-2 describes about gelatinizer comprising the particular lipids peptide, but there is not the description which is specific about the external use composition using this gelatinizer, and, besides, there is neither any description nor the suggestion about these particular lipids peptide having an antimicrobial effect.

PRIOR ART DOCUMENT

Patent Literature

[patent literature 2-1] JP 2005-170854
[patent literature 2-2] WO 2010/013555

SUMMARY OF THE SECOND PRESENT INVENTION

Problem to be Solved by the Second Present Invention

With the foregoing view, the object of the second invention is to provide a mild external use composition having enough antibacterial activities, and the antibiotics used for this composition, the antibacterial method using such a new type of antibacterial component, and the ophthalmic composition object including such a new type of component.

Means for Solving Problem of the Second Present Invention

Invention to solve the problem namely the subject matter of the second present invention is as follows.
<1> An external use composition for antibacterial, comprising (A2) a lipopeptide represented by the following formula (2-1), or a pharmaceutical acceptable salt thereof (to also be referred as "Component (A2)"),

[Chemical 6]

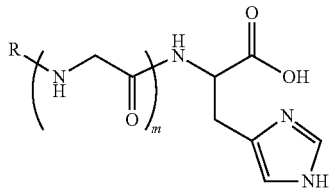

(2-1)

(wherein R represents hydrogen atom or a group represented by —C(O)R$^1$. R$^1$ represents a saturated aliphatic group, or aliphatic group having a single unsaturated bond, having 9 to 19 carbon atoms, and m is 0 or 1).
<2> The external use composition according to <1> which is for the antibacterial against an acne bacteria.
<3> The external use composition according to <1> which is for antibacterial against fungus.
<4> The external use composition according to <1> which is for the antibacterial against causative bacteria of body odor.
<5> The external use composition according to <1> which is for antibacterial or sterilization against an oral cavity.
<6> The external use composition according to <5> which is for suppressing, improving or preventing at least one kind selected from the group consisting of decayed tooth and periodontal disease.
<7> The external use composition according to <1> which is for suppressing, improving or preventing atopic dermatitis.
<8> The external use composition according to <1> which is for opthalmological use.
<9> The external use composition according to any of <1>~<8>, further comprising an antibacterial component other than Component (A2).

<10> An antibacterial agent comprising (A2) a lipopeptide represented by the following formula (2-1) or a pharmaceutically acceptable salt thereof:

[Chemical 7]

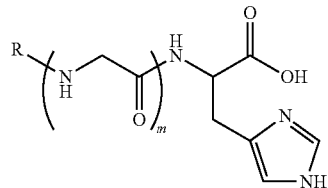

(2-1)

(wherein R represents a hydrogen atom or the group represented by —C(O)R$^1$, R$^1$ represents a saturated aliphatic group, or aliphatic group having a single unsaturated bond, having 9 to 19 carbon atoms, and m represents 0 or 1).
<11> An antibacterial method using (A2) a lipopeptide represented by the following formula (2-1)

[Chemical 8]

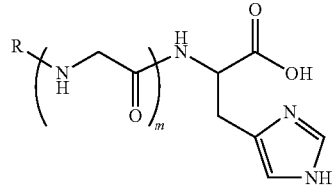

(2-1)

(wherein R is hydrogen atom or the group represented by —C(O)R$^1$. R$^1$ represents a saturated aliphatic group, or aliphatic group having a single unsaturated bond, having 9 to 19 carbon atoms, and m is 0 or 1) or the pharmaceutically acceptable salt thereof.
<12> An ophthalmic composition comprising (A2) a lipopeptide represented by the following formula (2-1)

[Chemical 9]

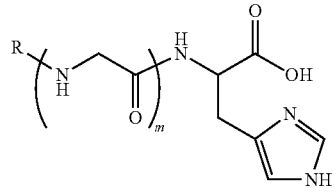

(2-1)

(wherein R is hydrogen atom or the group represented by —C(O)R$^1$. R$^1$ represents a saturated aliphatic group, or aliphatic group having a single unsaturated bond, having 9 to 19 carbon atoms, and m is 0 or 1) or the pharmaceutically acceptable salt thereof.
[The Effect Offered by the Second Present Invention]

Even if conventional antibiotics and antiseptic agent are not used or their blending amount is reduced, the external use composition of the second present invention has enough antibacterial activity by including the component (A2). Because the external use composition of the second present invention has such a characteristic, it can be widely used as cosmetics, quasi-drugs and/or medical supplies which provide antimicrobial effects and antiseptic bactericidal effects to skin disease (such as pimple, scalp eczema, eczema of the back, atopic dermatitis), oral disease (such as decayed tooth, periodontal disease, inflammation of gums), or bacteria, fungus participating in body odors.

Embodiment of the Second Present Invention

The second present invention is described in detail as follows.
<External Use Composition>
The external use composition of the second present invention includes a compound represented by the following formula (2-1) or pharmaceutically acceptable salts (Component (A2)) thereof. The external use composition of second present invention is superior in the antibacterial activity by including the Component (A2). Note that the external use composition of the second present invention may include solvents and various arbitary components other than a Component (A2) for the purpose of improving effects of the advantage offered by the second present invention. Component (A2), solvents and arbitrary components are described as follows.

Here, "the antibacterial" means the characteristic of preventing growth of specifically pathogens and/or decreasing number of organism against not only the bacteria such as acne bacteria, *Streptococcus mutans, staphylococcus aureus, Escherichia coli*, but also fungus such as *Candida* bacteria, the *Malassezia* bacteria, for example, it refers the characteristics preventing increase of number of organism and/or decreasing number of organism in comparison with control on the antimicrobial evaluation.
[Component (A2)]
Component (A2) is a compound represented by the following formula (2-1) or pharmaceutically acceptable salts thereof and includes a part comprising the peptide. Furthermore, this part comprising the peptide consists of histidine or glycinyl histidine.

[Chemical 10]

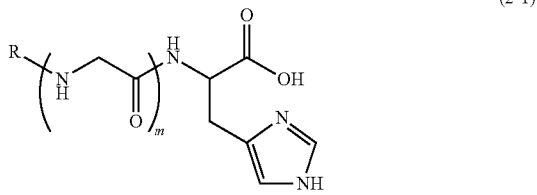

(2-1)

Wherein, R is a hydrogen atom or a group represented by —C(O)R$^1$. R$^1$ represents a saturated aliphatic group, or one aliphatic group having a single unsaturated bonding, having 9 to 19 carbon atoms, and m is 0 or 1.
In the case R is hydrogen, the compound represented by the formula (2-1) is histidine or glycinyl histidine.
In the case R represents —C(O)R$^1$, R$^1$ is preferably a saturated aliphatic group having 11 to 17 carbon atoms or an aliphatic group having a single unsaturated bond, is more preferably a saturated aliphatic group having 11 to 17 carbon atoms and is further preferably a linear saturated aliphatic group having 11 to 17 carbon atoms.
Examples of R$^1$ include a nonyl group, decanyl (capryl) group, undecanyl group, dodecanyl (lauryl) group, tridecanyl group, tetradecanyl group (myristyl group), pentadecanyl group, hexadecanyl group (palmityl group), heptadecanyl group, octadecanyl group (stearyl group), nonadecanyl group, nonenyl group, decenyl group, undecenyl group, dodecenyl group, tridecenyl group, tetradecenyl group, pentadecenyl group, hexadecenyl group, heptadecenyl group, octadecenyl group and nonadecenyl group.

Of these, from the viewpoint of antimicrobial effect of the external use composition of the second present invention, R$^1$ is preferably a tetradecanyl group (myristyl group), a hexadecanyl group (palmityl group), an octadecanyl radical (stearyl group).

Preferable examples of Component (A) in the external use composition of the first present invention in the case m is 0 include N-nonylhistidine, N-decanoylhistidine, N-undecanoylhistidine, N-lauroylhistidine, N-tridecanoylhistidine, N-myristoylhistidine, N-pentadecanoylhistidine, N-palmitoylhistidine, N-heptadecanoylhistidine, N-stearoylhistidine, N-nonadecanoylhistidine and N-eicosanoylhistidine.

In addition, examples in the case m is 1 include dipeptides in the form of glycinyl histidine, N-nonoyl glycinyl histidine, N-decanoyl glycinyl histidine, N-undecanoyl glycinyl histidine, N-lauroyl glycinyl histidine, N-tridecanoyl glycinyl histidine, N-myristoyl glycinyl histidine, N-pentadecanoyl glycinyl histidine, N-palmitoyl glycinyl histidine, N-heptadecanoyl glycinyl histidine, N-stearoyl glycinyl histidine, N-nonadecanoyl glycinyl histidine and N-icosanoyl glycinyl histidine.

Furthermore, either L-form or R-form optically active histidine can be used for the histidine moiety in Component (A2). Since the external use composition of the first present invention is preferably used in a cosmetic, quasi drug or pharmaceutical, a lipopeptide having the L-form of histidine present in the body is used particularly preferably.

Examples of pharmaceutically acceptable salts of the compound represented by the aforementioned formula (2-1) include alkaline metal salts such as lithium salts, sodium salts, potassium salts or calcium salts, while examples of salts corresponding to the imidazole group of histidine include inorganic acid salts such as hydrochlorides, sulfates or phosphates, and organic acid salts such as acetates, carbonates, citrates or succinates.

The previously explained Component (A2) can be produced according to a method commonly known among persons with ordinary skill in the art. For example, Component (A2) can be produced by linking the required amino acids by peptide solid-phase synthesis, reacting the N-terminal of the amino acid located on the end as viewed from the solid phase with the fatty acid to serve as the lipid moiety, and then forming into a salt as necessary. In addition, Component (A2) can be produced by starting from a fatty acid, linking an amino acid thereto and then forming into a salt as necessary using a liquid phase method.

One type of Component (A2) in the second present invention may be used alone or two or more types may be arbitrarily used in combination. The content of Component (A2) in the entire external use composition (in 100% by weight thereof) of the second present invention is normally 0.0001% to 5% by weight, preferably 0.0005% to 3% by weight, and more preferably 0.001% to 1.5% by weight from the viewpoint of antibacterial activity.
[Solvent]
The external use composition of the second present invention comprises water, alcohol, hydrophilic organic solvent, fatty acid, higher fatty acid ester, glyceride, hydrophobic organic solvent or mixed solvent miscible therewith. When Component (A2) is added to these solvents at a specific ratio, gelling occurs and an external use composition can be obtained that has suitable viscosity and favorably works into to skin.

The preferable solvent functions as a base or carrier in the external use composition, and examples thereof include aqueous solvents such as water, hydrocarbons in the manner of liquid paraffin, squalane, Vaseline, gelling hydrocarbons (such as plastibase), ozokerite, α-olefin oligomers or light liquid paraffin, silicone oils in the manner of methylpolysiloxanes such as poly(methylsilsesquioxane), crosslinked methyl polysiloxane, highly polymerized methyl polysiloxane, cyclic silicone, alkyl-modified silicone, crosslinked alkyl-modified silicone, amino-modified silicone, polyether-modified silicone, polyglycerin-modified silicones such as lauryl dimethicone polyglycerin-3 crosspolymer, cross-linked polyether-modified silicone, crosslinked alkyl polyether-modified silicone, silicone-alkyl chain-co-modified polyether-modified silicone, silicone-alkyl chain-co-modified polyglycerin-modified silicone, polyether-modified branched silicone, polyglycerin-modified branched silicone, acrylsilicone, phenyl-modified silicone or silicon oil such as silicone resin, higher alcohols in the manner of cetanol, cetostearyl alcohol, stearyl alcohol or behenyl alcohol, cellulose derivatives in the manner of ethyl cellulose, hydroxypropyl cellulose or hydroxypropyl methyl cellulose, polyvinylpyrrolidone, carrageenan, polyvinylbutyrate, polyethylene glycol, dioxane, butylene glycol polyester adipate, esters in the manner of isopropyl myristate, octyldodecyl myristate, isopropyl palmitate, cetyl palmitate, octyl palmitate, isononyl isononanoate, pentaerythritol tetra(2-ethylhexanoate), glyceryl tri(2-ethylhexanoate) or jojoba oil, polysaccharides in the manner of dextrin or maltodextrin, and alcohols in the manner of ethanol or isopropanol. Among these, aqueous solvents are preferable and water is particularly preferable.

In the case the external use composition of the second present invention comprises water, although the amount incorporated therein can be suitably selected in consideration of the feel on the skin during use and the effects of the first present invention, it is, for example, 0.001% to 99.5% by weight, preferably 0.01% to 90% by weight, more preferably 0.1% to 60% by weight and most preferably 1% to 20% by weight based on the total weight of the external use composition of the first present invention.

[Arbitrary Component]

For the purpose of improving the advantage offered by the second present invention, the external use composition of the second present invention can further include at least one kind of component selected from the group consisting of vitamins, 1,2-alkanediol, sterilizer, polyhydric alcohol, glycol ether, a cluster comprising the thickener in addition to the Component (A2). Note that these compounds may be used in one kind alone, respectively, and may also use optionally in combination two kinds or more. Also, as well as these, other components may be used as far as the effects of the second present invention is not lost. Note that in the event a compound exemplified as each component specifically repeats, either component should include.

(Vitamins)

Examples of the aforementioned vitamins include vitamin A compounds such as retinol, retinol derivatives such as retinol acetate or retinol palmitate, retinal, retinoic acid, methyl retinoate, ethyl retinoate, retinol retinoate, d-δ-tocopheryl retinoate, α-tocopheryl retinoate or β-tocopheryl retinoate, provitamin A compounds such as β-carotene, α-carotene, γ-carotene, δ-carotene, lycopene, zeaxanthin, cryptoxanthin or echinenone, vitamin E compounds such as δ-tocopherol, α-tocopherol, β-tocopherol, dl-α-tocopherol succinate, calcium dl-α-tocopherol succinate, δ-tocopherol or tocopherol nicotinate, vitamin B2 compounds such as riboflavin, flavin mononucleotide, flavin adenine dinucleotide, riboflavin butyrate, riboflavin tetrabutyrate, riboflavin 5'-phosphate sodium or riboflavin tetranicotinate, nicotinic acids such as methyl nicotinate, nicotinic acid or nicotinic acid amide, vitamin C compounds such as ascorbyl stearate, L-ascorbyl dipalmitate, ascorbyl tetraisopalmitate (ascorbyl tetra-2-hexyldecanoate), ascorbic acid, sodium ascorbate, dehydroascorbic acid, sodium ascorbyl phosphate, magnesium ascorbyl phosphate, ascorbyl glucoside or 3-O-ethyl ascorbic acid, vitamin D compounds such as methyl hesperidin, ergocalciferol or cholecalciferol, vitamin K compounds such as phylloquinone or farnoquinone, vitamin B1 compounds such as dibenzoylthiamine, dibenzoylthiamine hydrochloride, thiamine hydrochloride, thiamine cetyl hydrochloride, thiamine thiocyanate, thiamine lauryl hydrochloride, thiamine nitrate, thiamine monophosphate, thiamine diphosphate, thiamine triphosphate, thiamine monophosphate ester phosphate, thiamine monophosphate ester, thiamine diphosphate ester, thiamine triphosphate ester hydrochloride, thiamine triphosphate ester or thiamine triphosphate ester monophosphate, vitamin B6 compounds such as pyridoxine hydrochloride, pyridoxine acetate, pyridoxal hydrochloride, pyridoxal 5'-phosphate or pyridoxamine hydrochloride, vitamin B12 compounds such as cyanocobalamin, hydroxocobalamin or deoxyadenosylcobalamin, folic acid compounds such as folic acid or pteroylglutamic acid, pantothenates such as pantothenic acid, calcium pantothenate, pantothenyl alcohol (panthenol), D-pantetheine, D-pantethine, coenzyme A or pantothenyl ethyl ether, biotins such as biotin or biocytin, and other vitamin-like agents such as carnitine, ferulic acid, α-lipoic acid, orotic acid or γ-oryzanol.

Of these, from the point of view which the antimicrobial effect of the external use composition of second present invention is high, vitamin C is preferable. Note that the some of vitamin C derivatives among vitamin C group is converted into vitamin C in vivo by an enzyme and acts. For example, the ascorbic acid glucoside is decomposed into ascorbic acid and glucose in vivo, and it is thought that ascorbic acid plays an antimicrobial effect.

If a vitamin group is combined, the used amount can be selected in consideration of usability appropriately, but, to the whole of the external use composition of the second present invention, for example, it is 0.001-30% by weight, preferably 0.1-25% by weight, more preferably 0.5-20% by weight.

(1,2-Alkanediol)

The external use composition of the second present invention is able to stabilize the antibacterial activity thereof by comprising a 1,2-alkanediol. Examples of 1,2-alkanediols used in the second present invention include 1,2-alkanediols represented by formula (2-2) indicated below.

$$R^2\text{—CH(OH)—CH}_2\text{—OH} \quad (2\text{-}2)$$

In the above formula, $R^2$ represents an alkyl group having 2 to 8 carbon atoms. The alkyl group may be linear or branched.

Examples of the 1,2-alkanediol contained in the external use composition of the second present invention include 1,2-butanediol, 1,2-pentanediol, 1,2-hexanediol, 1,2-heptanediol, 1,2-octanediol and 1,2-decanediol. Among these, 1,2-hexanediol and 1,2-octanediol are preferable, and 1,2-octanediol is more preferable.

The content of 1,2-alkanediol in the entire external use composition (100% by weight) of the second present invention is preferably 0.01% to 15% by weight and more preferably 0.1% to 10%/o by weight from the viewpoint of stabilizing antibacterial activity.
(Sterilizer)

The external use composition of the second present invention can improve the antibacterial effect by further including the sterilizer except the Component (A2) as an antibacterial component except the Components (A2). The sterilizer as such as, but should not be limited to, quaternary ammonium salt-type sterilizer, represented by the following formula (2-3) may be used.

[Chemical 11]

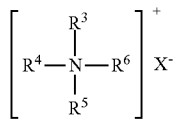

(2-3)

In formula (3) above, $R^3$ and $R^4$ respectively and independently represent an alkyl group having 1 to 3 carbon atoms. $R^5$ represents a group represented by the following formula (4). $R^6$ represents an alkyl group or alkenyl group having 1 to 4 carbon atoms. $X^-$ represents a chloride ion or bromide ion.

[Chemical 12]

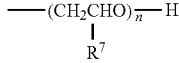

(2-4)

In formula (4) above, $R^7$ represents an alkyl group having 1 to 4 carbon atoms. n represents an integer of 3 to 60.

The aforementioned $R^7$ is preferably a methyl group and n is preferably an integer of 9 to 41. Preferable examples of the quaternary ammonium salt-based disinfectant contained in the external use composition of the first present invention include those in which $R^5$ in the aforementioned formula (3) is a polyoxypropylene group that is a polymer having 9 to 41 oxypropylene units, such as polyoxypropylene (9) methyl diethyl ammonium chloride, polyoxypropylene (25) methyl diethyl ammonium chloride or polyoxypropylene (40) methyl diethyl ammonium chloride. Examples of commercially available products thereof include Emcol CC-9, CC-36 and CC-42 manufactured by Witco Chemical Company, and Adekacol EC-CC-9, EC-CC-36 and EC-CC=42 manufactured by Asahidenka Kogyo (Corp). Moreover, other preferable examples include cetylpyridinium chloride, benzalkonium chloride and benzethonium chloride.

Among these quaternary ammonium salt-based disinfectants, cetylpyridinium chloride, benzalkonium chloride and benzethonium chloride are preferable from the viewpoints of antibacterial activity and safety.

Note that because the external use composition of the second present invention has a superior antibacterial effect by including the Component (A2), in small quantities, the quaternary ammonium salt-type sterilizer is enough as necessary, but there is not specifically the limit. It is used in (in 100% by weight) the density of 0.001%-0.5% by weight among total external use compositions of the second present invention.

The external use composition of the second present invention can contain a poorly water-soluble active disinfectant as a disinfectant component in addition to Component (A2). Here, a poorly water-soluble active disinfectant refers to a substance demonstrating both bactericidal and bacteriostatic action and having solubility in water at 25° C. of less than 1% by weight (w/v). These poorly water-soluble active disinfectants are broadly classified into phenol-based substances and alcohol-based substances.

Examples of phenol-based substances include triclosan, trichlorocarbanilide, methylparaben, ethylparaben, propylparaben and isopropyl methylphenol. Examples of alcohol-based substances include dodecyl alcohol and decyl alcohol.

The poorly water soluble active disinfectant may be composed of a single substance, may be composed by mixing a plurality of phenol-based substances, may be composed by mixing a plurality of alcohol-based substances, or may be composed by mixing a phenol-based substance and an alcohol-based substance.

Note that because the external use composition of the second present invention has superior antibacterial effect by including the Component (A2), as necessary, the water-insolubility activity sterilizer is enough in small quantities and is used in the density of 0.001-0.5% by weight among total external use compositions of the second present invention (in 100% by weight).

Disinfectants used as disinfectants of cosmetics, quasi drugs or pharmaceuticals can be used without restriction as other disinfectants. Examples thereof include sulconazole nitrate, luliconazole, miconazole, amorphin hydrochloride, clotrimazole, ketoconazole, bifonazole, neticonazole chloride, lanoconazole, liranaflate, efinaconazole, dequalinium chloride, chlorhexidine hydrochloride, chlorhexidine gluconate, alkyldiaminoethylglycine hydrochloride, cetylpyridinium chloride, sodium benzoate, chlorobutanol, salicylic acid, gluconic acid, thymol, hexachlorophene, berberine, terbinafine hydrochloride, butenafine hydrochloride, lysozyme chloride, salicylic acid, salicylate, sulfur or sulfur compounds, hinokitiol, triclosan, trichlorocarbanilide, halocarbon, chlorphenesin, sorbic acid, potassium sorbate, sodium dehydroacetate, methyl paraoxybenzoate, ethyl paraoxybenzoate, propyl paraoxybenzoate, butyl paraoxybenzoate, oxyquinoline sulfate, phenethyl alcohol, benzyl alcohol and biguanide compounds.

Among these other disinfectants, methyl paraoxybenzoate, ethyl paraoxybenzoate, propyl paraoxybenzoate, butyl paraoxybenzoate, dequalinium chloride, chlorhexidine hydrochloride, chlorhexidine gluconate, cetylpyridinium chloride and thymol are preferable from the viewpoints of antibacterial activity and safety. Furthermore, since the external use composition of the second present invention demonstrates superior antibacterial activity as a result of comprising Component (A2), disinfectant is only required to be contained in a small amount as is necessary, and is used at a concentration of 0.0001% to 1% by weight in the entire external use composition (100% by weight) of the second present invention.
(Polyvalent Alcohol)

The external use composition of the second present invention can contain polyvalent alcohol. A polyvalent alcohol used as polyvalent alcohol in cosmetics, quasi drugs or pharmaceuticals can be used without restriction as the polyvalent alcohol used in the external use composition of the second present invention. Examples thereof include glycols (such as ethylene glycol, diethylene glycol, propylene glycol, isopropylene glycol, dipropylene glycol, polypropylene glycol, polyethylene glycol, 1,3-butylene glycol or pentylene glycol), glycerin, diglycerin, triglycerin, polyglycerin, sorbitol and alkanediols (such as propanediol, 3-methyl-1,3-butanediol or pentanediol). Among these, propylene glycol, dipropylene glycol, 1,3-butylene glycol, pentylene glycol, glycerin, diglycerin, sorbitol and alkanediols (propanediol, pentanediol and hexanediol) are preferable from the viewpoints of formulating in consideration of feel on the skin during use, while dipropylene glycol, 1,3-butylene glycol and pentylene glycol are more preferable. One type of these polyvalent alcohols can be used alone or two or more types can be used in combination.

The content of polyvalent alcohol is preferably 0.01% by weight or more, more preferably 0.1% by weight or more, and even more preferably 0.5% by weight or more in the entire external use composition (100% by weight) of the second present invention. In addition, the content of polyvalent alcohol in the entire external use composition (100% by weight) of the second present invention is preferably 99.9% by weight or less, more preferably 75% by weight or less and even more preferably 50% by weight or less. If within the aforementioned ranges, moisture retention and a favorable feel on the skin during use can be imparted to the external use composition in addition to the effects of the second present invention.

(Glycol Ether)

The external use composition of the second present invention can further contain glycol ether. A glycol ether used as glycol ether in cosmetics, quasi drugs or pharmaceuticals can be used without restriction as the glycol ether used in the external use composition of the second present invention. Examples thereof include ethylene glycol-based glycol ethers in the manner of ethylene glycol monomethyl ether, ethylene glycol monoethyl ether and ethylene glycol monopropyl ether, diethylene glycol-based glycol ethers in the manner of diethylene glycol monomethyl ether, diethylene glycol monoethyl ether and diethylene glycol monopropyl ether, propylene glycol-based glycol ethers in the manner of propylene glycol monoethyl ether and propylene glycol monopropyl ether, and dipropylene glycol-based glycol ethers in the manner of dipropylene glycol monoethyl ether and dipropylene glycol monopropyl ether. Among these, ethylene glycol-based glycol ethers and diethylene glycol-based glycol ethers are preferable, ethylene glycol monomethyl ether and diethylene glycol monoethyl ether are more preferable, and diethylene glycol monoethyl ether is particularly preferable. One type of these glycol ethers can be used alone or two or more types can be used in combination.

The content of glycol ether in the entire external use composition (100% by weight) of the second present invention is preferably 0.01% by weight or more, more preferably 0.1% by weight or more and even more preferably 0.5% by weight or more. In addition, the content of glycol ether in the entire external use composition (100%/o by weight) of the second present invention is preferably 97% by weight or less, more preferably 50% by weight or less and even more preferably 30% by weight or less. If within the aforementioned ranges, moisture retention and a favorable feel on the skin during use can be imparted to the external use composition in addition to the effects of the second present invention.

(Thickener)

The external use composition of the second present invention can further contain a thickener. As a result, an external use composition that demonstrates favorable adaptability with skin and superior feel on the skin during use can be obtained.

A thickener used as a thickener of a cosmetic, quasi drug or pharmaceutical can be used without restriction for the thickener used in the external use composition of the first present invention. Examples thereof include agar, gellan gum, gua gum, locust bean gum, carrageenan, xanthan gum, dextran, methyl cellulose, ethyl cellulose, carboxymethyl cellulose, hydroxymethyl cellulose, hydroxyethyl cellulose, hydroxypropyl cellulose, hydroxypropyl methyl cellulose, carboxymethyl cellulose, carboxyethyl cellulose, sodium alginate, propylene alginate glycol ester, dextran, polyvinyl alcohol, polyvinylpyrrolidone, polyvinyl methyl ether, carboxyvinyl polymer, acrylic acid-alkyl methacrylate copolymer, sodium polyacrylate, polyethylene glycol, bentonite, dextrin fatty acid ester, pectin, hydroxyethyl acrylate-sodium acryloyldimethyl taurate copolymer, dimethyl distearyl ammonium hectorite, ammonium acryloyldimethyl taurate-vinylpyrrolidone copolymer, ammonium acryloyldimethyl taurate-beheneth-25 methacrylate crosspolymer ammonium acryloyldimethyltaurate-steareth-25 methacrylate crosspolymer, polyethylene glycol distearate, ethylene glycol triisostearate and polyoxyethylene (20) triisostearate methyl glucoside. Among these, methyl cellulose, ethyl cellulose, hydroxyethyl cellulose, hydroxymethyl cellulose, hydroxypropyl cellolose, hydroxypropyl methyl cellulose, carboxymethyl cellulose, carboxyethyl cellulose, xanthan gum, acrylic acid-alkyl methacrylate copolymer, hydroxyethyl acrylate-sodium acryloyldimethyl taurate copolymer and ammonium acryloyldimethyl taurate-vinylpyrrolidone copolymer are more preferable. One type of these thickeners may be used alone or two or more types may be used in an arbitrary combination.

The content of thickener in the entire external use composition (100% by weight) of the second present invention is preferably 0.0001% to 20% by weight, more preferably 0.001% to 10% by weight and even more preferably 0.05% to 5% by weight. If the content of thickener is within the aforementioned ranges, an external use composition can be obtained that demonstrates favorable adaptability with skin and superior feel on the skin during use.

(Other Components)

The external use composition of the second present invention may incorporate one type or a combination of two or more types of various other optional components in addition to the components described above in order to add other useful effects, examples of which include an ultraviolet scattering component, ultraviolet absorbing component, component having action that prevents and/or repairs damaged DNA, whitening component, anti-inflammatory component, cell activating component, astringent component, antioxidant component, anti-aging component, moisturizing component, keratin softening component, circulation promoting component, sebaceous matter absorbing component, hair growth component, antihistamine component, anti-inflammatory analgesic component, antipruritic component or local anesthetic component. Any arbitrary component able to be used in the pharmaceutical, quasi drug and cosmetic fields can be suitably selected and used for each of these components without any particular limitations. In addition, components corresponding to a plurality of the components indicated below can be added as components having an arbitrary effect thereof.

Examples of the aforementioned ultraviolet scattering component include inorganic compounds such as zinc oxide, titanium oxide, iron oxide, cerium oxide, zirconium oxide, titanium silicate, zinc silicate, silicic anhydride, cerium silicate or hydrated silicic acid, ultraviolet scattering components obtained by coating these inorganic compounds with an inorganic powder such as hydrated silicic acid, aluminum hydroxide, mica or talc, ultraviolet scattering components obtained by compounding into a resin powder such as polyamide, polyethylene, polyester, polystyrene or nylon, and ultraviolet scattering components obtained by treating these inorganic compounds with silicone oil or fatty acid aluminum salts. Among these, inorganic compounds such as zinc oxide, titanium oxide or iron oxide, and these inorganic compounds coated with an inorganic powder, such as aluminum hydroxide, hydrated silicic acid, mica or talc, or silicone oil are preferable.

In the case of incorporating an ultraviolet scattering component, although the amount used thereof can be suitably selected in consideration of the feel on the skin during use and the effect thereof, the amount used is, for example, 0.001% to 35% by weight and preferably 1% to 25% by weight based on the total weight of the external use composition of the first present invention.

Examples of the aforementioned ultraviolet absorbing component include 2-ethylhexyl para-methoxycinnamate, hexyl 2-[4-(diethylamino)-2-hydroxybenzoyl]benzoate, 2,4,6-tris[4-(2-ethylhexyloxycarbonyl)anilino]-1,3,5-triazine, 2-ethylhexyl dimethoxybenzylidene oxoimidazolidine propionate and 2,4-bis[{4-(2-ethylhexyloxy)-2-hydroxy}-phenyl]-6-(4-methoxyphenyl)-1,3,5-triazine.

In the case of incorporating an ultraviolet absorbing component, although the amount used thereof can be suitably selected in consideration of the feel on the skin during use and the effect thereof, the amount used is, for example, 0.01% to 20% by weight and preferably 0.1% to 15% by weight based on the total weight of the external use composition of the first present invention.

Examples of the aforementioned whitening component include hydroquinone, placenta extract, arbutin, kojic acid, ellagic acid, phytic acid, tranexamic acid, 4-n-butylresorcinol, chamomile extract, and vitamins such as vitamin A and derivatives thereof or pantothenic acid and derivatives thereof. Moreover, a plant component having whitening action may also be used as a whitening component, and examples of such plant components include components derived from iris, almond, aloe, ginkgo, oolong tea, rose fruit, scutellaria root, coptis, St. John's wort, deadnettle, kelp, pueraria root, gardenia, sophora root, chlorella, gallnut wheat, rice, rice germ, oryzanol, rice bran, asiasarium root, pepper, perilla, peony, cnidium, mulberry bark, soybean, fermented soybean, angelica root, calendula, garlic, witch hazel, safflower, moutan bark, coix, angelica root, amethyst, gambir, bracken fern, Buddhist pine, hackberry, persimmon (Dispyros kaki), catalpa, black soybean, gentian, scrophularia, sarsaparilla, green bean, windmill palm, sage, peucedanum root, radish, azalea, bush clover, barrenwort, bitterwood, parsley, holly, hop, leafy lespedeza, clove, licorice and grapefruit. Preferable examples include components derived from iris, aloe, ginkgo, oolong tea, rose fruit, scutellaria root, coptis, St. John's wort, deadnettle, kelp, pueraria root, gardenia, sophora root, gallnut, wheat, rice, rice bran, asiasarium root, pepper, perilla, peony, cnidium, mulberry bark, tea, angelica root, pot marigold, witch hazel, safflower, moutan bark, coix, amethyst, gambir, hackberry, persimmon (Dispyros kaki), catalpa, black soybean, gentian, sarsaparilla, green bean, windmill palm, sage, peucedanum root, radish, azalea, bush clover, barrenwort, bitterwood, parsley, holly, hop, clove, licorice, grapefruit and angelica root, while more preferable examples include components derived from iris, aloe, ginkgo, rose fruit, scutellaria root, coptis, St. John's wort, gardenia, sophora root, rice, rice bran, asiasarium root, peony, cnidium, mulberry bark, tea, angelica root, pot marigold, witch hazel, safflower, moutan bark, amethyst, gambir, hackberry, persimmon (Dispyros kaki), sage, radish, azalea parsley, hop, licorice, grapefruit and coix. Among these, an iris-derived component in the form of iris root extract and kelp-derived components in the form of brown algae extract or sugar kelp extract, and aloe extract are more preferable.

In the case of using these plant components in the external use composition of the first present invention, although there are no particular limitations on the form the plant components, the plant components are normally used in the form of a plant extract or essential oil thereof. Furthermore, terms indicated in parentheses in the descriptions of the aforementioned plant components refer to the scientific name, alternative name or herbal medicine name of that plant. In the case of incorporating a whitening component as explained above in the external use composition of the first present invention, although the amount used thereof can be suitably selected in consideration of the feel on the skin during use and effect thereof, the amount used is, for example, 0.0003% to 10% by weight and preferably 0.01% to 5% by weight based on the total weight of the external use composition. In the case of using a plant extract, the amount used as the amount of extract is 0.00001% to 20% by weight, preferably 0.0001% to 15% by weight and more preferably 0.001% to 10% by weight based on the total weight of the external use composition.

Examples of the aforementioned anti-inflammatory component include allantoin, calamine, tranexamic acid, glycyrrhizic acid, derivatives thereof or salts thereof, glycyrrhetic acid, derivatives thereof or salts thereof, zinc oxide, guaiazulene, tocopherol acetate, pyridoxine hydrochloride, menthol, camphor, terpene oil, indomethacin, and salicylic acid or derivatives thereof. Preferable examples include glycyrrhizic acid, derivatives thereof or salts thereof (such as dipotassium glycyrrhizate, glycyrrhetic acid, derivatives thereof or salts thereof and zinc oxide. In the case of incorporating an anti-inflammatory component, although the amount used thereof can be suitably selected in consideration of the feel on the skin during use and the effect thereof, the amount used is, for example, 0.0003% to 10% by weight and preferably 0.01% to 5% by weight based on the total weight of the external use composition of the first present invention.

Examples of the aforementioned cell activating component include amino acids such as γ-aminobutyric acid or ε-aminocaproic acid, α-hydroxy acids such as glycolic acid or lactic acid, tannin, flavonoids, saponin, allantoin and photosensitizer 301. In the case of incorporating a cell activating component, although the amount used thereof can be suitably selected in consideration of feel on the skin during use and the effect thereof, the amount used is, for example, 0.0003% to 10% by weight and preferably 0.01% to 5% by weight based on the total weight of the external use composition of the first present invention.

Examples of the aforementioned astringent component include metal salts such as alum, aluminum chlorohydrate, aluminum chloride, allantoin aluminum salt, zinc sulfate or potassium aluminum sulfate, and organic acids such as tannic acid, citric acid, lactic acid or succinic acid.

In the case of incorporating an astringent component, although the amount used thereof can be suitably selected in consideration of the feel on the skin during use and the effect thereof, the amount used is, for example, 0.0003% to 10% by weight and preferably 0.01% to 5% by weight based on the total weight of the external use composition of the first present invention.

Examples of the aforementioned antioxidant component include butylhydroxyanisole, dibutylhydroxytoluene, sodium hydrogen sulfite, sodium pyrosulfite, flavonoids, glutathione, glutathione peroxidase, glutathione-S-transferase, catalase, superoxide dismutase, thioredoxin, taurine, thiotaurine, hypotaurine, L-cysteine hydrochloride and astaxanthin. In the case of incorporating an antioxidant component, although the amount used thereof can be suitably selected in consideration of the feel on the skin during use and the effect thereof, the amount used 0.00001% to 10% by weight, preferably 0.0001% to 5% by weight and more preferably 0.001% to 5% by weight based on the total weight of the external use composition of the first present invention.

Examples of the aforementioned anti-aging component include pangamic acid, ursolic acid, turmeric extract, sphingosine derivatives, silicon, silicic acid, N-methyl-L-serine and mevalonolactone. In the case of incorporating an anti-aging component, although the amount used thereof can be suitably selected in consideration of the feel on the skin during use and the effect thereof, the amount used is, for example, 0.0003% to 10% by weight and preferably 0.01% to 5% by weight based on the total weight of the external use composition of the first present invention.

Examples of the aforementioned moisturizing component include amino acids such as alanine, serine, leucine, isoleucine, threonine, glycine, trimethylglycine, proline, hydroxyproline, glucosamine, theanine and derivatives thereof, polyvalent alcohols such as glycerin, sugar-alcohols such as sorbitol, phospholipids such as lecithin or hydrogenated lecithin, NMF-derived components such as lactic acid, sodium pyrrolidone carboxylate or urea, and vegetable oil-derived components such as lavender oil or glasswort extract. In the case of incorporating a moisturizing component, although the amount used thereof can be suitably selected in consideration of feel on the skin during use and the effect thereof, the amount used is, for example, 0.1% to 10% by weight and preferably 0.5% to 5% by weight based on the total weight of the external use composition of the first present invention.

Examples of the aforementioned keratin softening component include lanolin, urea, phytic acid, lactic acid, lactate, glycolic acid, salicylic acid, malic acid and citric acid.

In the case of incorporating a keratin softening component, although the amount used thereof is suitably selected in consideration of the feel on the skin during use and the effect thereof, the amount used is, for example, 0.0001% to 50% by weight, preferably 0.001% to 50% by weight and more preferably 0.05% to 25% by weight based on the total weight of the external use composition of the first present invention.

Examples of the aforementioned circulation promoting component include components derived from vegetable (such as Asian ginseng, Angelica keiskei, mountain arnica, gingko, fennel, Isodonis japonicus, Dutch oak, chamomile, Roman chamomile, Daucus carota sativa, gentian, burdock, rice, Japanese hawthorn, shiitake mushroom, English hawthorn, juniper, cnidium, thyme, clove, citrus unshiu, angelica root, peach kernel, spruce, carrot, garlic, butcher's broom, grape, peony, horse chestnut, lemon balm, yuzu, coix, rosemary, rose hip, citrus unshiu, angelica, spruce, peach, apricot, walnut or corn), tocopherol nicotinate, glucosyl hesperidin and hesperidin.

In the case of incorporating a circulation promoting component, although the amount used thereof can be suitably selected in consideration of the feel on the skin during use and the effect thereof, the amount used is, for example, 0.00001% to 10% by weight, preferably 0.0001% to 5% by weight, and more preferably 0.001% to 5% by weight based on the total weight of the external use composition of the first present invention. The amount used in the case of using a component derived from a vegetable as the amount of extract and the like is 0.00001% to 20% by weight, preferably 0.0001% to 15% by weight and more preferably 0.001% to 10% by weight based on the total weight of the external use composition.

Examples of the aforementioned sebaceous matter adsorbing component include talc, mica, hydroxyapatite, zinc oxide and aluminum silicate. Among these, mica, hydroxyapatite and zinc oxide are preferable, while mica is particularly preferable. In the case of incorporating a sebaceous matter adsorbing component, although the amount used thereof can be suitably selected in consideration of the feel on the skin during use and the effect thereof, the amount used is, for example, 0.001% to 35% by weight and preferably 0.1% to 25% by weight based on the total weight of the external use composition of the first present invention.

Examples of the aforementioned hair growth component include procyanidin, dipotassium glycyrrhizate, carpronium chloride, cepharanthine, menthol, hinokitiol, L-hydroxyproline, acetyl hydroxyproline, fucoidan, capsicum tincture, cepharanthine, swertiamarin, panax ginseng, flavonosteroid, minoxidil, FGF-10, Isodonis japonicus extract, Swertia herb extract, ribbon weed extract, five-leaf ginseng extract, St. John's wort extract, gentian extract, sage extract, peppermint extract, hop extract, coix extract, persimmon leaf extract, rehmannia root extract, carrot extract, Bohdi tree extract, moutan bark extract and tree bark extract.

For examples of the antihistaminic component, ethanol amine compounds such as diphenhydramine, diphenhydramine hydrochloride and dimenhydrinate; propyl amine compounds such as the chlorpheniramine maleate; phenothiazine such as promethazine hydrochloride; piperazine compounds such as the hydroxyzine; pyperidine compounds such as cyproheptadine hydrochloride can be exemplified. Moreover, epinastine hydrochloric acid, loratadine hydrochloric acid, and fexofenadine, are also exemplified. In addition, the pharmaceutically acceptable salt of each compound can be used as well as hydrochloride. Of these, diphenhydramine, diphenhydramine hydrochloride, chlorpheniramine and maleate are preferable.

Examples of the aforementioned antiphlogistic analgetic components include indomethacin, felbinac, ibuprofen, ibuprofen piconol, bufexamac, flufenamic acid butyl, bendazac, piroxicam, and ketoprofen.

Examples of the antipruritic components include crotamiton, chlorpheniramine, chlorpheniramine maleate, diphenhydramine, diphenhydramine hydrochloride, diphenhydramine salicylate, 4-hydroxy-3-methoxybenzyl nonylic acid amide, mequitazine, camphor, thymol, eugenol, polyoxyethylene lauryl ether, and perilla extract.

Examples of the local anesthesia components include lidocaine, lidocaine hydrochloride, dibucaine, dibucaine hydrochloride, ethyl aminobenzoate, eucalyptus oil, eugenol, and chlorobutanol.

In addition, the external use composition of the second present invention may also suitably incorporate components ordinarily used in the fields of pharmaceuticals, quasi drugs and cosmetics corresponding to the application or drug form thereof in addition to each of the aforementioned components. There are no particular limitations on components that can be incorporated, and examples of additives that can be incorporated include a surfactant, preservative, pH adjuster, chelating agent, stabilizer, irritation reducing agent, colorant, dispersant and fragrance. Furthermore, one type of these components can be incorporated alone or two or more types can be arbitrarily combined. In addition, the amounts used thereof can be suitably determined within a range extending from the range of the prior art that does not impair the effects of the second present invention.

Examples of the aforementioned surfactant include various types of nonionic surfactants in the manner of sorbitan esters such as sorbitan stearate, PEG sorbitan stearate, sorbitan monooleate, sorbitan monoisostearate and sorbitan monolaurate, POE-sorbitan monooleate, polyoxyethylene hydrogenated castor oil (HCO-10), glycerin fatty acid esters such as glycerin monooleate, glycerin monostearate or glycerin monomyristate, glycerin alkyl ethers such as monoisostearyl glyceryl ether or monomyristyl glyceryl ether, and polyglycerin fatty acid esters such as polyglyceryl stearate, polyglyceryl-10 isostearate, diglyceryl monostearate, decaglyceryl decastearate, decaglyceryl decaisostearate or diglyceryl diisostearate, and naturally derived surfactants such as lecithin, hydrogenated lecithin, saponin, surfactin sodium salt, cholesterol or bile acid.

Examples of the aforementioned preservative include benzoic acid, sodium benzoate, dehydroacetic acid, sodium dehydroacetate, isobutyl paraoxybenzoate, isopropyl paraoxybenzoate, butyl paraoxybenzoate, ethyl paraoxybenzoate, propyl paraoxybenzoate, benzyl paraoxybenzoate, methyl paraoxybenzoate and phenoxyethanol.

Examples of the aforementioned pH adjuster include inorganic acids (such as hydrochloric acid or sulfuric acid), organic acids (such as lactic acid, sodium lactate, citric acid, sodium citrate, succinic acid or sodium succinate), inorganic bases (such as potassium hydroxide or sodium hydroxide), and organic bases (such as triethanolamine, diisopropanolamine or triisopropanolamine).

Examples of the aforementioned chelating agent include ethylenediamine tetraacetic acid (edetic acid), ethylenediamine tetraacetate (such as sodium salt (sodium edetate: Japanese Pharmacopeia, EDTA-2Na) or potassium salt), phytic acid, gluconic acid, polyphosphoric acid or metaphosphoric acid. Among these, sodium edetate is preferable.

Examples of the aforementioned stabilizer include magnesium sulfate, sodium polyacrylate, dibutylhydroxytoluene and butylhydroxyanisole.

Examples of the aforementioned irritation reducing agent include licorice extract, gum arabic, polyvinylpyrrolidone and sodium alginate.

Examples of the aforementioned colorant include inorganic pigments and natural pigments.

Examples of the aforementioned dispersant include sodium pyrophosphate, sodium hexametaphosphate, polyvinyl alcohol, polyvinylpyrrolidone, methyl vinyl ether-maleic anhydride copolymer and organic acids.

[pH]

Although the external use composition of the second present invention may normally be provided with liquidity and have a pH of 2.0 to 9.0, pH is preferably 3.0 to 8.5 and more preferably 3.5 to 8.0 from the viewpoints of reduced irritation of the skin and mucous membranes and favorable feel on the skin during use.

[Properties and Preparations]

There are no particular limitations on the form of the external use composition of the second present invention, and can be in the form of a liquid, fluid or semi-solid. In addition, examples of preparation forms that can be adopted include a liquid, suspension, emulsion, cream, milky lotion, ointment, gel, liniment, lotion and sheet obtained by impregnating a non-woven fabric with a drug. Among these, an emulsion, cream, milky lotion, ointment, gel and lotion are preferable, and a cream, milky lotion, ointment and gel are particularly preferable.

Furthermore, a container of a known shape can be used without restriction for the container into which the external use composition of the second present invention is filled. There are also no limitations on the material of the container, and for example, the external use composition of the second present invention can be provided by filling into a container made of a material such as plastic or glass in the manner of polyethylene terephthalate, polyethylene naphthalate, polyarylate, polycarbonate, polyethylene or polypropylene. Polyethylene terephthalate, polyethylene naphthalate or polyarylate is particularly preferable for the material of the container.

<Production Method of External Use Composition>

There are no particular limitations on the method used to produce the external use composition of the second present invention, and can be produced by suitably selecting Component (A2), an optional component as previously described and other components followed by mixing in a solvent. For example, in order to obtain a gel-like composition, it is necessary to temporarily heat the components to 60° C. to 95° C. during the aforementioned mixing followed by allowing to stand at room temperature.

Including the Component (A2), the external use composition of the second present invention has enough antibacterial activity even if conventional sterilizer and antiseptic agent are not used or the blending amount of them is reduced. Because such a characteristic is provided, the external use composition of the second present invention can be preferably used in the field of cosmetics, quasi-drugs and medical supplies. Also, it can be preferably used as an external use composition for antibacterial, in particular, therapeutic use for the specifically (antipimple) lichenoid eczema for antiacne, dermatitis such as atopic dermatitis, the therapeutic use for intraoral decayed tooth and periodontal disease, therapeutic use for scalp eczema, suppression use for the body odor development in cosmetics, quasi-drugs and medical supplies territory. Also, as an external use composition for ophthalmology such as the eye salve medicine, it specifically can be preferably used as an external use composition for ophthalmology for antibacterial to the *Pseudomonas aeruginosa*.

<Antibiotics>

The antibiotics of the second present invention include an above-type (2-1) represented compound or the pharmaceutically acceptable salt (Component (A2)). The antibiotics of the second present invention can combine the component commonly used in cosmetics, quasi-drugs and medical supplies voluntarily appropriately for the purpose of also improving an antimicrobial effect as far as an antimicrobial effect is not lost. For the component which can be combined with antibiotics of the second present invention in this way, for example, above mentioned voluntary components of the external use composition of the second invention can be exemplified. Note that the description of the Component (A2) in the external use composition of the second present invention is applicable for the description of the Component (A2) in the antibiotics of the second present invention. Also, the antibiotics of the second present invention can be manufactured according to the method of the art by combining a component and other Components (A2). The antibiotics of the second present invention effect various kinds of microbes, in particular, an antimicrobial effect to fungus such as acne bacteria, *staphylococcus aureus, Pseudomonas aeruginosa, Escherichia coli*, microbes such as *Streptococ-*

*cus mutans* which can cause intraoral decayed tooth, periodontal disease and *Malassezia* bacteria, the *Candida* bacteria is remarkable.

<Antibacterial Method>

The second present invention includes the antibacterial method using the component (A2) which is superior in antibacterial. For example, bacterial breeding in those external use compositions, cosmetics, medicines can be inhibited by combining a component (A2) with the external use composition, the cosmetics and the medicines. Also, an antimicrobial effect can be shown to skin by applying the external use composition including the component (A2) to skin and, for example, can preferably be used for pimple care. Furthermore, according to the antibacterial method of the second present invention (A2), living environment can be maintained cleanly because the antibacterial treatment can be processed to various goods in the living environment by the various forms of products including the component (A2).

<Quasi-Drugs, Medical Supplies>

Quasi-drugs and medical supplies of the second present invention include antibiotics and external use composition of the second present invention. Therefore quasi-drugs and the medical supplies of the second present invention show a superior antibacterial effect to the symptoms and associated with *staphylococcus aureus Pseudomonas aeruginosa*, *Escherichia coli*, acne bacteria, *Candida* bacteria, *Malassezia* bacteria, and *Streptococcus mutans* in particular.

As symptoms and diseases associated with the *staphylococcus aureus*, examples of them include a dermatitis such as atopic dermatitis, various kinds of body odors such as the smell (hircismus) of the axillary region and the cephalic smell (head smell), the disease in the ophthalmology regions such as, blepharitis, dacryocystitis, stye, conjunctivitis, keratitis, the corneal ulcer. The quasi-drugs and the medical supplies of the second present invention can be preferably used as preventing and improving agent for dermatitis such as atopic dermatitis. Also, quasi-drugs and medical supplies of the second present invention can be preferably used as various kinds of body odor development inhibitors and the use of treatment and prevention for various kinds of diseases in the above ophthalmology region. Note that the application to the methicillin-resistant *staphylococcus aureus* which is multiple drug resistant bacteria is possible because a component (A) (e.g., Palmitoyl Dipeptide-18 (INCI name)) which quasi-drugs and medical supplies of the second present invention include is not an antibiotic drug.

Symptoms and diseases associated with the *Pseudomonas aeruginosa* include a pseudomonal corneal ulcer and pseudomonal keratitis, for example. Quasi-drugs and the medical supplies of the second present invention can be preferably used as for treatment and prevention of these pseudomonal diseases. Note that the application to multi-drug-resistant *Pseudomonas aeruginosa* is possible because a component (A) (e.g., PalmitoylDipeptide-18 (INCI name)) which quasi-drugs and medical supplies of the second present invention include is not antibiotic drug.

Acne can be exemplified as the symptom or the disease associated with acne bacteria. Acne includes the acne of the drying skin, the acne which is apt to be repeated, the acne with inflammation in the folliculus pili, the scintilla acne (angle stopper development, initial angle stopper jamming), the eruption (adult pimple), the white acne (white rash papular), the black acne (releasing pimple), the red acne (red rash papular) with inflammation, the yellow acne (suppuration pimple), the vulgarity acne which are easy to be seen for puberty, the pustule-related acne mainly composed of pustules, the cysts-related acne mainly composed of cysts, the acne conglobata which is a severe case of vulgarity acne, and the fulminant acne in such as face part, a neck or the back part, but should not be limited to the above. And quasi-drugs and medical supplies of the second present invention can preferably be used for treatment and prevention of these acnes.

The symptoms and diseases associated with *Candida* bacteria include candidiasis. Candidiasis includes such as, but should not be limited to, skin candidiasis, vaginal candidiasis, external genitalia candidiasis, sexual organs candidiasis of the man, oral candidiasis, the erosion symptom between the candidal finger, candidal pawl wall onychia, esophagus, intestinal candidiasis. Quasi-drugs and the medical supplies of the second present invention can be preferably used as for treatment and prevention of these Candidiasis symptoms.

The symptoms and diseases associated with *Malassezia* bacteria include, for example, the eczema of the back, scalp eczema, *Malassezia* folliculitis, seborrheic dermatitis, tinea versicolor, dandruff and the like. Quasi-drugs and the medical supplies of the second present invention can be preferably used as for treatment and prevention of the eczema of these backs, scalp eczema, *Malassezia* folliculitis, seborrheic dermatitis, and tinea versicolor. Also, it is preferably used for palliation and improvement for development of the dandruff.

The symptoms and diseases associated with *Streptococcus mutans* include, for example, intraoral caries, periodontal disease, gingivitis, alveolar pyorrhea and quasi-drugs and the medical supplies of the second present invention can be preferably used for treatment and prevention of these symptoms and diseases.

<Cosmetics>

The cosmetics of the second present invention are superior in the antimicrobial effect by including the component (A2), which is represented as above-type (2-1), and specifically have a superior antimicrobial effect to *staphylococcus aureus, Pseudomonas aeruginosa, Escherichia coli*, acne bacteria, *Candida* bacteria, *Malassezia* bacteria and *Streptococcus mutans*. Therefore, in the field of cosmetics, it is widely used for cosmetics such as agents suppressing for the development of the body odors and such as beauty lotion, milky lotion and essence for treatment and prevention of acne described above.

<Ophthalmic Composition Thing>

The ophthalmic composition of the second present invention includes the component (A2) which is represented by the formula (2-1). Since component (A2) has a function as the gelatinizer, the ophthalmic composition of the second present invention is preferably used as medicines and quasi-drugs. Also, the ophthalmic composition of the second present invention is preferably used as medicines and quasi-drugs which are superior in antibacterial activity in particular. Specifically, it can be used as an eye drop (including eye drops, the eyedrop), collyria (including the eyewash, washing eyes liquid), eye salve medicine, contact lens mounting liquid, care agents for contact lenses (washings, medium, antiseptic solution, multi-parr pass solution loss reaction). Note that an eye drop and collyria include eye drop and collyria which can be used with wearing contact lens. Also, the contact lens described above includes the all types of contact lenses such as a hard contact lens (including the oxygen permeability hard contact lens) and soft contact lens. Also, use dose when it is used as medical care for ophthalmology is different by the intended uses, and it should be used with the use dose that is usually adopted to each intended use. Note that, about the component (A2), solvents, voluntariness components, and the property of the ophthalmic composition of the second present invention which the ophthalmic composition of the second present invention includes, the description of the external use composition of the second present invention can be applied in the case they can be used for the ophthalmic composition. Also, about the method for manufacturing of the ophthalmic composition of the second present invention, the description of the method for manufacturing of the external use composition of the second present invention can be applied in the case they can be used for the ophthalmic composition.

[This Second Mode of Operation of Invention]

The second present invention is described below based on practical example further in detail, but the second present invention is not limited to these practical examples.

[Preparation of the Composition]

According to the prescription described in following Tables 2-1, a composition (test preparation) of practical example and the comparative example was prepared by law of the art. The numerical unit in each list is weight (%) unless otherwise specified. As mentioned below, the tests were hold and the each composition was evaluated.

Test Example

<Antibacterial Test (Acne Bacteria)>

About the evaluation of the sample test liquid, antimicrobial effects were evaluated with the method of direct inoculation to bacteria. Specifically, the acne bacterial suspension in which acne bacteria was cultured in anaerobic condition in advance in modified GAM agar (Gifuanaerobicmedium agar) for 36° C. and 72 hours, was inoculated into about $1.0 \times 10^6$ CFU/mL to sample test liquid. Then, it was cultured in 36° C. and anaerobic conditions, a sample inoculated after predetermined time was diluted, viable bacteria count was measured by the method of the agar plate surface smear, and an antimicrobial effect was ensured. (for 5 minutes. 30 minutes. 60 minutes. 90 minutes. 240 minutes.). The effect is shown to following Tables 2-2 and FIG. 2-1.

TABLES 2-2

| | | •Direct inoculation | | | | | [CFU/mL] |
|---|---|---|---|---|---|---|---|
| Test bacteria | Sample name | 0 min | 5 min | 30 min | 60 min | 90 min | 240 min |
| P. acnes | Example 2-1 | $1.9 \times 10^6$ | $1.0 \times 10^4$ | <100 | <100 | <100 | <100 |
| | Example 2-2 | $1.9 \times 10^6$ | $7.4 \times 10^5$ | $1.3 \times 10^4$ | $1.0 \times 10^2$ | <100 | <100 |
| | Comp. Ex. 2-1 | $1.9 \times 10^6$ | $7.7 \times 10^5$ | $1.3 \times 10^5$ | $2.4 \times 10^4$ | $4.0 \times 10^3$ | <100 |
| | Comp. Ex. 2-3 | $1.9 \times 10^6$ | $1.3 \times 10^6$ | $7.0 \times 10^4$ | $2.7 \times 10^4$ | $7.4 \times 10^3$ | <100 |

TABLES 2-1

| Sample name | Example 2-1 | Example 2-2 | Example 2-3 | Comp. Ex. 2-1 | Comp. Ex. 2-2 | Comp. Ex. 2-3 |
|---|---|---|---|---|---|---|
| Pal-GH | 0.1 | — | 0.5 | — | — | — |
| GH | — | 0.1 | — | — | — | — |
| IPMP | — | — | — | 0.1 | — | — |
| MP | — | — | — | — | 0.1 | — |
| 1,3-BG | 99.9 | 99.9 | 99.5 | 99.9 | 99.9 | 100 |
| Total | 100 | 100 | 100 | 100 | 100 | 100 |

Note that the in the embodiment sample name of lists shows the following.
Pal-GH: Palmitoyl Dipeptide-18 (INCI name)
GH: Dipeptide of glycine and the histidine
IPMP: Isopropyl methylphenol
MP: Methylparaben
1,3-BG or BG: 1,3-butylene glycol As shown in Tables 2-2 and FIG. 2-1, the composition of Example 2-1 and 2-2 showed superior antimicrobial action to the acne bacteria in comparison with a composition of comparative examples 2-1 and 2-3 including the existing sterilizer.

<Antibacterial Test (*Staphylococcus aureus*)>

About the evaluation of the sample test liquid, antimicrobial effects were evaluated by the method of direct inoculation to bacteria. More particularly, the *staphylococcus aureus* suspension in which the *staphylococcus aureus* was cultured in advance in SCDLP agar (Soybean-CaseinDigestAgarwithLecithin & Polysorbate80 agar) for 33° C. and 24 hours, was inoculated into about $3.7 \times 10$ CFU/mL to sample test liquid. And, it was cultured in 33° C., a sample inoculated after predetermined time was diluted, viable bacteria count was measured by the method of the agar plate surface smear, and an antimicrobial effect was ensured (0.5 hour, 1 hour, 4 hours, 24 hours). The effect is shown to following Tables 2-3 and FIG. 2-2.

TABLES 2-3

| | | •Direct inoculation | | | | [CFU/mL] |
|---|---|---|---|---|---|---|
| Test bacteria | Sample name | Start | 30 min | 60 min | 4 h | 24 h |
| S. aureus | Example 2-1 | $3.7 \times 10^6$ | $7.5 \times 10^5$ | $4.0 \times 10^5$ | $1.2 \times 10^4$ | <100 |
| | Example 2-3 | | $5.3 \times 10^5$ | $1.1 \times 10^5$ | $4.0 \times 10^2$ | <100 |
| | Comp. Ex. 2-1 | | $2.1 \times 10^6$ | $1.8 \times 10^6$ | $1.3 \times 10^6$ | $6.8 \times 10^5$ |
| | Comp. Ex. 2-2 | | $2.1 \times 10^6$ | $1.7 \times 10^6$ | $8.9 \times 10^5$ | $4.9 \times 10^5$ |
| | Comp. Ex. 2-3 | | $2.3 \times 10^6$ | $1.7 \times 10^6$ | $1.2 \times 10^6$ | $1.1 \times 10^6$ |

As shown in Tables 2-3 and FIG. 2-2, the composition of Example 2-1 and 2-3 showed superior antimicrobial action 24 hours after the inoculation of the bacteria than it corresponded to *staphylococcus aureus* in comparison with a composition of comparative examples 2-1, 2-2 and 2-3 including the existing sterilizer.

<Antibacterial Test (*Streptococcus mutans*)>

*Streptococcus mutans* (a scientific name: *Streptococcus mutans*) is gram-positive and is a kind of facultative anaerobic *Streptococcus*. It exists in the oral cavity of the human and is one of the causative organisms of the caries (dental caries). About the evaluation of the sample test liquid, antimicrobial effects were evaluated using the method of direct inoculation to bacteria. More particularly, the *Streptococcus mutans* suspension in which the *streptococcus mutans* was cultured in advance in BHI culture media (brainheartinfusion culture media) for 33° C., 24 hours, was inoculated into about $1.0 \times 10^6$ CFU/mL to sample test liquid. And, it was cultured in 33° C., a sample inoculated after predetermined time was diluted, viable bacteria count was measured by the method of the agar plate surface smear, and an antimicrobial effect was ensured. (0.5 hours 0.1 hours 0.4 hours 0.24 hours). An effect is shown to following Tables 2-4 and FIG. 2-3.

TABLES 2-4

| Test bacteria | •Direct inoculation Sample name | Start | 30 min | 1 h | 4 h | [CFU/mL] 24 h |
|---|---|---|---|---|---|---|
| S. mutans | Example 2-1 | $1.0 \times 10^6$ | $1.4 \times 10^5$ | $1.3 \times 10^4$ | <100 | <100 |
|  | Example 2-3 |  | $1.8 \times 10^4$ | <100 | <100 | <100 |
|  | Comp. Ex. 2-1 |  | $1.2 \times 10^5$ | $1.4 \times 10^5$ | $5.0 \times 10^4$ | $5.5 \times 10^3$ |
|  | Comp. Ex. 2-2 |  | $1.1 \times 10^5$ | $1.3 \times 10^5$ | $8.0 \times 10^4$ | $1.6 \times 10^3$ |
|  | Comp. Ex. 2-3 |  | $4.0 \times 10^5$ | $1.3 \times 10^5$ | $4.0 \times 10^4$ | $4.9 \times 10^3$ |

As shown in Tables 2-4 and FIG. 2-2, the composition of Example 2-1 and 2-3 showed superior antimicrobial action to *Streptococcus mutans* in comparison with a composition of comparative example 2-1, 2-2, and 2-3 including the existing sterilizer in a shorter time.

<Preservation Sterilization Test (*Escherichia coli*)>

About the evaluation of the sample test liquid, the antimicrobial effect was evaluated with the method of diffusion (punching plating method). More particularly, *Escherichia coli* (*Escherichia coli* ATCC 8739) was cultured in SCD (Soybean-Casein Digest) slant medium for 33° C., 24 hours and the bacterial suspension was made. The bacterial suspension was spread in MH agar (Mueller-Hinton agar) with about $10^6$ CFU/mL. Then a hole of 8 mm in diameter was made with a punching cutting head (TOYOBO: biopsy punch 8 mm, a product made in stainless steel) which had been sterilized, the sample test liquid 100 uL was inoculated into the hole and cultured for 33° C., 48 hours. After incubations, the diameter of inhibition ring which appeared around a hole was measured. The effect is shown to following Tables 2-5 and FIG. 2-4.

TABLES 2-5

| Test bacteria | Sample name | Inhibition ring (mm) |
|---|---|---|
| E. coli | Example 2-1 | 13.5 |
|  | Example 2-2 | 12.3 |
|  | Comp. Ex. 2-1 | 11.7 |
|  | Comp. Ex. 2-2 | 11.9 |
|  | Comp. Ex. 2-3 | 11.5 |

Figures 1, 2:
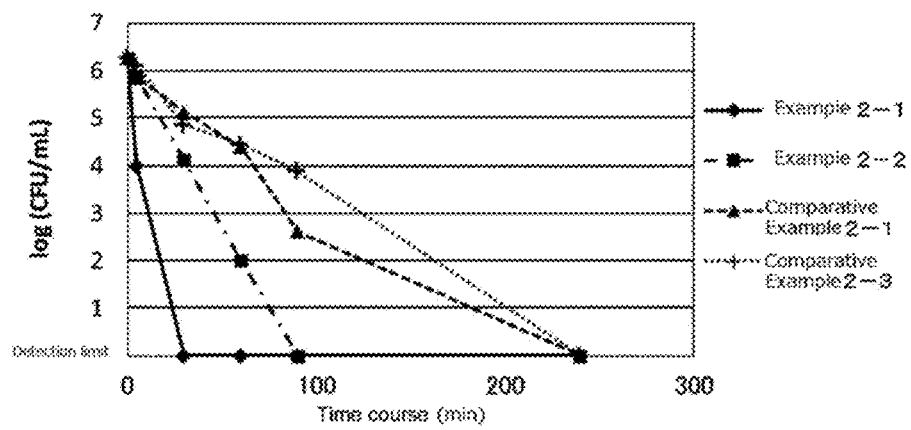
Figure 2:
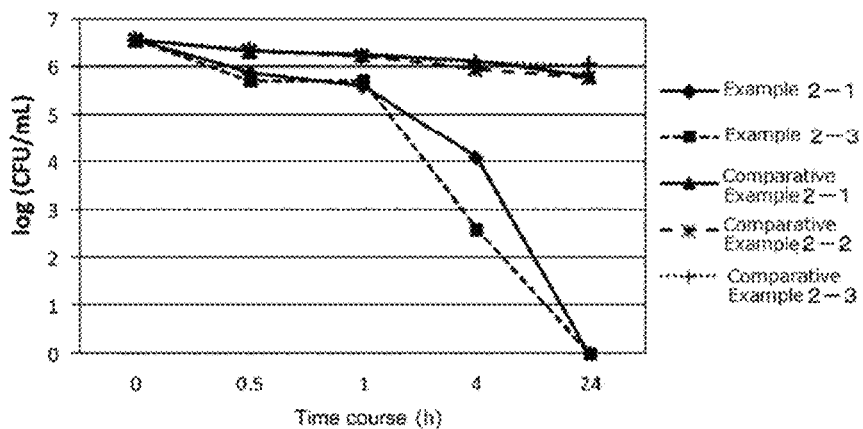
Figures 2, 3:
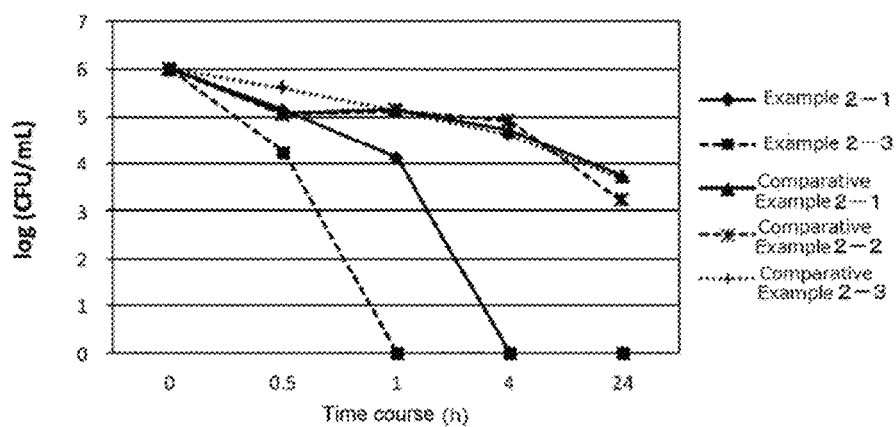
Figures 2, 3, 4:
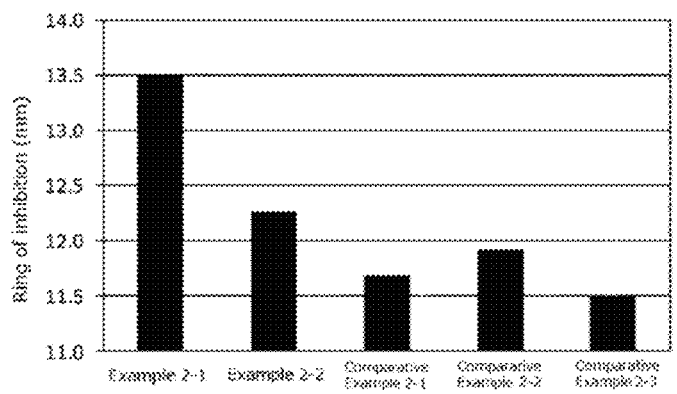

As shown in Tables 2-5 and FIG. 2-4, the composition of Example 2-1 and 2-2 showed superior preservative and sterilizing property to *Escherichia coli* in comparison with a composition of comparative example 2-1-2-3 including the existing sterilizer.

<Sterilization Test (*Pseudomonas aeruginosa*)>

About the evaluation of the sample test liquid, the antimicrobial effect was evaluated with the method of diffusion (punching plating method). More particularly, *Pseudomonas aeruginosa* (*Pseudomonas aeruginosa*, ATCC 9027) was cultured in SCD (Soybean-Casein Digest) slant medium for 33° C., 24 hours and the bacterial suspension was made. The bacterial suspension was spread in MH agar (Mueller-Hinton agar) with about $10^6$ CFU/mL. Then a hole of 8 mm in diameter was made with a punching cutting head (TOYOBO: biopsy punch 8 mm, a product made in stainless steel) which had been sterilized, the sample test liquid 100 uL was inoculated into the hole and cultured for 33° C., 48 hours. After incubations, the diameter of inhibition ring which appeared around a hole was measured. The effect is shown to following Tables 2-6 and FIG. 2-5.

TABLES 2-6

| Test bacteria | | Inhibition ring (mm) |
|---|---|---|
| P. aeruginosa | Example 2-1 | 15.7 |
|  | Example 2-2 | 15.2 |
|  | Comp. Ex. 2-1 | 14.9 |
|  | Comp. Ex. 2-3 | 14.0 |

As shown in Tables 2-6 and FIG. 2-5, the composition of Example 2-1 and 2-2 showed superior sterilizing property to the *Pseudomonas aeruginosa* in comparison with comparative example 2-1, 2-3 compositions including the existing sterilizer.

<Sterilization Test (*Malassezia* Bacteria)>

About the evaluation of the sample test liquid, antimicrobial effects were evaluated using the method of direct inoculation to bacteria. More particularly, the the *Malassezia* bacterial suspension in which the the *Malassezia* bacteria was cultured in advance in BHI culture media (brainheart-infusion culture media) for 33° C., 5 days, was inoculated into about $1.6 \times 10^6$ CFU/mL to the sample test liquid. And, a sample inoculated after predetermined time was diluted, viable bacteria count was measured by the method of the agar plate surface smear, and an antimicrobial effect was ensured. (0.5 hours 0.1 hours 0.4 hours 0.24 hours). The effect is shown to following Tables 2-7 and FIG. 2-6.

TABLES 2-7

| Test bacteria | •Direct inoculation Sample name | [CFU/mL] | | | | |
| --- | --- | --- | --- | --- | --- | --- |
| | | start | 30 min | 1 h | 4 h | 24 h |
| M. furfur | Example 2-1 | $1.6 \times 10^6$ | $8.0 \times 10^2$ | <100 | <100 | <100 |
| | Example 2-3 | | <100 | <100 | <100 | <100 |
| | Comp. Ex. 2-1 | | $6.0 \times 10^3$ | $1.0 \times 10^3$ | <100 | <100 |
| | Comp. Ex. 2-2 | | $3.4 \times 10^3$ | $4.0 \times 10^2$ | <100 | <100 |
| | Comp. Ex. 2-3 | | $6.0 \times 10^3$ | $5.0 \times 10^2$ | <100 | <100 |

As shown in Tables 2-7 and FIG. 2-6, the composition of Example 2-1 and 2-3 showed superior antimicrobial action to the *Malassezia* bacteria in comparison with a composition of comparative example 2-1-2-3 including the existing sterilizer in a shorter time.

<Sterilization Test (*Candida* Bacteria)>

About the evaluation of the sample test liquid, the antimicrobial effect was evaluated using the method of diffusion (punching plating method). More particularly, *candida* (*Candida albicans* ATCC 10231) was cultured in SCD (Soybean-Casein Digest) slant medium for 24° C., 48 hours and the bacterial suspension was made. The bacterial suspension was spread in MH agar (Mueller-Hinton agar) with about $10^6$ CFU/mL. Then a hole of 8 mm in diameter was made with a punching cutting head (TOYOBO: biopsy punch 8 mm, a product made in stainless steel) which had been sterilized, the sample test liquid 100 uL was inoculated into the hole and cultured for 33° C., 48 hours. After incubations, the diameter of inhibition ring which appeared around a hole was measured. The effect is shown to following Tables 2-8 and FIG. 2-7.

TABLES 2-8

| Test bacteria | Sample name | Inhibition ring (mm) |
| --- | --- | --- |
| C. albicans | Example 2-1 | 14.45 |
| | Example 2-3 | 15.07 |
| | Comp. Ex. 2-2 | 13.97 |
| | Comp. Ex. 2-3 | 13.27 |

As shown in Tables 2-8 and FIG. 2-7, the composition of Example 2-1 and 2-2 showed superior sterilizing property to the *Candida* bacteria in comparison with a composition of comparative example 2-2 and 2-3 including the existing sterilizer.

The composition of the practical example showed superior antimicrobial action to various kinds of microbes as above. Therefore, the composition of the practical example can be widely used as an external use composition for antibacterial and as cosmetics, quasi-drugs and/or medical supplies comprising an antimicrobial effect and preservative and sterilizing effect to a microbe, fungus participating in skin disease (pimple, scalp eczema, eczema of the back, lichenoid eczema), oral disease (dental caries, periodontal disease, inflammation of gums) and body odor. Also, because it is superior in antimicrobial action to the *Pseudomonas aeruginosa*, it can be preferably used as an ophthalmic composition.

By conventional methods, the skin external preparations (prescription example 2-1-2-14) of the following compositions were prepared.

Formulation 2-1: Whitening Essence

TABLE 2-9

| Component | Content (%) |
| --- | --- |
| L-ascorbic acid | 20 |
| Diethylene glycol monoethyl ether | 30 |
| Propylene glycol | 20 |
| Glycerin | 4 |
| Lactic acid | 1.5 |
| Iris root extract | 0.01 |
| Grapefruit extract | 0.5 |
| Glasswort extract | 0.5 |
| Fragrance | 0.1 |
| Pal-GH | 0.5 |
| Purified water | Balance |
| Total | 100 |

Formulation Example 2-2: Whitening Milky Lotion

TABLE 2-10

| Component | Content (%) |
| --- | --- |
| L-ascorbic acid | 20 |
| Polyglyceryl stearate | 1 |
| Ethylene glycol monoethyl ether | 40 |
| Sodium lactate | 0.1 |
| Stearyl alcohol | 1 |
| Squalane | 1 |
| Lavender oil | 0.5 |
| Chamomile extract | 0.5 |
| Sakhalin kelp extract | 0.5 |
| Pal-GH | 0.5 |
| Purified water | Balance |
| Total | 100 |

Formulation Example 2-3: Whitening Cream

TABLE 2-11

| Component | Content (%) |
| --- | --- |
| L-ascorbic acid | 20 |
| Ethylene glycol monoethyl ether | 30 |
| Sorbitan stearate | 0.7 |
| PEG sorbitan stearate | 1 |
| Paraffin | 5 |
| Cetanol | 2 |
| Glycerin | 3 |
| 1,3-butylene glycol | 5 |
| Allantoin | 0.1 |

TABLE 2-11-continued

| Component | Content (%) |
|---|---|
| Xanthan gum | 0.1 |
| Pal-GH | 0.5 |
| Purified water | Balance |
| Total | 100 |

Formulation Example 2-4: Spray Cosmetic

TABLE 2-12

| Component | Content (%) |
|---|---|
| L-ascorbic acid | 8 |
| Ethylene glycol monoethyl ether | 50 |
| Ethanol | 10 |
| Aloe extract | 0.1 |
| Pal-GH | 1 |
| Purified water | Balance |
| Total | 100 |

Formulation Example 2-5: External Skin Preparation

TABLE 2-13

| Component | Content (%) |
|---|---|
| L-ascorbic acid | 20 |
| Ethylene glycol monoethyl ether | 30 |
| Sorbitan stearate | 0.7 |
| PEG sorbitan stearate | 1 |
| Paraffin | 5 |
| Cetanol | 2 |
| Glycerin | 3 |
| 1,3-butylene glycol | 5 |
| Allantoin | 0.1 |
| Xanthan gum | 0.1 |
| Pal-GH | 0.5 |
| Purified water | Balance |
| Total | 100 |

Formulation Example 2-6: Sunscreen

TABLE 2-14

| Component | Content (%) |
|---|---|
| Arbutin | 3 |
| Trimethylglycine | 1 |
| 2-ethylhexyl para-methoxycinnamate | 10 |
| Decamethylcyclopentasiloxane | 20 |
| Octyl palmitate | 10 |
| Polyoxyethylene-methylpolysiloxane copolymer | 3 |
| Methyl hydrogenpolysiloxane-treated low temperature-fired zinc oxide | 15 |
| Alkyl polyacrylate | 5 |
| Concentrated glycerin | 5 |
| Absolute ethanol | 5 |
| 1,3-butylene glycol | 3 |
| Panthenol | 0.1 |
| Fragrance | 0.1 |

TABLE 2-14-continued

| Component | Content (%) |
|---|---|
| Phytic acid | 0.05 |
| Pal-GH | 0.5 |
| Purified water | Balance |
| Total | 100 |

Formulation Example 2-7: Whitening Milky Lotion

TABLE 2-15

| Component | Content (%) |
|---|---|
| Arbutin | 3 |
| Trimethylglycine | 2 |
| Polyglyceryl-10 isostearate | 2 |
| Polyoxyethylene hydrogenated castor oil (HCO-10) | 0.5 |
| Squalane | 5 |
| Carboxyvinyl polymer | 0.2 |
| Triethanolamine | 0.1 |
| Concentrated glycerin | 5 |
| Magnesium sulfate | 0.1 |
| Sodium edetate | 0.05 |
| Methyl paraoxybenzoate | 0.2 |
| Pal-GH | 0.5 |
| Purified water | Balance |
| Total | 100 |

Formulation Example 2-8: Whitening Cream

TABLE 2-16

| Component | Content (%) |
|---|---|
| Arbutin | 3 |
| Trimethylglycine | 2 |
| Lauryl dimethicone polyglycerin-3 crosspolymer-glyceryl tri(2-ethylhexanoate) | 5 |
| Crosslinked methylpolysiloxane-methylpolysiloxane | 5 |
| Crosslinked alkyl-modified silicon-glyceryl tri(2-ethylhexanoate) | 3 |
| Decamethylcyclopentasiloxane | 15 |
| Polymethylsilsesquioxane | 3 |
| (Dimethicone-vinyl dimethicone-methicone) crosspolymer | 1 |
| Alkyl polyacrylate | 5 |
| Concentrated glycerin | 10 |
| Magnesium sulfate | 0.1 |
| Sodium edetate | 0.05 |
| Cyanocobalamin | 0.01 |
| Methyl paraoxybenzoate 0.05 | 0.2 |
| Pal-GH | 0.5 |
| Purified water | Balance |
| Total | 100 |

Formulation Example 2-9: Whitening Essence

TABLE 2-17

| Component | Content (%) |
|---|---|
| Hydroquinone | 1 |
| Diethylene glycol monoethyl ether | 30 |
| Hyaluronic acid | 0.05 |
| 1,3-butylene glycol | 50 |

TABLE 2-17-continued

| Component | Content (%) |
|---|---|
| Melhyl paraoxybenzoate | 0.05 |
| Pal-GH | 0.5 |
| Purified water | Balance |
| Total | 100 |

Formulation Example 2-10: Aging Care Cream

TABLE 2-18

| Component | Content (%) |
|---|---|
| Astaxanthin | 0.1 |
| Trimethylglycine | 0.1 |
| Pentaerythritol tetra(2-ethylhexanoate) | 5 |
| White Vaseline | 2 |
| Polyoxyethylene sorbitan stearate | 2 |
| Carboxyvinyl polymer | 0.1 |
| 1,3-butylene glycol | 5 |
| Cetanol | 0.5 |
| Concentrated glycerin | 5 |
| Cyanocobalamin | 0.01 |
| L-arginine | 0.1 |
| Xanthan gum | 0.1 |
| Hydroxyethyl cellulose | 0.1 |
| Sodium alginate | 0.1 |
| Methyl paraoxybenzoate | 0.2 |
| Propyl paraoxybenzoate | 0.05 |
| Pal-GH | 1 |
| Purified water | Balance |
| Total | 100 |

Formulation Example 2-11: Aging Care Essence

TABLE 2-19

| Component | Content (%) |
|---|---|
| Astaxanthin | 0.5 |
| Trimethylglycine | 3 |
| Sodium ascorbate | 10 |
| Hyaluronic acid | 0.05 |
| 1,3-butylene glycol | 5 |
| Polyoxyethylene hydrogenated castor oil 80 | 1 |
| Methyl paraoxybenzoate | 0.05 |
| Pal-GH | 0.5 |
| Purified water | Balance |
| Total | 100 |

Formulation Example 2-12: Whitening Essence

TABLE 2-20

| Component | Content (%) |
|---|---|
| 3-O-ethyl ascorbic acid | 3 |
| Diethylene glycol monoethyl ether | 30 |
| Propylene glycol | 20 |
| Glycerin | 4 |
| Lactic acid | 1.5 |
| Iris root extract | 0.01 |
| Grapefruit extract | 0.5 |
| Glasswort extract | 0.5 |

TABLE 2-20-continued

| Component | Content (%) |
|---|---|
| Brown algae extract | 0.1 |
| Pal-GH | 0.5 |
| Purified water | Balance |
| Total | 100 |

Formulation Example 2-13: Topical Hair Tonic

TABLE 2-21

| Component (content %) | Formulation Ex. 2-13-1 | Formulation Ex. 2-13-2 | Formulation Ex. 2-13-3 | Formulation Ex. 2-13-4 |
|---|---|---|---|---|
| Minoxidil | 0.5 | 1 | 0.1 | — |
| Resorcin | 1 | — | — | — |
| Pantothenyl ethyl ether | 0.1 | — | 0.5 | 0.2 |
| Hinokitiol | — | 0.05 | — | — |
| L-menthol | 0.01 | 0.1 | 1 | — |
| DL-camphor | — | — | — | 0.01 |
| Swertia japonica extract | 0.1 | 1 | 2 | — |
| Carrot extract | — | 0.1 | 2 | 1 |
| Tocopherol acetate | — | 0.5 | — | — |
| Dipotassium glycyrrhizate | 0.05 | — | 0.1 | 2 |
| Ethanol | 40 | 30 | 10 | — |
| Propylene glycol | 10 | — | 5 | — |
| Dipropylene glycol | — | 10 | 5 | 2 |
| Diethylene glycol monoethyl ether | — | 10 | 20 | 30 |
| Xanthan gum | — | 0.1 | — | — |
| Polyoxyethylene hydrogenated castor oil 60 | 1 | — | — | — |
| Pal-GH | 0.5 | 0.5 | 1 | 5 |
| Purified water | Balance | Balance | Balance | Balance |
| Total | 100 | 100 | 100 | 100 |

Formulation Example 2-14: External Antibacterial Preparation

TABLES 2-22

| Component (Content %) | Formulation Ex. 2-14-1 | Formulation Ex. 2-14-2 | Formulation Ex. 2-14-3 | Formulation Ex. 2-14-4 |
|---|---|---|---|---|
| Terbinafine hydrochloride | 1 | 0.1 | 1 | 1 |
| Diphenhydramine hydrochloride | 2 | 1 | 0.5 | 0.2 |
| Dibucaine hydrochloride | 0.4 | 0.5 | 0.1 | 0.5 |
| Butenafine hydrochloride | — | — | 1 | 0.2 |
| Glycyrrhetinic acid | 0.02 | 0.1 | — | — |
| Chlorobutanol | — | 1 | 0.1 | — |
| Crotamine | 0.1 | — | — | — |
| Isopropyl methylphenol | 0.01 | — | 0.1 | — |
| L-menthol | 0.2 | — | 1 | — |
| DL-camphor | — | 1 | — | 0.1 |
| Propylene glycol | 5 | 10 | — | 10 |
| Ethanol | 10 | 5 | 10 | 30 |
| Dipropylene glycol | 10 | 10 | — | — |
| Diethylene glycol monoethyl ether | — | 10 | 5 | — |

TABLES 2-22-continued

| Component (Content %) | Formulation Ex. 2-14-1 | Formulation Ex. 2-14-2 | Formulation Ex. 2-14-3 | Formulation Ex. 2-14-4 |
|---|---|---|---|---|
| Polyoxyethylene hydrogenated castor oil 60 | 1 | — | — | — |
| Pal-GH | 0.5 | 0.5 | 1 | 5 |
| Purified water | Balance | Balance | Balance | Balance |
| Total | 100 | 100 | 100 | 100 |

This completes the explanation of the second present invention. Continuing, an explanation of the third present invention is provided.

The Third Present Invention

The third present invention relates to a method for enhancing percutaneous absorption of the active ingredient in an external use composition, cosmetic, percutaneous absorption promoting composition or external use composition, and to a percutaneously administered drug and composition for instillation.

BACKGROUND ART

It is becoming increasingly common to incorporate the active ingredients of various types of drugs in external use compositions to impart various types of functions to those compositions. The aforementioned active ingredient may be hydrophilic or hydrophobic or have a large molecular size or small molecular size depending on the structure thereof.

The skin to which the aforementioned composition is applied has the function of biological barrier that separates the body from the outside world, and a composition that is hydrophilic or has a large molecular size typically has difficulty in permeating the skin. Although the skin prevents various types of harmful substances (such as bacteria) from infiltrating the body due to this property, this property may also function as a barrier to the active ingredients of drugs as described above, thereby preventing these active ingredients from being absorbed into the body.

Therefore, methods consisting of enhancing the lipophilicity of a component by modifying the chemical structure thereof, combining with the use of a third component other than the active ingredient referred to as a percutaneous absorption promoter, or employing a physical method in the manner of iontophoresis, are employed in order to enhance absorption of an active ingredient from the skin into the body.

Furthermore, Patent Document 3-1 discloses a cosmetic comprising a low molecular weight lipopeptide represented by the formula indicated below.

[Chemical 13]

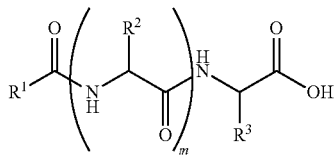

According an example in this document, a cosmetic which incorporates indomethacin, 1-menthol and palmitoyl glycyl histidine trifluoroacetate, and an external preparation which incorporates indomethacin, camphor and palmitoyl glycyl histidine, are prepared. However, this document does not describe or suggest the use of the aforementioned low molecular weight lipopeptide to enhance percutaneous absorption of an active ingredient.

PRIOR ART DOCUMENTS

Patent Documents

[Patent Document 3-1] International Publication No. WO 2011/052613

Disclosure of the Third Present Invention

Problems to be Solved by the Third Present Invention

An object of the third present invention is to provide an external use composition having superior percutaneous absorption of an active ingredient.

Means for Solving the Problems of the Third Present Invention

As a result of conducting extensive studies to solve the aforementioned problems, the inventors of the present invention found that percutaneous absorption of an active ingredient can be enhanced by combining a polyvalent alcohol and/or glycol ether with a prescribed lipopeptide, thereby leading to completion of the third present invention.

Namely, the gist of the third present invention is as indicated below.

<1> An external use composition comprising:
(A) a lipopeptide represented by the following formula (i) and/or a pharmaceutically acceptable salt thereof, and
(B) a polyvalent alcohol and/or a glycol ether; wherein,
the content of Component (A) in the external use composition is 0.05% by weight or more:

[Chemical 14]

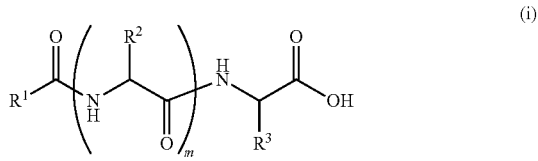

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

<2> The external use composition described in <1>, further comprising an active ingredient (C).

<3> The external use composition described in <1> or <2>, wherein $R^2$ in the formula (i) represents a hydrogen atom, methyl group, i-propyl group, i-butyl group or sec-butyl group.

<4> The external use composition described in <2> or <3>, wherein the active ingredient (C) is at least one type selected from the group consisting of a disinfectant component, anti-inflammatory component, anti-inflammatory analgesic component, antipruritic component, vitamin, local anesthetic component, moisturizing component, whitening component, antioxidant component, anti-aging component, keratin softening component, cell activating component, circulation promoting component, component having action that prevents and/or repairs damaged DNA, ultraviolet absorbing component, ultraviolet scattering component, astringent component, hair growth component, antihistamine component and antiseptic component.

<5> The external use composition described in any of <1> to <4>, further comprising terpenes (D).

<6> The external use composition described in <5>, wherein the terpene (D) is menthol.

<7> The external use composition described in any of <1> to <6>, wherein the content of the Component (B) in the external use composition is 0.0001% to 75% by weight.

<8> The external use composition described in any of <1> to <7>, wherein $R^1$ in the formula (i) represents an aliphatic group having 13 to 17 carbon atoms, $R^2$ represents a hydrogen atom, methyl group or i-propyl group, and $R^3$ represents a 4-aminobutyl group, 4-imidazolemethyl group or 3-methylindole group.

<9> A cosmetic comprising the external use composition described in any of <1> to <8>.

<10> A percutaneous absorption promoting composition comprising:
(A) a lipopeptide represented by the following formula (i) and/or a pharmaceutically acceptable salt thereof, and
(B) a polyvalent alcohol and/or glycol ether; wherein,
the content of the Component (A) in the percutaneous absorption promoting composition is 0.05% by weight or more:

[Chemical 15]

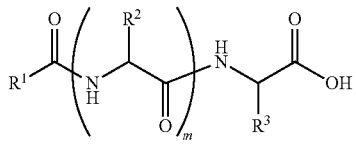

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

<11> A method for enhancing percutaneous absorption of an active ingredient in the external use composition, incorporating (A) a lipopeptide represented by the following formula (i) and/or a pharmaceutically acceptable salt thereof, in an external use composition comprising (C) an active ingredient and (B) a polyvalent alcohol and/or glycol ether:

[Chemical 16]

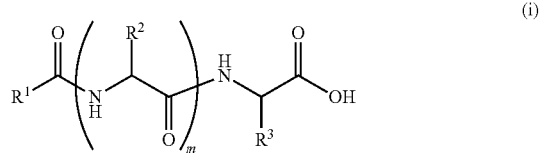

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

<12> A percutaneously administered drug comprising a medicinal component, (A) a lipopeptide represented by the following formula (i) and/or a pharmaceutically acceptable salt thereof, and (B) a polyvalent alcohol and/or glycol ether, wherein,
the content of the Component (A) in the percutaneously administered drug is 0.05% by weight or more:

[Chemical 17]

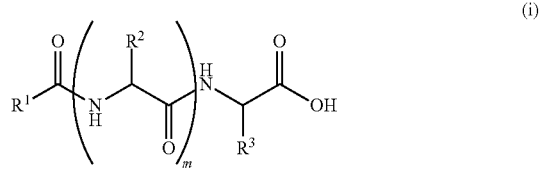

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

<13> A composition for instillation comprising a medicinal component, (A) a lipopeptide represented by the following formula (i) and/or a pharmaceutically acceptable salt thereof, and (B) a polyvalent alcohol and/or glycol ether, wherein, the content of the Component (A) in the composition for instillation is 0.05% by weight or more:

[Chemical 18]

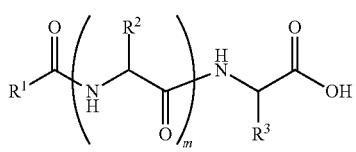

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

Effects of the Third Present Invention

According to the third present invention, an external use composition is provided that demonstrates superior percutaneous absorption of an active ingredient.

[Best Mode for Carrying Out the Third Present Invention]

The following provides a detailed explanation of the external use composition, cosmetic, composition for promoting percutaneous absorption, method for enhancing percutaneous absorption of an active ingredient in an external use composition, percutaneously absorbed drug and composition for instillation of the third present invention.

[External Use Composition]

The external use composition of the third present invention comprises (A) a lipopeptide represented by the aforementioned formula (i) and/or a pharmaceutically acceptable salt thereof, and (B) a polyvalent alcohol and/or glycol ether. The following provides an explanation of these essential components as well as components able to be contained by the aforementioned composition.

<(A) Lipopeptide and/or Pharmaceutically Acceptable Salt Thereof>

The lipopeptide used in the third present invention is a compound composed of an $R^1CO$ lipid moiety represented by the following formula (i) and a peptide moiety present on the right side thereof.

[Chemical 19]

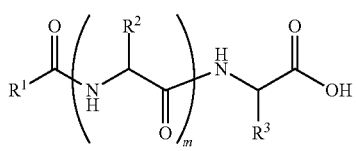

(i)

The present compound was developed as a gelling agent having high biocompatibility and safetiness and capable of providing a cosmetic and the like that demonstrates an improved feel on the skin during use, such as in terms of spreading over the skin and hair and working into to the skin and hair at the time of application, as well as not producing a sticky sensation following application, and in the case of being in the form of a liquid or sol, not dripping during application.

As a result of conducting studies on the present compound, the inventors of the present invention found that, due to the synergistic effects of a polyvalent alcohol and/or glycol ether, the present compound has a function that enhances percutaneous absorption of a drug or various other active ingredients. Although the aforementioned compound acts as a gelling agent in the third present invention, since the percutaneous absorption of an active ingredient typically decreases when gelled, the aforementioned function goes beyond that which would be predicted by a person with ordinary skill in the art.

($R^1$)

In the aforementioned formula (i), $R^1$ represents an aliphatic group having 9 to 23 carbon atoms, and preferably represents an aliphatic group having 13 to 17 carbon atoms.

Examples of the lipid moiety composed of $R^1$ and a carbonyl group adjacent thereto include a decoyl group, dodecoyl group, undecoyl group lauroyl group, dodecylcarbonyl group, myristoyl group, tetradecylcarbonyl group, palmitoyl group, margaroyl group, oleoyl group, elaidoyl group, linoleoyl group, stearoyl group, vaccenoyl group, octadecylcarbonyl group, arachidonoyl group, eicosanoyl group, behenoyl group, erucoyl group, docosylcarbonyl group, lignoceroyl group and nervonoyl group, while preferable examples include a myristoyl group, tetradecylcarbonyl group, palmitoyl group, margaroyl group, oleoyl group, elaidoyl group, linoleoyl group, stearoyl group and vaccenoyl group.

Among these, $R^1CO$ is preferably a palmitoyl group from the viewpoints of ease of production of the lipopeptide and the effect of the active ingredient on promoting percutaneous absorption.

($R^2$ and $R^3$)

In the aforementioned formula (i), $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group.

The number of carbon atoms in the alkyl group having 3 to 7 carbon atoms includes the number of carbon atoms of the branched chain optionally possessed by the alkyl group.

In addition, with respect to the aforementioned —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring. In the case a plurality of $R^2$ and $R^3$ represent —$(CH_2)_n$—X groups, the plurality of n are mutually independent and the plurality of X are mutually independent.

$R^2$ preferably represents a hydrogen atom, methyl group, ethyl group or alkyl group having 3 to 7 carbon atoms that may have a branched chain having 1 to 3 carbon atoms from the viewpoint of the effect of an active ingredient on promoting percutaneous absorption.

Thus, $R^2$ is preferably a hydrogen atom, methyl group, ethyl group, n-propyl group, i-propyl group, n-butyl group, i-butyl group, sec-butyl group or tert-butyl group, more preferably a hydrogen atom, methyl group, i-propyl group, i-butyl group or sec-butyl group, even more preferably a hydrogen atom, methyl group or i-propyl group, and most preferably a hydrogen atom.

$R^3$ preferably represents a hydrogen atom, methyl group or —$(CH_2)_n$—X group, n preferably represents an integer of 1 to 4, X preferably represents an amino group, guanidino group, carbamoyl group or 5-membered cyclic group or 6-membered cyclic group that may have 1 to 3 nitrogen atoms or condensed cyclic group composed of a 5-membered ring and 6-membered ring from the viewpoint of the effect of an active ingredient on promoting percutaneous absorption.

From the same viewpoint, $R^3$ preferably represents a —$(CH_2)_n$—X group, and X preferably represents an amino group, guanidino group, carbamoyl group, pyrrole group, imidazole group, pyrazole group or indole group. Thus, the —$(CH_2)_n$—X group preferably represents an aminomethyl group, 2-aminoethyl group, 3-aminopropyl group, 4-aminobutyl group, carbamoylmethyl group, 2-carbamoylethyl group, 3-carbamoylpropyl group, 2-guanidinoethyl group, 3-guanidinopropyl group, pyrrolemethyl group, 4-imidazolemethyl group, pyrazolemethyl group or 3-indolemethyl group, more preferably represents a 4-aminobutyl group, carbamoylmethyl group, carbamoylethyl group, 3-carbamoylpropyl group, 4-imidazolemethyl group or 3-indolemethyl group, even more preferably represents a 4-aminobutyl group, 4-imidazolemethyl group or 3-methylindole group, and still more preferably represents a 4-imidazolemethyl group.

(m)

The number m of repetitions of units derived from an amino acid that compose the peptide structure in the aforementioned formula (i) represents an integer of 1 to 3. In the case m is 2 or more, the plurality of $R^2$ present are mutually independent. In addition, m is preferably 1 from the viewpoint of the effect of an active ingredient on promoting percutaneous adsorption.

(Lipopeptide)

The useful compound in the third present invention as the previously explained lipopeptide is a compound formed from a lipid moiety and peptide moiety as indicated below. Furthermore, the abbreviation for amino acids is as follows: asparagine (Asn), alanine (Ala), glutamine (Gln), glycine (Gly), valine (Val), histidine (His), lysine (Lys) and leucine (Leu).

Myristoyl-Gly-His, myristoyl-Gly-Lys, myristoyl-Gly-Asn, myristoyl-Gly-Gln, myristoyl-Gly-Gly-His, myristoyl-Gly-Gly-Lys, myristoyl-Gly-Gly-Asn, myristoyl-Gly-Gly-Gln, myristoyl-Gly-Gly-Gly-His, myristoyl-Gly-Gly-Gly-Lys, myristoyl-Gly-Gly-Gly-Asn, myristoyl-Gly-Gly-Gly-Gln, myristoyl-Ala-His, myristoyl-Ala-Lys, myristoyl-Ala-Asn, myristoyl-Ala-Gln, myristoyl-Ala-Ala-His, myristoyl-Ala-Ala-Lys, myristoyl-Ala-Ala-Asn, myristoyl-Ala-Ala-Gln, myristoyl-Ala-Ala-Ala-His, myristoyl-Ala-Ala-Ala-Lys, myristoyl-Ala-Ala-Ala-Asn, myristoyl-Ala-Ala-Ala-Gln, myristoyl-Val-His, myristoyl-Val-Lys, myristoyl-Val-Asn, myristoyl-Val-Gln, myristoyl-Val-Val-His, myristoyl-Val-Val-Lys, myristoyl-Val-Val-Asn, myristoyl-Val-Val-Gln, myristoyl-Val-Val-Val-His, myristoyl-Val-Val-Val-Lys, myristoyl-Val-Val-Val-Asn, myristoyl-Val-Val-Val-Gln, myristoyl-Leu-His, myristoyl-Leu-Lys, myristoyl-Leu-Asn, myristoyl-Leu-Gln, myristoyl-Leu-Leu-His, myristoyl-Leu-Leu-Lys, myristoyl-Leu-Leu-Asn, myristoyl-Leu-Leu-Gln, myristoyl-Leu-Leu-Leu-His, myristoyl-Leu-Leu-Leu-Lys, myristoyl-Leu-Leu-Leu-Asn, myristoyl-Leu-Leu-Leu-Gln;

palmitoyl-Gly-His, palmitoyl-Gly-Lys, palmitoyl-Gly-Asn, palmitoyl-Gly-Gln, palmitoyl-Gly-Gly-His, palmitoyl-Gly-Gly-Lys, palmitoyl-Gly-Gly-Asn, palmitoyl-Gly-Gly-Gln, palmitoyl-Gly-Gly-Gly-His, palmitoyl-Gly-Gly-Gly-Lys, palmitoyl-Gly-Gly-Gly-Asn, palmitoyl-Gly-Gly-Gly-Gln, palmitoyl-Ala-His, palmitoyl-Ala-Lys, palmitoyl-Ala-Asn, palmitoyl-Ala-Gln, palmitoyl-Ala-Ala-His, palmitoyl-Ala-Ala-Lys, palmitoyl-Ala-Ala-Asn, palmitoyl-Ala-Ala-Gln, palmitoyl-Ala-Ala-Ala-His, palmitoyl-Ala-Ala-Ala-Lys, palmitoyl-Ala-Ala-Ala-Asn, palmitoyl-Ala-Ala-Ala-Gln, palmitoyl-Val-His, palmitoyl-Val-Lys, palmitoyl-Val-Asn, palmitoyl-Val-Gln, palmitoyl-Val-Val-His, palmitoyl-Val-Val-Lys, palmitoyl-Val-Val-Asn, palmitoyl-Val-Val-Gln, palmitoyl-Val-Val-Val-His, palmitoyl-Val-Val-Val-Lys, palmitoyl-Val-Val-Val-Asn, palmitoyl-Val-Val-Val-Gln, palmitoyl-Leu-His, palmitoyl-Leu-His, palmitoyl-Leu-Asn, palmitoyl-Leu-Gln, palmitoyl-Leu-Leu-His, palmitoyl-Leu-Leu-Lys, palmitoyl-Leu-Leu-Asn, palmitoyl-Leu-Leu-Gln, palmitoyl-Leu-Leu-Leu-His, palmitoyl-Leu-Leu-Leu-Lys, palmitoyl-Leu-Leu-Leu-Asn, palmitoyl-Leu-Leu-Leu-Gln; and, stearoyl-Gly-His, stearoyl-Gly-Lys, stearoyl-Gly-Asn, stearoyl-Gly-Gln, stearoyl-Gly-Gly-His, stearoyl-Gly-Gly-Lys, stearoyl-Gly-Gly-Asn, stearoyl-Gly-Gly-Gin, stearoyl-Gly-Gly-Gly-His, stearoyl-Gly-Gly-Gly-Lys, stearoyl-Gly-Gly-Gly-Asn, stearoyl-Gly-Gly-Gly-Gln, stearoyl-Ala-His, stearoyl-Ala-Lys, stearoyl-Ala-Asn, stearoyl-Ala-Gln, stearoyl-Ala-Ala-His, stearoyl-Ala-Ala-Lys, stearoyl-Ala-Ala-Asn, stearoyl-Ala-Ala-Gln, stearoyl-Ala-Ala-Ala-His, stearoyl-Ala-Ala-Ala-Lys, stearoyl-Ala-Ala-Ala-Asn, stearoyl-Ala-Ala-Ala-Gin, stearoyl-Val-His, stearoyl-Val-Lys, stearoyl-Val-Asn, stearoyl-Val-Gln, stearoyl-Val-Val-His, stearoyl-Val-Val-Lys, palmitoyl-Val-Val-Asn, stearoyl-Val-Val-Gln, stearoyl-Val-Val-Val-His, stearoyl-Val-Val-Val-Lys, stearoyl-Val-Val-Val-Asn, stearoyl-Val-Val-Val-Gln, stearoyl-Leu-His, stearoyl-Leu-Lys, stearoyl-Leu-Asn, stearoyl-Leu-Gln, stearoyl-Leu-Leu-His, stearoyl-Leu-Leu-Lys, stearoyl-Leu-Leu-Asn, stearoyl-Leu-Leu-Gln, stearoyl-Leu-Leu-Leu-His, stearoyl-Leu-Leu-Leu-Lys, stearoyl-Leu-Leu-Leu-Asn, stearoyl-Leu-Leu-Leu-Gln.

Among these, myristoyl-Gly-His, myristoyl-Gly-Gly-His, myristoyl-Gly-Gly-Gly-His, palmitoyl-Gly-His, palmitoyl-Gly-Gly-His, palmitoyl-Gly-Gly-Gly-His, stearoyl-Gly-His, stearoyl-Gly-Gly-His and stearoyl-Gly-Gly-Gly-His are preferable, and among these, palmitoyl-Gly-His is most preferable.

(Pharmaceutically Acceptable Salt of Lipopeptide)

Although the external use composition of the third present invention comprises (A) a lipopeptide and/or pharmaceutically acceptable salt thereof as previously explained, examples of these salts corresponding to the carboxyl group of the lipopeptide include alkaline metal salts and alkaline earth metal salts such as lithium salts, sodium salts, potassium salts or calcium salts, and in the case $R^3$ is a group having a nitrogen atom such as a group having an imidazole structure, examples of the corresponding salts include inorganic acid salts or organic acid salts such as hydrochlorides, acetates, sulfates, carbonates, phosphates, citrates or succinates.

(Production Method of Lipopeptide and Pharmaceutically Acceptable Salt Thereof)

The method used to produce the previously explained Component (A) (lipopeptide and pharmaceutically acceptable salt thereof) is known, and for example, Component (A) can be produced by linking amino acids in the direction from of the C-terminal to the N-terminal of the amino acids composing a lipopeptide by peptide solid-phase synthesis, reacting the N-terminal of the amino acid located on the end as viewed from the solid phase with the fatty acid to serve as the lipid moiety (such as myristic acid, palmitic acid, stearic acid), and then forming into a salt as necessary.

In addition, a lipopeptide and pharmaceutically acceptable salt thereof can be produced by starting from a fatty acid, reacting this with an amino acid to link the amino acid in the direction from the N-terminal to the C-terminal using a liquid phase method, and then forming into a salt as necessary.

(Content of Component (A))

Although the external use composition of the third present invention comprises a lipopeptide and/or a pharmaceutically acceptable salt thereof as previously explained, the content thereof in the entire external use composition (100% by weight) is 0.05% by weight or more. If the content of Component (A) is less than 0.05% by weight, the effect of an active ingredient (C) on promoting percutaneous absorption to be subsequently described resulting from the addition of Component (A) is unable to be obtained. From the same viewpoint, the content of Component (A) is preferably 0.05% to 10% by weight, while from the viewpoint of achieving favorable gelling of the external use composition by Component (A), the content thereof is more preferably 0.1% to 8% by weight and even more preferably 0.5% to 5% by weight.

In addition, in the third present invention, one type of Component (A) may be used or two or more types may be used in combination.

<(B) Polyvalent Alcohol and/or Glycol Ether>

The external use composition of the third present invention comprises (B) a polyvalent alcohol and/or glycol ether, and components known in the prior art corresponding thereto can be used in the third present invention without any particular limitations.

A polyvalent alcohol having 2 to 6 carbon atoms and 2 to 4 hydroxyl groups can be used for the aforementioned polyvalent alcohol. Specific examples thereof include divalent alcohols such as ethylene glycol, propylene glycol, 1,3-propanediol (trimethylene glycol), 1,2-butylene glycol, 1,3-butylene glycol, 2,3-butylene glycol, 1,4-butanediol (tetramethylene glycol), 2-butene-1,4-diol, 1,5-pentanediol (pentamethylene glycol), 1,2-pentanediol, isoprene glycol (isopentyldiol), hexylene glycol, diethylene glycol or dipropylene glycol, trivalent alcohols such as glycerin or trimethylolpropane, and tetravalent alcohols such as diglycerin, pentaerythritol or 1,2,6-hexanetriole.

Among these, 1,3-butyleneglycol, 1,2-pentanediol, dipropylene glycol, propylene glycol and glycerin are preferable, while 1,3-butylene glycol, 1,2-pentanediol, dipropylene glycol and propylene glycol are more preferable from the viewpoint of the effect of an active ingredient (C) on promoting percutaneous absorption attributable to combined use with Component (A).

Examples of the aforementioned glycol ether include diethylene glycol monomethyl ether, diethylene glycol monoethyl ether (ethoxydiglycol), diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether and dipropylene glycol monopropyl ether.

Among these, diethylene glycol monomethyl ether, diethylene glycol monoethyl ether (ethoxydiglycol), diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether and dipropylene glycol monopropyl ether are preferable from the viewpoint of the action of promoting percutaneous absorption of active ingredient (C).

From the same viewpoint, diethylene glycol monomethyl ether, diethylene glycol monoethyl ether (ethoxydiglycol), diethylene glycol monopropyl ether, ethylene glycol monobutyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether and dipropylene glycol monopropyl ether are more preferable, while diethylene glycol monoethyl ether (ethoxydiglycol) is even more preferable.

The polyvalent alcohol and/or glycol ether (B) explained above is more preferably at least one type selected from the group consisting of ethoxydiglycol, 1,3-butylene glycol, propylene glycol, dipropylene glycol and glycerin, and is particularly preferably ethoxydiglycol, from the viewpoint of synergistic action with Component (A) with respect to percutaneous absorption, while ethoxydiglycol is particularly preferable.

The content of Component (B) in the external use composition of the third present invention in the entire external use composition (100% by weight) is normally 0.0001% to 75% by weight, preferably 0.001% to 60% by weight and even more preferably 5% to 50% by weight from the viewpoint of demonstrating the effects of the third present invention.

<(C) Active Ingredient>

As was previously explained, the external use composition of the third present invention contains a polyvalent alcohol and/or glycol ether (B) and a prescribed amount of lipopeptide and/or a pharmaceutically acceptable salt thereof (A), comprises a terpene (D) to be subsequently described as necessary, and as a result of the combined use of these components, is able to greatly enhance the percutaneous absorption of various types of an active ingredient (C).

Consequently, the external use composition of the third present invention typically comprises various types of active ingredients (C), and active ingredients applied to the skin or having the possibility of being applied to the skin in the future can be used without any particular limitations for the active ingredient (C) used in the third present invention. Although varying according to such factors as the dose of each component or the number of times the external use composition is applied per day, the contents thereof in the external use composition of the third present invention can be suitably set by a person with ordinary skill in the art based on conventionally known matters.

Examples of the aforementioned active ingredient (C) include a disinfectant component, anti-inflammatory component, anti-inflammatory analgesic component, antipruritic component, vitamin, local anesthetic component, moisturizing component, whitening component, antioxidant component, anti-aging component, keratin softening component, cell activating component, circulation promoting component, component having action that prevents and/or repairs damaged DNA, ultraviolet absorbing component, ultraviolet scattering component, astringent component, hair growth component, antihistamine component and antiseptic component.

Although the following lists specific examples thereof, components corresponding to a plurality of components, or components corresponding to bases, carriers or additives to be subsequently described, demonstrate the actions of each type of component corresponding thereto in the third present invention. Furthermore, the action of all corresponding components may not be demonstrated in the case, for example, each component is not incorporated in the amount required for the component to function.

Examples of the aforementioned disinfectant component include terbinafine and salts thereof, butenafine and salts thereof, sulconazole nitrate, luliconazole, miconazole, amorphin hydrochloride, clotrimazole, ketoconazole, bifonazole, neticonazole hydrochloride, lanoconazole, liranaftate, efinaconazole, chlorhexidine, benzalkonium chloride, acrinol, ethanol, benzethonium chloride, cresol, gluconic acid and derivatives thereof, povidone iodine, potassium iodide, iodine, isopropyl methylphenol, triclocarban, triclosan, photosensitizer 101, photosensitizer 201, paraben, phenoxyethanol and alkyldiaminoglycine hydrochloride. Among these, terbinafine and salts thereof, butenafine and salts thereof, benzalkonium chloride, benzethonium chloride, gluconic acid and derivatives thereof, isopropyl methylphenol, triclocarban, triclosan, photosensitizer 101, photosensitizer 201, paraben, phenoxyethanol and alkyldiaminoglycine hydrochloride are preferable, while terbinafine and salts thereof, butenafine and salts thereof, benzalkonium chloride, gluconic acid and derivatives thereof, benzethonium chloride and isopropyl methylphenol are more preferable.

Examples of the aforementioned anti-inflammatory component include components derived from plants (such as comfrey), allantoin, calamine, glycyrrhizic acid and derivatives thereof, glycyrrhetic acid and derivatives thereof, zinc oxide, guaiazulene, pyridoxine hydrochloride and terpene oil. Among these, comfrey leaf extract, allantoin, dipotassium glycyrrhizate and stearyl glycyrrhetinate are preferable.

Examples of the aforementioned anti-inflammatory analgesic component include indomethacin, felbinac, ibuprofen, ibuprofenpiconol, bufexamac, butyl fulfenamate, bendazac, piroxicam and ketoprofen.

Examples of the aforementioned antipruritic component include crotamiton, chlorpheniramine, chlorpheniramine malcate, diphenhydramine, diphenhydramine hydrochloride, diphenhydramine salicylate, nonylic acid vanillylamide, mequitazine, thymol, eugenol, polyoxyethylene lauryl ether and perilla extract.

Examples of the aforementioned vitamins include vitamin A compounds such as retinol, retinol derivatives (such as retinol acetate or retinol palmitate), retinal, retinoic acid, methyl retinoate, ethyl retinoate, retinol retinoate, d-δ-tocopheryl retinoate, α-tocopheryl retinoate or β-tocopheryl retinoate, provitamin A compounds such as β-carotene, α-carotene, γ-carotene, δ-carotene, lycopene, zeaxanthin, cryptoxanthin or echinenone, vitamin E compounds such as α-tocopherol, β-tocopherol, dl-α-tocopherol succinate, calcium dl-α-tocopherol succinate, δ-tocopherol or tocopherol nicotinate, vitamin B2 compounds such as riboflavin, flavin mononucleotide, flavin adenine dinucleotide, riboflavin butyrate, riboflavin tetrabutyrate, riboflavin 5'-phosphate sodium or riboflavin tetranicotinate, and nicotinic acids such as methyl nicotinate, nicotinic acid or nicotinic acid amide.

Additional examples of the aforementioned vitamins include vitamin C compounds such as ascorbyl stearate, L-ascorbyl dipalmitate, ascorbyl tetraisopalmitate (ascorbyl tetra-2-hexyldecanoate), ascorbic acid, sodium ascorbate, dehydroascorbic acid, sodium ascorbyl phosphate, magnesium ascorbyl phosphate or ascorbyl glucoside.

Additional examples of the aforementioned vitamins include vitamin D compounds such as methyl hesperidin, ergocalciferol or cholecalciferol, vitamin K compounds such as phylloquinone or farnoquinone, vitamin B1 compounds such as dibenzoylthiamine, dibenzoylthiamine hydrochloride, thiamine hydrochloride, thiamine cetyl hydrochloride, thiamine thiocyanate, thiamine lauryl hydrochloride, thiamine nitrate, thiamine monophosphate, thiamine diphosphate, thiamine triphosphate, thiamine monophosphate ester phosphate, thiamine monophosphate ester, thiamine diphosphate ester, thiamine triphosphate ester hydrochloride, thiamine triphosphate ester or thiamine triphosphate ester monophosphate, vitamin B6 compounds such as pyridoxine hydrochloride, pyridoxine acetate, pyridoxal hydrochloride, pyridoxal 5'-phosphate or pyridoxamine hydrochloride, vitamin B12 compounds such as cyanocobalamin, hydroxocobalamin or deoxyadenosylcobalamin, folic acid compounds such as folic acid or pteroylglutamic acid, pantothenates such as pantothenic acid, calcium pantothenate, pantothenyl alcohol (panthenol), D-pantetheine, D-pantethine, coenzyme A or pantothenyl ethyl ether, biotins such as biotin or biocytin, and vitamin-like agents such as carnitine, ferulic acid, α-lipoic acid, orotic acid or γ-oryzanol.

Among the vitamins listed above, vitamin C compounds such as ascorbic acid, sodium ascorbyl phosphate, magnesium ascorbyl phosphate or ascorbyl tetraisopalmitate (ascorbyl tetra-2-hexyldecanoate) are preferable.

Examples of the aforementioned local anesthetic component include lidocaine, lidocaine hydrochloride, dibucaine, dibucaine hydrochloride, ethyl aminobenzoate, eucalyptus oil, eugenol and chlorobutanol.

Examples of the aforementioned moisturizing component include components derived from plants (such as lavender, glasswort or cogon), amino acids and derivatives thereof such as alanine, serine, leucine, isoleucine, threonine, glycine, proline, hydroxyproline, glucosamine or theanine, proteins, peptides and hydrogenated forms thereof such as collagen, gelatin or elastin, sugar-alcohols such as sorbitol, phospholipids such as lecithin or hydrogenated lecithin, mucopolysaccharides such as hyaluronic acid, sodium hyaluronate, acetylhyaluronic acid, sodium acetylhyaluronate, heparin or chondroitin, NMF-derived components such as lactic acid, sodium pyrrolidone carboxylate or urea, polyglutamic acid, polymers having a phospholipid polar group such as MPC polymers (such as Lipidure®), polyoxypropylene methyl glucoside, trimethylglycine (betaine), hydroxyethyl urea, acrylic acid-acrylamide-dimethylallyl ammonium chloride copolymers and sorbitol.

Among these, lavender oil, glasswort extract, cogon grass extract, hydrolyzed collagen, hydrolyzed elastin, MPC polymers, trimethylglycine (betaine), hydroxyethyl urea, acrylic acid-acrylamide-dimethylallyl ammonium chloride copolymers, hydrogenated lecithin, hyaluronic acid, sodium hyaluronate, acetylhyaluronic acid, sodium acetylhyaluronate and sorbitol are preferable.

Examples of the aforementioned whitening component include arbutin, hydroquinone, kojic acid, ellagic acid, phytic acid, 4-n-butylresorcinol, chamomile extract, ascorbic acid and derivatives thereof (such as alkyl ethers of ascorbic acid), vitamin E and derivatives thereof, pantothenic acid and derivatives thereof, tranexamic acid and plant components having whitening action (including plant extracts such as grapefruit extract, witch hazel extract, iris root extract or aloe extract, components derived from marine plants such as brown algae extract or Sakhalin kelp extract, and refined oils). Among these, arbutin, hydroquinone, kojic acid and tranexamic acid are preferable.

Examples of the aforementioned antioxidant component include components derived from plants (such as grape, Asian ginseng or comfrey), astaxanthin, proanthocyanidin, tocopherol and derivatives thereof, ascorbic acid and derivatives thereof, hesperidin, glucosyl hesperidin, ergothioneine, sodium hydrogen sulfite, erythorbic acid and salts thereof, flavonoids, glutathione, glutathione peroxidase, glutathione-S-transferase, catalase, superoxide dismutase, thioredoxin, taurine, thiotaurine and hypotaurine.

Among these, grape seed extract, grape leaf extract, Asian ginseng extract, comfrey leaf extract, astaxanthin, proanthocyanidin, tocopherol and derivatives thereof (and particularly δ-tocopherol and α-tocopherol), ascorbic acid and derivatives thereof (and particularly ascorbic acid, sodium ascorbyl phosphate, magnesium ascorbyl phosphate and ascorbyl tetraisopalmitate (ascorbyl tetra-2-hexyldecanoate)), hesperidin, glucosyl hesperidin and ergothioneine are preferable.

Examples of the aforementioned anti-aging component include hydrolyzed soybean protein, retinoids (such as retinol and derivatives thereof, retinoic acid or retinal), pangamic acid, kinetin, ursolic acid, turmeric extract, sphingosine derivatives, silicon, silicic acid, N-methyl-L-serine and mevalonolactone. Among these, artemia extract, hydrolyzed soybean protein, retinol, retinol acetate and retinol palmitate are preferable.

Examples of the aforementioned keratin softening component include lanolin, urea, phytic acid, lactic acid, lactate, glycolic acid, salicylic acid, malic acid and citric acid.

Among these, lactic acid, sodium lactate, glycolic acid and phytic acid are preferable.

Examples of the aforementioned cell activating component include components derived from plants (such as bilberry), amino acids such as γ-aminobutyric acid or ε-aminocaproic acid, vitamins such as retinol and derivatives thereof, thiamine, riboflavin, pyridoxine hydrochloride or pantothenates, α-hydroxy acids such as glycolic acid or lactic acid, tannin, flavonoids, saponin, allantoin and photosensitizer 301. Among these, bilberry leaf extract, retinol, retinol acetate and retinol palmitate are preferable.

Examples of the aforementioned circulation promoting component include components derived from vegetable oils (such as Asian ginseng, Angelica keiskei, mountain arnica, gingko, fennel, Isodonis japonicus, Dutch oak, chamomile, Roman chamomile, Daucus carota sativa, gentian, burdock, rice, Japanese hawthorn, shiitake mushroom, English hawthorn, juniper, cnidium, thyme, clove, citrus unshiu, angelica root, peach kernel, spruce, carrot, garlic, butcher's broom, grape, peony, horse chestnut, lemon balm, yuzu, coix, rosemary, rose hip, citrus unshiu, angelica, spruce, peach, apricot, walnut or corn), tocopherol nicotinate, glucosyl hesperidin and hesperidin.

Among these, Asian ginseng extract, tocopherol nicotinate, glucosyl hesperidin and hesperidin are preferable.

Examples of the aforementioned component having action that prevents and/or repairs damaged DNA include components derived from animals (such as artemia), components derived from plants (such as cat's claw), and nucleic acid components such as DNA, DNA salts, RNA and RNA salts. Among these, artemia extract and DNA-Na are preferable.

Examples of the aforementioned ultraviolet absorbing component include 2-ethylhexyl para-methoxycinnamate, hexylethyl 2-[4-(diethylamino)-2-hydroxybenzoyl]benzoate, 2,4,6-tris[4-(2-ethylhexyloxycarbonyl)anilino]-1,3,5-triazine, 2-ethylhexyl dimethoxybenzylidene oxoimidazolidine propionate and 2,4-bis[{4-(2-ethylhexyloxy)-2-hydroxy}-phenyl]-6-(4-methoxyphenyl)-1,3,5-triazine.

Among these, 2-ethylhexyl para-methoxycinnamate, hexylethyl 2-[4-(diethylamino)-2-hydroxybenzoyl]benzoate and 2,4,6-tris[4-(2-ethylhexyloxycarbonyl)anilino]-1,3,5-triazine are preferable.

Examples of the aforementioned ultraviolet scattering component include inorganic compounds such as zinc oxide, titanium oxide, iron oxide, cerium oxide, zirconium oxide, titanium silicate, zinc silicate, silicic anhydride, cerium silicate or hydrated silicic acid, ultraviolet scattering components obtained by coating these inorganic compounds with an inorganic powder such as hydrated silicic acid, aluminum hydroxide, mica or talc, ultraviolet scattering components obtained by compounding into a resin powder such as polyamide, polyethylene, polyester, polystyrene or nylon, and ultraviolet scattering components obtained by treating these inorganic compounds with silicone oil or fatty acid aluminum salts. Among these, inorganic compounds such as zinc oxide, titanium oxide or iron oxide, and these inorganic compounds coated with an inorganic powder, such as aluminum hydroxide, hydrated silicic acid, mica or talc, or silicone oil are preferable.

Examples of the aforementioned astringent component include metal salts such as alum, aluminum chlorohydrate, aluminum chloride, allantoin aluminum salt, zinc sulfate or potassium aluminum sulfate, and organic acids such as tannic acid, citric acid, lactic acid or succinic acid.

Among these, alum, aluminum chlorohydrate, aluminum chloride, allantoin aluminum salt, potassium aluminum sulfate and tannic acid are preferable.

Examples of the aforementioned hair growth component include procyanidin, dipotassium glycyrrhizate, carpronium chloride, cephalothin, hinokitiol, L-hydroxyproline, acetyl hydroxyproline, fucoidan, capsicum tincture, cephalothin, sueruchianin, panax ginseng, flavonosteroid, minoxidil, FGF-10, Isodonis japonicus extract, Swertia herb extract, ribbon weed extract, five-leaf ginseng extract, St. John's wort extract, gentian extract, sage extract, peppermint extract, hop extract, coix extract, persimmon leaf extract, rehmannia root extract, carrot extract, Bohdi tree extract, moutan bark extract and tree bark extract.

Examples of the aforementioned antihistamine component include ethanolamine-based compounds such as diphenhydramine, diphenhydramine hydrochloride or dimenhydrinate, propylamine-based compounds such as chlorpheniramine maleate, phenothiazine-based compounds such as promethazine hydrochloride, piperazine-based compounds such as hydroxyzine, piperidine-based compounds such as cyproheptadine hydrochloride, epinastine hydrochloride, loratadine and fexofenadine hydrochloride. In addition, pharmaceutically acceptable salts of each compound can also be used in addition to hydrochloride forms thereof. Among these, diphenhydramine, diphenhydramine hydrochloride and chlorpheniramine maleate are preferable.

Examples of the aforementioned antiseptic component include benzoic acid, sodium benzoate, dehydroacetic acid, sodium dehydroacetate, isobutyl paraoxybenzoate, isopropyl paraoxybenzoate, butyl paraoxybenzoate, ethyl paraoxybenzoate, propyl paraoxybenzoate, benzyl paraoxybenzoate, methyl paraoxybenzoate and phenoxyethanol. Among these, methyl paraoxybenzoate, propyl paraoxybenzoate and phenoxyethanol are preferable.

One type of the previously explained active ingredient (C) may be used alone in the external use composition of the third present invention or two or more types may be used in combination.

<(D) Terpene>

Although the third present invention enhances the percutaneous absorption of an active ingredient (C) due to synergistic action between the previously explained Component (A) and Component (B), the aforementioned percutaneous absorption is further enhanced by incorporating a terpene (D) in the external use composition of the third present invention.

Examples of the aforementioned terpene (D) include monoterpenes such as camphor, menthol, borneol, eugenol, cineole, thymol, bisabolol, α-pinene, linalool, menthone, linalyl acetate, hinokitiol, limonene, geraniol, nerol, citral, citronellol, mint, myrcene, terpineol, carvone, ionone, camphor, borneol, cadinene or phellandrene, sesquiterpenes such as elemene, cadinol, candinene, farnesol, nerolidol, humulene (clove) or santonin, diterpenes such as phytol, abietic acid or taxol, sesterterpenes such as geranyl farnesol extracted primarily from microorganisms, lower plants and insects such as lichens, and lower animals such as sponges, triterpenes such as lupane, oleanane, ursane, boswellic acid, limonin, ursolic acid, squalene, hopane or betulinic acid, and tetraterpenes such as carotinoids (carotenoids) or lycopene.

Among these, camphor or menthol is preferable, and menthol is more preferable. Both natural and synthetic monoterpenes can be used, and may be in the d-form, l-form or dl-form. In addition, these monoterpenes may also be incorporated in the external use composition of the third present invention in the form of refined oils of eucalyptus oil, peppermint oil, clove oil, cinnamon oil, peppermint oil, mint oil, tea tree oil, chamomile oil, rosemary oil, lemon oil, orange oil, thyme oil, sage oil or clove oil.

One type of the terpene (D) explained above may be used alone in the external use composition of the third present invention or two or more types may be used in combination. In addition, the content of terpene (D) in the aforementioned external use composition is normally 0.01% to 10% by weight, and from the viewpoint of the synergistic action of Component (C) with Component (A) and Component (B) on the effect promoting percutaneous absorption, is preferably 0.1% to 5% by weight.

Embodiment of Formulation of External Use Composition

The external use composition of the third present invention can be an external use composition in the form of a pharmaceutical, quasi drug or cosmetic by mixing essential components thereof and an active ingredient (C) as previously explained in accordance with ordinary methods together with a base, carrier and, as necessary, an additive to be subsequently described, that are normally used in pharmaceuticals, quasi drugs or cosmetics.

Examples of the aforementioned base or carrier include hydrocarbons such as liquid paraffin, squalane, Vaseline, gelling hydrocarbons (such as plastibase), ozokerite, α-olefin oligomers or light liquid paraffin, silicone oils such as methylpolysiloxane, highly polymerized methylpolysiloxane, cyclic silicone, alkyl-modified silicone, amino-modified silicone, polyether-modified silicone, polyglycerin-modified silicone, silicone-alkyl chain co-modified polyether-modified silicone, silicone-alkyl chain co-modified polyglycerin-modified silicone, polyether-modified branched silicone, polyglycerin-modified branched silicone, acrylsilicone, phenyl-modified silicone or silicone resin, oils such as palm oil, olive oil, rice bran oil or shea butter, waxes such as jojoba oil, beeswax, candelilla wax or lanolin, higher alcohols such as cetanol, cetostearyl alcohol, stearyl alcohol, behenyl alcohol, octyl dodecanol, isostearyl alcohol, phytosterol or cholesterol, cellulose derivatives such as ethyl cellulose, hydroxypropyl cellulose or hydroxypropyl methyl cellulose, polyvinylpyrrolidone, carrageenan, polyvinylbutyrate, polyethylene glycol, dioxane, butylene glycol polyester adipate, esters such as diisopropyl adipate, isopropyl myristate, octyldodecyl myristate, isopropyl palmitate, cetyl palmitate, isononyl isononanoate or pentaerythritol tetra(2-ethylhexanoate), polysaccharides such as dextrin or maltodextrin, vinyl-based polymers such as carboxyvinyl polymer or alkyl-modified carboxyvinyl polymer, lower alcohols such as ethanol or isopropanol, and water.

In the case the external use composition of the third present invention comprises a polyvalent alcohol, the polyvalent alcohol may also fulfill the role of a base or carrier.

In the case the external use composition of the third present invention comprises a base or carrier other than water, the base or carrier is preferably a hydrocarbon, oil, esters, silicone oil or waxes, and more preferably an ester or silicone oil. Among these components, glyceryl tri-2-ethylhexanoate, dimethicone, cyclomethicone, polyether-modified silicone and polyglycerin-modified silicone are more preferable.

One type of the previously explained base or carrier can be used alone or two or more types can be used in combination, and the amounts used thereof are suitably selected from known ranges by a person with ordinary skill in the art.

<Form>

There are no particular limitations on the form of the external use composition of a pharmaceutical preparation, and examples thereof include an ointment, liquid, suspension, emulsion (milky lotion and cream), gel, liniment, lotion, aerosol, tape or poultice. These preparations can be produced in accordance with methods described in the general rules of preparations of the 16th edition of the Japanese Pharmacopoeia.

There are no particular limitations on the form of the external use composition of a quasi drug or cosmetic preparation, and examples thereof include a beauty lotion, essence, milky lotion, cream, gel, ointment, spray, hand cream, body lotion, body cream, lip cream or sunscreen. These preparations can be produced in accordance with ordinary methods.

<Additives>

Additives known to be added to a pharmaceutical, quasi drug or cosmetic, such as a percutaneous absorption promoter, stabilizer, antioxidant, colorant, pearling agent, dispersant, chelating agent, pH adjuster, preservative, thickener or irritation reducing agent, can be added to the external use composition of the third present invention within a range that does not impair the effects of the third present invention.

One type of these additives can be used alone or two or more types can be used in combination. Moreover, although the following additives corresponding to a plurality of components demonstrate the action of that plurality of components, they may not demonstrate a plurality of actions in certain cases.

Examples of the aforementioned percutaneous absorption promoter include amino compounds such as dimethylsulfoxide, dimethylformamide, methyldecylsulfoxide or diisopropanolamine, azacycloalkan-2-one derivatives such as 1-dodecylazacycloheptan-2-one, organic acid esters such as isopropyl myristate, octyldecyl myristate, isopropyl palmitate, cetyl palmitate, diisopropyl adipate, propylene glycol monocaprylate or propylene glycol dicaprylate, fatty acids having 6 to 20 carbon atoms such as oleic acid, stearic acid or palmitic acid, fatty acid ethers, alkylpyrrolidones such as 2-hydroxyethylpyrrolidone, hydrophilic polyethers such as polyethylene glycol or polypropylene glycol, aliphatic alcohols in the manner of higher alcohols such as cetanol, cetostearyl alcohol, stearyl alcohol, behenyl alcohol, oleyl alcohol, octyldecanol, isostearyl alcohol, phytosterol or cholesterol, and lower alcohols such as ethanol or isopropanol, salicylic acids, benzyl alcohol, squalane, castor oil, surfactants involving anionic surfactants such as polyoxyalkylene alkyl (or alkenyl) ether sulfates, alkyl (or alkenyl) sulfates, higher fatty acid salts, ether carboxylates, amide ether carboxylates, alkyl phosphate esters salts, N-acylamino acid salts, polyoxyalkylene fatty acid amide ether sulfates, acylated isethionates or acylated taurates, nonionic surfactants such as amine oxides, glycerin fatty acid esters, sorbitan fatty acid esters, alkyl saccharides, polyoxyalkylene alkyl ethers, fatty acid alkanol amides and polyoxyalkylene hydrogenated castor oil, cationic surfactants such as mono- or di-long chain alkyl quaternary ammonium salts having a linear or branched long chain alkyl group to which alkylene oxide may or may not be added, and amphoteric surfactants such as carbobetaine, sulfobetaine, imidazolinium betaine or betaine amide, lecithin, and Azon.

Examples of the aforementioned stabilizer include magnesium sulfate, sodium polyacrylate, dibutylhydroxytoluene and butylhydroxyanisole.

Examples of the aforementioned antioxidant include dibutylhydroxytoluene, butylhydroxyanisole, sorbic acid sodium sulfite, ascorbic acid, erythorbic acid or L-cysteine hydrochloride.

Examples of the aforementioned colorant include inorganic pigments and natural pigments.

Examples of the aforementioned pearling agent include ethylene glycol distearate, ethylene glycol monostearate and triethylene glycol distearate.

Examples of the aforementioned dispersant include sodium pyrophosphate, sodium hexametaphosphate, polyvinyl alcohol, polyvinylpyrrolidone, methyl vinyl ether-maleic anhydride copolymer and organic acids.

Examples of the aforementioned chelating agent include ethylenediamine tetraacetic acid (edetic acid), ethylenediamine tetraacetate (such as sodium salt (sodium edetate: Japanese Pharmacopeia, EDTA-2Na) or potassium salt), phytic acid, gluconic acid, polyphosphoric acid or metaphosphoric acid. Among these, sodium edetate is preferable.

Examples of the aforementioned pH adjuster include inorganic acids (such as hydrochloric acid or sulfuric acid), organic acids (such as lactic acid, sodium lactate, citric acid, sodium citrate, succinic acid or sodium succinate), inorganic bases (such as potassium hydroxide or sodium hydroxide), and organic bases (such as triethanolamine, diisopropanolamine or triisopropanolamine).

Examples of the aforementioned preservative include benzoic acid, sodium benzoate, dehydroacetic acid, sodium dehydroacetate, isobutyl paraoxybenzoate, isopropyl paraoxybenzoate, butyl paraoxybenzoate, ethyl paraoxybenzoate, propyl paraoxybenzoate, benzyl paraoxybenzoate, methyl paraoxybenzoate and phenoxyethanol.

Examples of the aforementioned thickener include cellulose-based thickeners such as methyl cellulose, ethyl cellulose, hydroxyethyl cellulose, hydroxymethyl cellulose, hydroxypropyl cellulose, hydroxypropyl methyl cellulose, carboxymethyl cellulose or carboxyethyl cellulose, gua gum, pectin, pullulan, gelatin, locust bean gum, carrageenan, agar, gellan gum, xanthan gum, polyvinyl alcohol, polyvinylpyrrolidone, carboxyvinyl polymer, acrylic acid-alkyl methacrylate copolymer, polyethylene glycol, bentonite, alginic acid, propylene glycol alginate, Macrogol, sodium chondroitin sulfate, hyaluronic acid, sodium hyaluronate, hydroxyethyl acrylate-sodium acryloyldimethyl taurate copolymer and ammonium acryloyldimethyl taurate-vinylpyrrolidone copolymer.

Examples of the aforementioned irritation reducing agent include licorice extract, gum arabic, polyvinylpyrrolidone and sodium alginate.

<Percutaneous Application>

The external use composition of the third present invention is composed of each of the aforementioned components and is used in the form of a prescribed preparation as necessary. This composition comprises a polyvalent alcohol and/or glycol ether (B) and a prescribed amount of a lipopeptide and/or pharmaceutically acceptable salt (A), and demonstrates a superior percutaneous absorption promoting action on an active ingredient (C) due to the synergistic action thereof. More specifically, in the case of having carried out an absorption test using a Franz cell and a Strat-M™ membrane in the examples to be subsequently described, the percutaneously absorbed amount of active ingredient (C) increases in comparison with not incorporating Component (A). In addition, as is shown in the examples to be subsequently described, a percutaneous absorption promoting action is not demonstrated by ordinary known gelling agents.

Although the external use composition of the third present invention is applied to the skin, the skin here refers to the tissue covering the surface of an animal body, such as body skin, mucous membranes (such as the nasal mucosa or oral mucosa) or scalp. Moreover, gums are also included in skin in the third present invention.

In addition, examples of methods used to apply to skin include coating, spraying or the use of a tape. This applies similarly to the cosmetic of the third present invention indicated below.

<Production Method of External Use Composition>

There are no particular limitations on the method used to produce the external use composition of the third present invention, and can be produced in accordance with ordinary methods by suitably selecting and incorporating essential components as well as an active ingredient (C), terpene (D)

and various other components required to produce the external use composition (such as the aforementioned base, carrier or additives). Forms of the resulting external use composition of the third present invention are as previously described.

[Cosmetic]

Since the external use composition of the third present invention may contain an active ingredient in the form of a component such as a vitamin, moisturizing component or whitening component incorporated in cosmetics, it can be preferably used as a cosmetic. In addition, according to the third present invention, since the percutaneous absorption of the active ingredient (C) is enhanced, the function of a cosmetic, which has been given functionality by incorporating the active ingredient (C), can be further enhanced.

In addition to those examples of preparation forms of the external use composition of the third present invention that apply to preparation forms of cosmetics, various types of conventionally known preparation forms used for the preparation form of a cosmetic can be used without any particular limitations for the preparation form of the cosmetic of the third present invention.

[Method for Enhancing Percutaneous Absorption of Active Ingredient in Percutaneous Absorption Promoting Composition and External Use Composition]

As was previously described, the external use composition of the third present invention comprises a lipopeptide and/or a pharmaceutically acceptable salt thereof (A) and a polyvalent alcohol and/or glycol ether (B), and is able to enhance the percutaneous absorption of various types of an active ingredient (C). Thus, this composition can be used as a novel composition promoting percutaneous absorption for enhancing percutaneous absorption of various types of an active ingredient (C).

In addition, the third present invention involving the combined use of the aforementioned lipopeptide and/or pharmaceutically acceptable salt thereof (A) and the polyvalent alcohol and/or glycol ether (B) can also be perceived to be a method for enhancing the percutaneous absorption of an active ingredient (C) in an external use composition by incorporating a prescribed lipopeptide and/or pharmaceutically acceptable salt thereof (A) in a conventional external use composition comprising an active ingredient (C) and a polyvalent alcohol and/or glycol ether (B).

Furthermore, although a "lipopeptide and/or pharmaceutically acceptable salt thereof (A)" is used in this method, there are no particular limitations on the method used to incorporate this component, the polyvalent alcohol and/or glycol ether (B) and the active ingredient (C) (with respect to the order and conditions thereof). It is only required that the lipopeptide and/or pharmaceutically acceptable salt thereof (A), the polyvalent alcohol and/or glycol ether (B) and the active ingredient (C) be present together in the external use composition as a result of carrying out the aforementioned method. For example, these three components (and other components as necessary) may be incorporated (mixed) simultaneously or these components may be incorporated sequentially in any arbitrary order.

[Composition for Instillation]

The composition for instillation of the third present invention comprises a medicinal component, the previously explained polyvalent alcohol and/or glycol ether (B), and a lipopeptide and/or pharmaceutically acceptable salt thereof (A) represented by the aforementioned formula (i), and the content of the aforementioned Component (A) is 0.05% by weight or more.

Since nearly almost of medicinal components administered by instillation that migrate inside the eye migrate into the eye by passing through the cornea, corneal permeability of the medicinal component is extremely important in terms of developing a composition for instillation. The composition for instillation of the third present invention comprises a polyvalent alcohol and/or glycol ether (B) and a prescribed amount of a lipopeptide and/or pharmaceutically acceptable salt thereof (A), and corneal permeability of the medicinal component is promoted due to the synergistic action thereof.

There are no particular limitations on the aforementioned medicinal component provided it is applied to an ophthalmic solution or has the possibility of being applied to an ophthalmic solution in the future. Specific examples thereof include those corresponding to medicinal components among the components listed as examples of an active ingredient in the external use composition of the third present invention. Namely, examples thereof include a disinfectant component, anti-inflammatory component, vitamin, local anesthetic component, anti-allergic component, cell activating component, circulation promoting component, antihistamine component and antiseptic component.

[Percutaneously Administered Drug]

The percutaneously administered drug of the third present invention comprises a medicinal component, a lipopeptide represented by the aforementioned formula (i) and/or pharmaceutically acceptable salt thereof (A) and the previously explained polyvalent alcohol and/or glycol ether (B), and the content of the aforementioned Component (A) is 0.05% by weight or more.

There are no particular limitations on the aforementioned medicinal component provided it is applied to the skin or has the possibility of being applied to the skin in the future. Specific examples thereof include those corresponding to medicinal components among the components listed as examples of an active ingredient in the external use composition of the third present invention. Namely, examples thereof include a disinfectant component, anti-inflammatory component, anti-inflammatory analgesic component, antipruritic component, vitamins, local anesthetic component, moisturizing component, antioxidant component, cell activating component, circulation promoting component, component having action that prevents and/or repairs damaged DNA, astringent component, hair growth component, antihistamine component and antiseptic component.

Preparation forms conventionally used as preparation forms of a percutaneously administered drug can be used without any particular limitations in the third present invention for the preparation form of the percutaneously administered drug of the third present invention. Specific examples thereof include externally applied solids, externally applied powders, liniments, lotions, sprays, aerosols, pump sprays, ointments, creams, gels, tapes and poultices described in the general rules for preparations of the 16th edition of the Japanese Pharmacopoeia. These preparations can be produced in accordance with methods described in the general provision for preparations of the 16th edition of the Japanese Pharmacopoeia.

Examples of the Third Present Invention

Although the following provides a more detailed explanation of the third present invention through examples thereof, the third present invention is not limited thereby.

Furthermore, the units of numerical values are in percent by weight unless specifically indicated otherwise.

Example 3-1 and Comparative Example 1

Each external use composition was prepared according to ordinary methods in accordance with the compositions shown in Table 3-1 below.

TABLE 3-1

|  |  | Example 3-1 | Comp. Ex. 3-1 |
|---|---|---|---|
| (A) Lipopeptide | Pal-GH | 0.5% | — |
| (B) Polyvalent alcohol and/or glycol ether | Ethoxydiglycol | 20% | 20% |
|  | 1,3-butylene glycol | 39.5% | 40% |
| (C) Active ingredient | Ascorbic acid | 20% | 20% |
| Other | Purified water | 20% | 20% |
|  | Total | 100% | 100% |

* Pal-GH is the abbreviation of palmitoyl-Gly-His.

<Percutaneous Absorption Test of Ascorbic Acid (Vitamin C)>

The percutaneous absorption of ascorbic acid of the external use compositions prepared above was confirmed by measuring over time using a Franz cell in the infinite closed system.

More specifically, a stirrer was placed in a Franz cell (PermeGear, jacketed still-standing type with flat jacket, clear, 9 mm, 5 mL, permeation area: 0.64 square inches) followed by pouring in 5 mL of purified water, positioning a Strat-M™ membrane between the Franz cell and ground glass donor, and holding in position with clips. In order to ensure infinite closed system, a test sample (external use composition) was placed on the glass donor and changes caused by evaporation of the sample were prevented using aluminum foil.

The temperature of a constant temperature bath was set to 37° C. and the Franz cell and the constant temperature bath were connected in series with a silicon tube so as to maintain the reservoir solution at a constant temperature. Each Franz cell was placed in a stirrer and the test was started by initiating stirring at 400 rpm. 200 μL aliquots of the reservoir solution were sampled at certain times after the start of stirring (30 minutes, 1 hour, 2 hours, 4 hours and 8 hours) followed by measurement of the VC content in the reservoir solution by HPLC. Detection of ascorbic acid (Wako Pure Chemical Industries) by HPLC was carried out at a wavelength of 270 nm using an ultraviolet absorptiometer followed by calculating content from a calibration curve.

The results of the aforementioned percutaneous absorption test are shown in FIG. 3-1. According to FIG. 3-1, in the case of the external use composition of the third present invention combining the use of a polyvalent alcohol and/or glycol ether with a prescribed amount of a lipopeptide and/or pharmaceutically acceptable salt thereof, the amount of percutaneously absorbed ascorbic acid (active ingredient) was extremely large in comparison with the external use composition of Comparative Example 3-1 not comprising lipopeptide, and statistically significant differences were observed at each measurement point.

Examples 3-2 to 3-7 and Comparative Examples 3-2 to 3-9

The compositions described in the following Tables 3-2 and 3-3 were prepared in the same manner as in the case of Example 3-1 and Comparative Example 3-1.

TABLE 3-2

|  |  | Incorporated Amount (%) | | | | | |
|---|---|---|---|---|---|---|---|
|  | Component | Ex. 3-2 | Ex. 3-3 | Ex. 3-4 | Ex. 3-5 | Ex. 3-6 | Ex. 3-7 |
| (A) Lipopeptide | Pal-GH | 0.5 | 0.5 | 0.5 | 0.5 | 0.5 | 0.5 |
| (B) Polyvinyl alcohol and/or glycol ether | 1,3-butylene glycol | 39.5 | 39.5 | 58.5 | 29.5 | 49.5 | 59.5 |
|  | Ethoxydiglycol | — | — | — | 30.0 | 10.0 | — |
|  | Propylene glycol | 20.0 | — | — | — | — | — |
|  | Dipropylene glycol | — | 20.0 | — | — | — | — |
| (C) Active ingredient | Ascorbic acid | 20.0 | 20.0 | 20.0 | 20.0 | 20.0 | 20.0 |
| (D) Terpenes | l-menthol | — | — | 1.0 | — | — | — |
| Other | Purified water | 20.0 | 20.0 | 20.0 | 20.0 | 20.0 | 20.0 |
|  | Total | 100.0 | 100.0 | 100.0 | 100.0 | 100.0 | 100.0 |

TABLE 3-3

|  |  | Incorporated Amount (%) | | | | | | | |
|---|---|---|---|---|---|---|---|---|---|
|  | Component | Comp. Ex. 3-2 | Comp. Ex. 3-3 | Comp. Ex. 3-4 | Comp. Ex. 3-5 | Comp. Ex. 3-6 | Comp. Ex. 3-7 | Comp. Ex. 3-8 | Comp. Ex. 3-9 |
| (A) Lipopeptide | Pal-GH | — | — | — | — | — | — | 0.5 | — |
| (B) Polyvalent alcohol and/or glycol ether | 1,3-butylene glycol | 40.0 | 40.0 | 59.0 | 30.0 | 50.0 | 60.0 | — | — |
|  | Ethoxydiglycol | — | — | — | 30.0 | 10.0 | — | — | — |
|  | Propylene glycol | 20.0 | — | — | — | — | — | — | — |

TABLE 3-3-continued

|  | Component | Incorporated Amount (%) | | | | | | | |
|---|---|---|---|---|---|---|---|---|---|
|  |  | Comp. Ex. 3-2 | Comp. Ex. 3-3 | Comp. Ex. 3-4 | Comp. Ex. 3-5 | Comp. Ex. 3-6 | Comp. Ex. 3-7 | Comp. Ex. 3-8 | Comp. Ex. 3-9 |
|  | Dipropylene glycol | — | 20.0 | — | — | — | — | — | — |
| (C) Active ingredient | Ascorbic acid | 20.0 | 20.0 | 20.0 | 20.0 | 20.0 | 20.0 | 20.0 | 20.0 |
| (D) Terpene | l-menthol | — | | | | | | | |
| Other | Purified water | 20.0 | 20.0 | 20.0 | 20.0 | 20.0 | 20.0 | 79.5 | 80.0 |
|  | Total | 100.0 | 100.0 | 100.0 | 100.0 | 100.0 | 100.0 | 100.0 | 100.0 |

<Absorption Test of Ascorbic Acid Percutaneous>

Percutaneous absorption of ascorbic acid (amount at 8 hours after initiating stirring of the Franz cell) was determined for external use compositions obtained in the same manner as the case of Example 3-1 and Comparative Example 3-1.

The results are shown in FIGS. 3-2 to 3-7. According to FIGS. 3-2 to 3-7, in the case of the external use compositions of the third present invention combining the use of a prescribed amount of a lipopeptide and a polyvalent alcohol and/or glycol ether, the amount of percutaneously absorbed ascorbic acid (active ingredient) was determined to be statistically significantly higher in comparison with the external use compositions of the comparative examples not comprising lipopeptide.

In addition, although Example 3-4 (FIG. 3-4) is a composition in which I-menthol (Wako Pure Chemical Industries) was added to Example 3-7 (FIG. 3-7), the addition of this component was determined to greatly increase the absorbed amount of ascorbic acid.

Moreover, based on the results for Comparative Example 3-8 (FIG. 3-7), even if a prescribed amount of lipopeptide is contained, the percutaneously absorbed amount of ascorbic acid was determined to not increase unless this was used in combination with a polyvalent alcohol and/or glycol ether.

Examples 3-8 to 3-11 and Comparative Examples 3-10 and 3-11

Compositions described in the following Table 3-4 were prepared in the same manner as in the case of Example 3-1 and Comparative Example 3-1.

<Ascorbic Acid Percutaneous Absorption Test>

Percutaneous absorption of ascorbic acid (amount at 8 hours after initiating stirring of the Franz cell) was determined for external use compositions obtained in the same manner as the case of Example 3-1 and Comparative Example 3-1.

The results are shown in FIG. 3-8. According to FIG. 3-8, in the case of not incorporating a lipopeptide and/or pharmaceutically acceptable salt thereof (Comparative Example 3-10) and in the case the content thereof is 0.01% by weight (Comparative Example 3-11), percutaneous absorption of ascorbic acid was determined to not be promoted, while in the case of the content thereof being 0.1% by weight or more (Examples 3-8 to 3-11), transcutaneous absorption was determined to have been promoted.

Example 3-12 and Comparative Examples 3-12 to 3-14

Compositions described in the following Table 3-5 were prepared in the same manner as in the case of Example 3-1 and Comparative Example 3-1.

TABLE 3-5

|  | Component | Incorporated Amount (%) | | | |
|---|---|---|---|---|---|
|  |  | Ex. 3-12 | Comp. Ex. 3-12 | Comp. Ex. 3-13 | Comp. Ex. 3-14 |
| (A) Lipopeptide | Pal-GH | 0.5 | — | — | — |
| (B) Polyvalent alcohol and/or glycol ether | 1,3-butylene glycol | 39.5 | 39.5 | 39.5 | 40.0 |
|  | Ethoxydiglycol | 10.0 | 10.0 | 10.0 | 10.0 |

TABLE 3-4

|  | Component | Incorporated Amount (%) | | | | | |
|---|---|---|---|---|---|---|---|
|  |  | Comp. Ex. 3-10 | Comp. Ex. 3-11 | Ex. 3-8 | Ex. 3-9 | Ex. 3-10 | Ex. 3-11 |
| (A) Lipopeptide | Pal-GH | — | 0.01 | 0.1 | 0.5 | 5.0 | 10.0 |
| (B) Polyvalent alcohol and/or glycol ether | 1,3-butylene glycol | 50.0 | 49.99 | 49.9 | 49.5 | 45.0 | 40.0 |
|  | Ethoxydiglycol | 10.0 | 10.0 | 10.0 | 10.0 | 10.0 | 10.0 |
| (C) Active ingredient | Ascorbic acid | 20.0 | 20.0 | 20.0 | 20.0 | 20.0 | 20.0 |
| Other | Purified water | 20.0 | 20.0 | 20.0 | 20.0 | 20.0 | 20.0 |
|  | Total | 100.0 | 100.0 | 100.0 | 100.0 | 100.0 | 100.0 |

TABLE 3-5-continued

|  | | Incorporated Amount (%) | | | |
| --- | --- | --- | --- | --- | --- |
| | Component | Ex. 3-12 | Comp. Ex. 3-12 | Comp. Ex. 3-13 | Comp. Ex. 3-14 |
| (C) Active ingredient | VC ethyl | 5.0 | 5.0 | 5.0 | 5.0 |
| Other gelling agent | Gellan gum | — | 0.5 | — | — |
| | Agar | — | — | 0.5 | — |
| Other | Purified water | 45.0 | 45.0 | 45.0 | 45.0 |
| | Total | 100.0 | 100.0 | 100.0 | 100. |

<Percutaneous Absorption Test of 3-O-Ethyl Ascorbic Acid (VC Ethyl, Tokyo Chemical Industry)>

Percutaneous absorption of VC Ethyl (amount at 8 hours after initiating stirring of the Franz cell) was determined for external use compositions obtained in the same manner as the case of Example 3-1 and Comparative Example 3-1. Detection of VC Ethyl by HPLC was carried out at a wavelength of 245 nm using an ultraviolet absorptiometer followed by calculating content from a calibration curve.

The results are shown in FIG. 3-9. According to FIG. 3-9, the combination of a prescribed amount of lipopeptide and/or pharmaceutically acceptable salt thereof and a polyvalent alcohol and/or glycol ether was determined to statistically significantly increase the percutaneously absorbed amount of VC Ethyl.

In addition, according to the results for Comparative Examples 3-12 and 3-13 in FIG. 3-9, the percutaneous absorption promoting effect in the case of using the lipopeptide and/or pharmaceutically acceptable salt thereof of the third present invention was determined to be unable to be obtained in the case of using conventionally known gelling agents in the form of gellan gum (KelcoGel HM, DSP Gokyo Food & Chemical) and agar (Ina Agar, Ina Food Industry).

Example 3-13 and Comparative Examples 3-15 and 3-16

Compositions described in the following Table 3-6 were prepared in the same manner as in the case of Example 3-1 and Comparative Example 3-1.

TABLE 3-6

|  | | Incorporated Amount (%) | | |
| --- | --- | --- | --- | --- |
| — | Component | Ex. 3-13 | Comp. Ex. 3-15 | Comp. Ex. 3-16 |
| (A) Lipopeptide | Pal-GH | 0.5 | — | — |
| (B) Polyvalent alcohol and/or glycol ether | 1,3-butyene glycol | 68.5 | 68.5 | 69.0 |
| | Ethoxydiglycol | 10.0 | 10.0 | 10.0 |
| (C) Active ingredient | Terbinafine hydrochloride | 1.0 | 1.0 | 1.0 |
| Known gelling agent | Gellan gum | — | 0.5 | — |
| Other | Purified water | 20.0 | 20.0 | 20.0 |
| | Total | 100.0 | 100.0 | 100.0 |

<Percutaneous Absorption Test of Terbinafine Hydrochloride>

Percutaneous absorption of terbinafine hydrochloride (amount at 8 hours after initiating stirring of the Franz cell) was determined for external use compositions obtained in the same manner as the case of Example 3-1 and Comparative Example 3-1. Detection of terbinafine hydrochloride by HPLC was carried out at a wavelength of 282 nm using an ultraviolet absorptiometer followed by calculating content from a calibration curve.

The results are shown in FIG. 3-10. According to FIG. 3-10, the combination of a prescribed amount of lipopeptide and/or pharmaceutically acceptable salt thereof and a polyvalent alcohol and/or glycol ether was determined to statistically significantly increase the percutaneously absorbed amount of terbinafine hydrochloride.

In addition, according to the results for Comparative Example 3-15 in FIG. 3-10, the percutaneous absorption promoting effect in the case of using the lipopeptide and/or pharmaceutically acceptable salt thereof of the third present invention was determined to be unable to be obtained in the case of using a conventionally known gelling agent in the form of gellan gum (KelcoGel HM, DSP Gokyo Food & Chemical).

Example 3-14 and Comparative Example 3-17

Compositions described in the following Table 3-7 were prepared in the same manner as in the case of Example 3-1 and Comparative Example 3-1.

TABLE 3-7

|  | | Incorporated Amount (%) | |
| --- | --- | --- | --- |
| — | Component | Ex. 3-14 | Comp. Ex. 3-17 |
| (A) Lipopeptide | Pal-GH | 0.5 | — |
| (B) Polyvalent alcohol and/or glycol ether | 1,3-butylene glycol | 68.5 | 69.0 |
| | Ethoxydiglycol | 10.0 | 10.0 |
| (C) Active ingredient | Minoxidil | 1.0 | 1.0 |
| Other | Purified water | 20.0 | 20.0 |
| | Total | 100.0 | 100.0 |

<Percutaneous Absorption Test of Minoxidil>

Percutaneous absorption of minoxidil (Tokyo Chemical Industry) (amount at 8 hours after initiating stirring of the Franz cell) was determined for external use compositions obtained in the same manner as the case of Example 3-1 and Comparative Example 3-1. Detection of minoxidil by HPLC was carried out at a wavelength of 230 nm using an ultraviolet absorptiometer followed by calculating content from a calibration curve.

The results are shown in FIG. 3-11. According to FIG. 3-11, the combination of a prescribed amount of lipopeptide and/or pharmaceutically acceptable salt thereof and a polyvalent alcohol and/or glycol ether was determined to statistically significantly increase the percutaneously absorbed amount of minoxidil.

Formulation Examples

The following indicates formulation examples of the external use composition of the third present invention.

TABLE 3-8

| Whitening Essence 1 | |
| --- | --- |
| | (%) |
| L-ascorbic acid | 20 |
| Diethylene glycol monoethyl ether | 30 |
| Propylene glycol | 20 |
| Glycerin | 4 |
| Lactic acid | 1.5 |
| Iris root extract | 0.01 |

TABLE 3-8-continued

Whitening Essence 1

| | (%) |
|---|---|
| Grapefruit extract | 0.5 |
| Glasswort extract | 0.5 |
| Fragrance | 0.1 |
| Pal-GH | 0.5 |
| Purified water | Balance |
| Total | 100 |

TABLE 3-9

Spray Cosmetic

| | (%) |
|---|---|
| L-ascorbic acid | 8 |
| Ethylene glycol monoethyl ether | 50 |
| Ethanol | 10 |
| Aloe extract | 0.1 |
| Pal-GH | 1 |
| Purified water | Balance |
| Total | 100 |

TABLE 3-10

Whitening Milky Lotion

| | (%) |
|---|---|
| L-ascorbic acid | 20 |
| Polyglyceryl stearate | 1 |
| Ethylene glycol monoethyl ether | 40 |
| Sodium lactate | 0.1 |
| Stearyl alcohol | 1 |
| Squalane | 1 |
| Lavender oil | 0.5 |
| Chamomile extract | 0.5 |
| Sakhalin kelp extract | 0.5 |
| Pal-GH | 0.5 |
| Purified water | Balance |
| Total | 100 |

TABLE 3-11

External Skin Preparation

| | (%) |
|---|---|
| L-ascorbic acid | 5 |
| Dipropylene glycol monopropyl ether | 40 |
| Polyoxyethylene sorbitan fatty acid ester | 1 |
| Jojoba oil | 5 |
| Witch hazel extract | 0.1 |
| Carboxyvinyl polymer | 0.5 |
| Triethanolamine | 0.3 |
| Pal-GH | 1 |
| Purified water | Balance |
| Total | 100 |

TABLE 3-12

Whitening Cream

| | (%) |
|---|---|
| L-ascorbic acid | 20 |
| Ethylene glycol monoethyl ether | 30 |
| Sorbitan stearate | 0.7 |
| PEG sorbitan stearate | 1 |
| Paraffin | 5 |
| Cetanol | 2 |
| Glycerin | 3 |
| 1,3-butylene glycol | 5 |
| Allantoin | 0.1 |
| Xanthan gum | 0.1 |
| Pal-GH | 0.5 |
| Purified water | Balance |
| Total | 100 |

TABLE 3-13

Sunscreen

| | (%) |
|---|---|
| Arbutin | 3 |
| Trimethylglycine | 1 |
| 2-ethylhexyl para-methoxycinnamate | 10 |
| Decamethylcyclopentasiloxane | 20 |
| Octyl palmitate | 10 |
| Polyoxyethylene-methylpolysiloxane copolymer | 3 |
| Methyl hydrogenpolysiloxane-treated low temperature-fired zinc oxide | 15 |
| Alkyl polyacrylate | 5 |
| Concentrated glycerin | 5 |
| Absolute ethanol | 5 |
| 1,3-butylene glycol | 3 |
| Panthenol | 0.1 |
| Fragrance | 0.1 |
| Phytic acid | 0.05 |
| Pal-GH | 0.5 |
| Purified water | Balance |
| Total | 100 |

TABLE 3-14

Whitening Cream

| | (%) |
|---|---|
| Arbutin | 3 |
| Trimethylglycine | 2 |
| Lauryl dimethicone polyglycerin-3 crosspolymer-glyceryl tri(2-ethylhexanoate) | 5 |
| Crosslinked methylpolysiloxane-methylpolysiloxane | 5 |
| Crosslinked alkyl-modified silicon-glyceryl tri(2-ethylhexanoate) | 3 |
| Decamethylcyclopentasiloxane | 15 |
| Polymethylsilsesquioxane | 3 |
| (Dimethicone-vinyl dimethicone-methicone) crosspolymer | 1 |
| Alkyl polyacrylate | 5 |
| Concentrated glycerin | 10 |
| Magnesium sulfate | 0.1 |
| Sodium edetate | 0.05 |
| Cyanocobalamin | 0.01 |
| Methyl paraoxybenzoate 0.05 | 0.2 |
| Pal-GH | 0.5 |
| Purified water | Balance |
| Total | 100 |

TABLE 3-15

Whitening Milky Lotion

| | (%) |
|---|---|
| Arbutin | 3 |
| Trimethylglycine | 2 |
| Polyglyceryl-10 isostearate | 2 |
| Polyoxyethylene hydrogenated castor oil (HCO-10) | 0.5 |
| Squalane | 5 |
| Carboxyvinyl polymer | 0.2 |
| Triethanolamine | 0.1 |
| Concentrated glycerin | 5 |
| Magnesium sulfate | 0.1 |
| Sodium edetate | 0.05 |
| Methyl paraoxybenzoate | 0.2 |
| Pal-GH | 0.5 |
| Purified water | Balance |
| Total | 100 |

TABLE 3-16

Whitening Essence

| | (%) |
|---|---|
| Hydroquinone | 1 |
| Diethylene glycol monoethyl ether | 30 |
| Hyaluronic acid | 0.05 |
| 1,3-butylene glycol | 50 |
| Methyl paraoxybenzoate | 0.05 |
| Pal-GH | 0.5 |
| Purified water | Balance |
| Total | 100 |

TABLE 3-17

Aging Care Cream

| | (%) |
|---|---|
| Astaxanthin | 0.1 |
| Trimethylglycine | 0.1 |
| Pentaerythritol tetra(2-ethylhexanoate) | 5 |
| White Vaseline | 2 |
| Polyoxyethylene sorbitan stearate | 2 |
| Carboxyvinyl polymer | 0.1 |
| 1,3-butylene glycol | 5 |
| Cetanol | 0.5 |
| Concentrated glycerin | 5 |
| Cyanocobalamin | 0.01 |
| L-arginine | 0.1 |
| Xanthan gum | 0.1 |
| Hydroxyethyl cellulose | 0.1 |
| Sodium alginate | 0.1 |
| Methyl paraoxybenzoate | 0.2 |
| Propyl paraoxybenzoate | 0.05 |
| Pal-GH | 1 |
| Purified water | Balance |
| Total | 100 |

TABLE 3-18

Aging Care Essence

| | (%) |
|---|---|
| Astaxanthin | 0.5 |
| Trimethylglycine | 3 |
| Sodium ascorbate | 10 |
| Hyaluronic acid | 0.05 |
| 1,3-butylene glycol | 5 |
| Polyoxyethylene hydrogenated castor oil 80 | 1 |
| Methyl paraoxybenzoate | 0.05 |
| Pal-GH | 0.5 |
| Purified water | Balance |
| Total | 100 |

TABLE 3-19

Whitening Essence

| | (%) |
|---|---|
| 3-O-ethyl ascorbic acid | 3 |
| Diethylene glycol monoethyl ether | 30 |
| Propylene glycol | 20 |
| Glycerin | 4 |
| Lactic acid | 1.5 |
| Iris root extract | 0.01 |
| Grapefruit extract | 0.5 |
| Glasswort extract | 0.5 |
| Brown algae extract | 0.1 |
| Pal-GH | 0.5 |
| Purified water | Balance |
| Total | 100 |

TABLE 3-20

Topical Hair Tonic

| | Topical Hair Tonic 1 | Topical Hair Tonic 2 | Topical Hair Tonic 3 | Topical Hair Tonic 4 |
|---|---|---|---|---|
| Minoxidil | 0.5 | 1 | 0.1 | — |
| Resorcin | 1 | — | — | — |
| Pantothenyl ethyl ether | 0.1 | — | 0.5 | 0.2 |
| Hinokitiol | — | 0.05 | — | — |
| L-menthol | 0.01 | 0.1 | 1 | — |
| DL-camphor | — | — | — | 0.01 |
| *Swertia japonica* extract | 0.1 | 1 | 2 | — |
| Carrot extract | — | 0.1 | 2 | 1 |
| Tocopherol acetate | — | 0.5 | — | — |
| Dipotassium glycyrrhizate | 0.05 | — | 0.1 | 2 |
| Ethanol | 40 | 30 | 10 | — |
| Propylene glycol | 10 | — | 5 | — |
| Dipropylene glycol | — | 10 | 5 | 2 |
| Diethylene glycol monoethyl ether | — | 10 | 20 | 30 |
| Xanthan gum | — | 0.1 | — | — |
| Polyoxyethylene hydrogenated castor oil 60 | 1 | — | — | — |
| Pal-GH | 0.5 | 0.5 | 1 | 5 |
| Purified water | Balance | Balance | Balance | Balance |
| Total | 100 | 100 | 100 | 100 |

TABLE 3-21

External antibacterial preparation

| | External antibacterial preparation 1 | External antibacterial preparation 2 | External antibacterial preparation 3 | External antibacterial preparation 4 |
|---|---|---|---|---|
| Terbinafine hydrochloride | 1 | 0.1 | 1 | 1 |
| Diphenhydramine hydrochloride | 2 | 1 | 0.5 | 0.2 |

TABLE 3-21-continued

External antibacterial preparation

| | External antibacterial preparation 1 | External antibacterial preparation 2 | External antibacterial preparation 3 | External antibacterial preparation 4 |
|---|---|---|---|---|
| Dibucaine hydrochloride | 0.4 | 0.5 | 0.1 | 0.5 |
| Butenafin hydrochloride | — | — | 1 | 0.2 |
| Glycyrrhetic acid | 0.02 | 0.1 | — | — |
| Chlorobutanol | — | — | 0.1 | — |
| Crotamine | 0.1 | — | — | — |
| Isopropyl methylphenol | 0.01 | — | 0.1 | — |
| L-menthol | 0.2 | — | 1 | — |
| DL-camphor | — | 1 | — | 0.1 |
| Propylene glycol | 5 | 10 | — | 10 |
| Ethanol | 10 | 5 | 10 | 30 |
| Dipropylene glycol | 10 | 10 | — | — |
| Diethylene glycol monoethyl ether | — | 10 | 5 | — |
| Polyoxyethylene hydrogenated castor oil 60 | 1 | — | — | — |
| Pal-GH | 0.5 | 0.5 | 1 | 5 |
| Pure water | Balance | Balance | Balance | Balance |
| Total | 100 | 100 | 100 | 100 |

This completes the explanation of the third present invention. Continuing, an explanation of the fourth present invention is provided.

The Fourth Present Invention

The fourth present invention relates to an external use skin composition, a cosmetic, and a method for inhibiting discoloration of an external use skin composition.

BACKGROUND ART

In addition to the basic effects of cosmetics and the like such as cleansing, increasing beauty and appeal, changing appearance or maintaining the skin or hair in a healthy state, incorporating various active ingredients in various types of cosmetics and other compositions for external use on the skin also makes it possible to impart various types of functionality to those compositions.

Among the various types of active ingredients, antioxidants, as represented by vitamin C (ascorbic acid), are components that are able to extend the expiration date of a composition due to the antioxidative action thereof, and since antioxidants demonstrate useful actions on the skin such as by removing active oxygen generated by ultraviolet rays, they have conventionally been incorporated in a wide range of cosmetics. In addition, there are also antioxidants that have useful actions other than an antioxidative action, such as the collagen production promoting action of vitamin C.

However, there are some antioxidants that end up becoming discolored over time. For example, vitamin C ends up becoming discolored as a result of being decomposed by heat or light. This discoloration is particularly a problem in cases in which a large amount thereof is incorporated in order to enhance its effect as an antioxidant.

When the aforementioned ascorbic acid is dissolved in a raw material other than glycerin, the ascorbic acid become unstable, and since the dissolved amount thereof cannot be increased, the ascorbic acid may precipitate in the cosmetic (see Patent Document 4-1).

The problems of discoloration and precipitation as described above are critical problems for products in the manner of cosmetics for which the emphasis is placed on appearance.

With respect to the stability of the aforementioned vitamin C, Patent Document 4-2 describes that vitamin C can be stably solubilized by incorporating a low molecular weight betaine and a glycol ether such as ethoxydiglycol. However, solubilization and discoloration are completely different issues.

Furthermore, Patent Document 4-3 discloses a cosmetic that comprises a low molecular weight lipopeptide represented by the formula indicated below.

[Chemical 20]

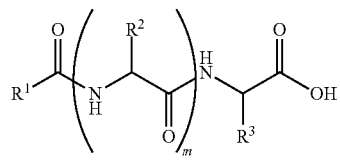

In an example of this document, a cosmetic is prepared that incorporates ascorbic acid 2-glucoside, glycerin and palmitoyl glycyl histidine (free form). However, ascorbic acid 2-glucoside is a different substance from an antioxidant that undergoes discoloration over time, and what is more, there is nothing disclosed or suggested in this document regarding the use of the aforementioned low molecular weight lipopeptide to prevent discoloration attributable to an antioxidant such as vitamin C that becomes discolored over time.

PRIOR ART DOCUMENTS

Patent Documents

[Patent Document 4-1] Japanese Unexamined Patent Publication No. 2006-111554
[Patent Document 4-2] Japanese Unexamined Patent Publication No. 2005-225865
[Patent Document 4-3] International Publication No. WO 2011/052613

DISCLOSURE OF THE FOURTH PRESENT INVENTION

Problems to be Solved by the Fourth Present Invention

As a result of conducting studies on the problem of discoloration of antioxidants, the inventors of the present invention determined that the problem of discoloration of vitamin C can be solved by incorporating a large amount of glycol ether. However, when a large amount of glycol ether is incorporated, stickiness may occur that may impair the feel during use depending on the manner of use due to the high moisturizing capacity thereof.

On the other hand, if the incorporated amount of glycol ether is decreased and the amounts of other components such as water are increased in order to ensure a favorable feel during use, the problem of the antioxidant discoloring over time is unable to be resolved.

With the foregoing in view, an object of the fourth present invention is to provide an external use skin composition in which discoloration attributable to an antioxidant that undergoes discoloration over time (to also be referred to as a "time-discolored antioxidant") is adequately inhibited.

Preferably, an object of the fourth present invention is to provide an external use skin composition in which discoloration attributable to a time-discolored antioxidant is adequately inhibited even if a large amount of that antioxidant has been incorporated.

More preferably, an object of the fourth present invention is to provide an external use skin composition in which discoloration attributable to a time-discolored antioxidant is adequately inhibited despite having reduced the incorporated amount of glycol ether.

Means for Solving the Problems of the Fourth Present Invention

As a result of conducting extensive studies to solve the aforementioned problems, the inventors of the present invention found that, by combining the use of a polyvalent alcohol and/or glycol ether with a prescribed lipopeptide and/or pharmaceutically acceptable salt thereof, discoloration attributable to a time-discolored antioxidant can be adequately inhibited, thereby leading to completion of the fourth present invention.

Namely, the gist of the fourth present invention is as indicated below.

<1> An external use skin composition comprising a lipopeptide represented by the following formula (i), and/or a pharmaceutically acceptable salt thereof, a polyvalent alcohol and/or glycol ether, and an antioxidant that undergoes discoloration over time:

[Chemical 21]

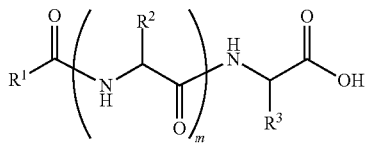

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

<2> The external use skin composition described in <1>, wherein $R^2$ in the formula (i) represents a hydrogen atom, methyl group, i-propyl group, i-butyl group or sec-butyl group.

<3> The external use skin composition described in <1> or <2>, wherein $R^1$ in the formula (i) represents an aliphatic group having 3 to 17 carbon atoms, $R^2$ represents a hydrogen atom, methyl group or i-propyl group, and $R^3$ represents a 4-aminobutyl group, 4-imidazolemethyl group or 3-methylindole group.

<4> The external use skin composition described in any of <1> to <3>, wherein the antioxidant that undergoes discoloration over time is water-soluble or oil-soluble.

<5> The external use skin composition described in any of <1> to <4>, wherein the content of the antioxidant that undergoes discoloration over time in the external use skin composition is 3% to 30% by weight.

<6> The external use skin composition described in any of <1> to <5>, wherein the content of the polyvalent alcohol and/or glycol ether in the external use skin composition is 5% to 90% by weight.

<7> The external use skin composition described in any of <1> to <6>, wherein the polyvalent alcohol and/or glycol ether is at least one type selected from the group consisting of ethoxydiglycol, dipropylene glycol, 1,3-butylene glycol, propylene glycol and glycerin.

<8> The external use skin composition described in any of <1> to <7>, wherein the antioxidant that undergoes discoloration over time is at least one type selected from the group consisting of vitamin C, hydroquinone, arbutin, astaxanthin, dibutylhydroxytoluene and coenzyme Q10.

<9> A cosmetic comprising the skin external use composition described in any of <1> to <8>.

<10> A method for inhibiting discoloration of an skin external use composition, incorporating a lipopeptide represented by the following formula (i), and/or a pharmaceutically acceptable salt thereof, and a polyvalent alcohol and/or glycol ether in an skin external use composition comprising an antioxidant that undergoes discoloration over time:

[Chemical 22]

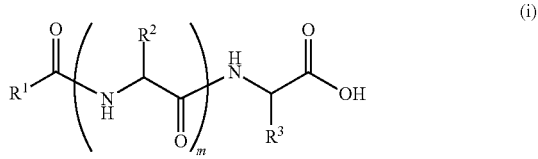

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —$(CH_2)_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

Disclosure of the Fourth Present Invention

According to the fourth present invention, an external use skin composition is provided in which discoloration attributable to a time-discolored antioxidant is adequately inhibited.

Best Mode for Carrying Out the Fourth Present Invention

The following provides a detailed explanation of the external use skin composition and cosmetic of the fourth present invention.

[Skin External Use Composition]

The external use skin composition of the fourth present invention comprises a lipopeptide represented by the aforementioned formula (i), and/or a pharmaceutically acceptable salt thereof, a polyvalent alcohol and/or glycol ether, and an antioxidant that undergoes discoloration over time. The following provides an explanation of these essential components along with other components able to be contained by the aforementioned composition.

<Lipopeptide and/or Pharmaceutically Acceptable Salt Thereof>

The lipopeptide used in the fourth present invention is a compound composed of an $R^1CO$ lipid moiety represented by the following formula (i) and a peptide moiety presented on the right side thereof.

[Chemical 23]

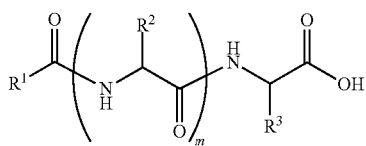

(i)

The present compound was developed as a gelling agent having high biocompatibility and safetiness and capable of providing a cosmetic and the like that demonstrates an improved feel on the skin during use, such as in terms of spreading over the skin and hair and working into to the skin and hair at the time of application, as well as not producing a sticky sensation following application, and in the case of being in the form of a liquid or sol, not dripping during application.

When the present compound was examined by the inventors of the present invention, the compound was found to have a function that inhibits discoloration attributable to a time-discolored antioxidant due to synergistic action with the polyvalent alcohol or glycol ether.

($R^1$)

In the aforementioned formula (i), $R^1$ represents an aliphatic group having 9 to 23 carbon atoms, and preferably represents an aliphatic group having 13 to 17 carbon atoms.

Examples of the lipid moiety composed of $R^1$ and a carbonyl group adjacent thereto include a decoyl group, dodecoyl group, undecoyl group, lauroyl group, dodecylcarbonyl group, myristoyl group, tetradecylcarbonyl group, palmitoyl group, margaroyl group, oleoyl group, elaidoyl group, linoleoyl group, stearoyl group, vaccenoyl group, octadecylcarbonyl group, arachidonoyl group, eicosanoyl group, behenoyl group, erucoyl group, docosylcarbonyl group, lignoceroyl group and nervonoyl group, while preferable examples include a myristoyl group, tetradecylcarbonyl group, palmitoyl group, margaroyl group, oleoyl group, elaidoyl group, linoleoyl group, stearoyl group and vaccenoyl group.

Among these, a palmitoyl group is particularly preferable for $R^1CO$ from the viewpoints of ease of production of the lipopeptide and the effect of inhibiting discoloration attributable to a time-discolored antioxidant.

($R^2$ and $R^3$)

In the aforementioned formula (i), $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or $—(CH_2)_n—X$ group and at least one of $R^2$ or $R^3$ represents a $—(CH2)_n—X$ group.

The number of carbon atoms in the alkyl group having 3 to 7 carbon atoms includes the number of carbon atoms of the branched chain optionally possessed by the alkyl group.

In addition, with respect to the aforementioned $—(CH_2)_n—X$ group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring. In the case a plurality of $R^2$ and $R^3$ represent $—(CH_2)_n—X$ groups, the plurality of n are mutually independent and the plurality of X are mutually independent.

$R^2$ preferably represents a hydrogen atom, methyl group, ethyl group or alkyl group having 3 to 7 carbon atoms that may have a branched chain having 1 to 3 carbon atoms from the viewpoint of the effect of inhibiting discoloration attributable to a time-discolored antioxidant.

Thus, $R^2$ is preferably a hydrogen atom, methyl group, ethyl group, n-propyl group, i-propyl group, n-butyl group, i-butyl group, sec-butyl group or tert-butyl group, more preferably a hydrogen atom, methyl group, i-propyl group, i-butyl group or sec-butyl group, even more preferably a hydrogen atom, methyl group or i-propyl group, and most preferably a hydrogen atom.

$R^3$ preferably represents a hydrogen atom, methyl group or $—(CH_2)_n—X$ group, n represents an integer of 1 to 4, and X represents an amino group, guanidino group, carbamoyl group, 5-membered cyclic group or 6-membered cyclic group that may have 1 to 3 nitrogen atoms or condensed cyclic group composed of a 5-membered ring and 6-membered ring from the viewpoint of the effect of inhibiting discoloration attributable to a time-discolored antioxidant.

From the same viewpoint, $R^3$ preferably represents a $—(CH_2)_n—X$ group, and X preferably represents an amino group, guanidino group, carbamoyl group, pyrrole group, imidazole group, pyrazole group or indole group. Thus, the $—(CH_2)_n—X$ group preferably represents an aminomethyl group, 2-aminoethyl group, 3-aminopropyl group, 4-aminobutyl group, carbamoylmethyl group, 2-carbamoylethyl group, 3-carbamoylpropyl group, 2-guanidinoethyl group, 3-guanidinopropyl group, pyrrolemethyl group, 4-imidazolemethyl group, pyrazolemethyl group or 3-indolemethyl group, more preferably represents a 4-aminobutyl group, carbamoylmethyl group, carbamoylethyl group, 3-carbamoylpropyl group, 4-imidazolemethyl group or 3-indolemethyl group, even more preferably represents a 4-aminobutyl group, 4-imidazolemethyl group or 3-methylindole group, and still more preferably represents a 4-imidazolemethyl group.

(m)

The number m of repetitions of units derived from an amino acid that compose the peptide structure in the aforementioned formula (i) represents an integer of 1 to 3. In the case m is 2 or more, the plurality of $R^2$ present are mutually independent. In addition, m is preferably 1 from the viewpoint of the effect of inhibiting discoloration attributable to a time-discolored antioxidant.

(Lipopeptide)

The useful compound in the fourth present invention as the previously explained lipopeptide is a compound formed from a lipid moiety and peptide moiety as indicated below. Furthermore, the abbreviation for amino acids is as follows: asparagine (Asn), alanine (Ala), glutamine (Gln), glycine (Gly), valine (Val), histidine (His), lysine (Lys) and leucine (Leu).

Myristoyl-Gly-His, myristoyl-Gly-Lys, myristoyl-Gly-Asn, myristoyl-Gly-Gln, myristoyl-Gly-Gly-His, myristoyl-Gly-Gly-Lys, myristoyl-Gly-Gly-Asn. myristoyl-Gly-Gly-Gln, myristoyl-Gly-Gly-Gly-His, myristoyl-Gly-Gly-Gly-Lys, myristoyl-Gly-Gly-Gly-Asn, myristoyl-Gly-Gly-Gly-Gln, myristoyl-Ala-His, myristoyl-Ala-Lys, myristoyl-Ala-Asn, myristoyl-Ala-Gln, myristoyl-Ala-Ala-His, myristoyl-Ala-Ala-Lys, myristoyl-Ala-Ala-Asn, myristoyl-Ala-Ala-Gln, myristoyl-Ala-Ala-Ala-His, myristoyl-Ala-Ala-Ala-Lys, myristoyl-Ala-Ala-Ala-Asn, myristoyl-Ala-Ala-Ala-Gln, myristoyl-Val-His, myristoyl-Val-Lys, myristoyl-Val-Asn, myristoyl-Val-Gln, myristoyl-Val-Val-His, myristoyl-Val-Val-Lys, myristoyl-Val-Val-Asn, myristoyl-Val-Val-Gln, myristoyl-Val-Val-Val-His, myristoyl-Val-Val-Val-Lys, myristoyl-Val-Val-Val-Asn, myristoyl-Val-Val-Val-Gln, myristoyl-Leu-His, myristoyl-Leu-Lys, myristoyl-Leu-Asn, myristoyl-Leu-Gln, myristoyl-Leu-Leu-His, myristoyl-Leu-Leu-Lys, myristoyl-Leu-Leu-Asn, myristoyl-Leu-Leu-Gln, myristoyl-Leu-Leu-Leu-His, myristoyl-Leu-Leu-Leu-Lys, myristoyl-Leu-Leu-Leu-Asn, myristoyl-Leu-Leu-Leu-Gln;

palmitoyl-Gly-His, palmitoyl-Gly-Lys, palmitoyl-Gly-Asn, palmitoyl-Gly-Gin, palmitoyl-Gly-Gly-His, palmitoyl-Gly-Gly-Lys, palmitoyl-Gly-Gly-Asn. palmitoyl-Gly-Gly-Gln, palmitoyl-Gly-Gly-Gly-His, palmitoyl-Gly-Gly-Gly-Lys, palmitoyl-Gly-Gly-Gly-Asn, palmitoyl-Gly-Gly-Gly-Gln, palmitoyl-Ala-His, palmitoyl-Ala-Lys, palmitoyl-Ala-Asn, palmitoyl-Ala-Gln, palmitoyl-Ala-Ala-His, palmitoyl-Ala-Ala-Lys, palmitoyl-Ala-Ala-Asn. palmitoyl-Ala-Ala-Gln, palmitoyl-Ala-Ala-Ala-His, palmitoyl-Ala-Ala-Ala-Lys, palmitoyl-Ala-Ala-Ala-Asn, palmitoyl-Ala-Ala-Ala-Gln, palmitoyl-Val-His, palmitoyl-Val-Lys, palmitoyl-Val-Asn, palmitoyl-Val-Gin, palmitoyl-Val-Val-His, palmitoyl-Val-Val-Lys, palmitoyl-Val-Val-Asn, palmitoyl-Val-Val-Gln, palmitoyl-Val-Val-Val-His, palmitoyl-Val-Val-Val-Lys, palmitoyl-Val-Val-Val-Asn. palmitoyl-Val-Val-Val-Gln, palmitoyl-Leu-His, palmitoyl-Leu-His, palmitoyl-Leu-Asn, palmitoyl-Leu-Gin, palmitoyl-Leu-Leu-His, palmitoyl-Leu-Leu-Lys, palmitoyl-Leu-Leu-Asn, palmitoyl-Leu-Leu-Gln, palmitoyl-Leu-Leu-Leu-His, palmitoyl-Leu-Leu-Leu-Lys, palmitoyl-Leu-Leu-Leu-Asn, palmitoyl-Leu-Leu-Leu-Gln; and, stearoyl-Gly-His, stearoyl-Gly-Lys, stearoyl-Gly-Asn, stearoyl-Gly-Gln, stearoyl-Gly-Gly-His, stearoyl-Gly-Gly-Lys, stearoyl-Gly-Gly-Asn, stearoyl-Gly-Gly-Gin, stearoyl-Gly-Gly-Gly-His, stearoyl-Gly-Gly-Gly-Lys, stearoyl-Gly-Gly-Gly-Asn, stearoyl-Gly-Gly-Gly-Gln, stearoyl-Ala-His, stearoyl-Ala-Lys, stearoyl-Ala-Asn, stearoyl-Ala-Gln, stearoyl-Ala-Ala-His, stearoyl-Ala-Ala-Lys, stearoyl-Ala-Ala-Asn, stearoyl-Ala-Ala-Gin, stearoyl-Ala-Ala-Ala-His, stearoyl-Ala-Ala-Ala-Lys, stearoyl-Ala-Ala-Ala-Asn, stearoyl-Ala-Ala-Ala-Gln, stearoyl-Val-His, stearoyl-Val-Lys, stearoyl-Val-Asn, stearoyl-Val-Gln, stearoyl-Val-Val-His, stearoyl-Val-Val-Lys, palmitoyl-Val-Val-Asn, stearoyl-Val-Val-Gln, stearoyl-Val-Val-Val-His, stearoyl-Val-Val-Val-Lys, stearoyl-Val-Val-Val-Asn, stearoyl-Val-Val-Val-Gln, stearoyl-Leu-His, stearoyl-Leu-Lys, stearoyl-Leu-Asn, stearoyl-Leu-Gln, stearoyl-Leu-Leu-His, stearoyl-Leu-Leu-Lys, stearoyl-Leu-Leu-Asn, stearoyl-Leu-Leu-Gln, stearoyl-Leu-Leu-Leu-His, stearoyl-Leu-Leu-Leu-Lys, stearoyl-Leu-Leu-Leu-Asn, stearoyl-Leu-Leu-Leu-Gln.

Among these, myristoyl-Gly-His, myristoyl-Gly-Gly-His, myristoyl-Gly-Gly-Gly-His, palmitoyl-Gly-His, palmitoyl-Gly-Gly-His, palmitoyl-Gly-Gly-Gly-His, stearoyl-Gly-His, stearoyl-Gly-Gly-His and stearoyl-Gly-Gly-Gly-His are preferable, and among these, palmitoyl-Gly-His is most preferable.

(Pharmaceutically Acceptable Salt of Lipopeptide)

Although the external use skin composition of the fourth present invention comprises a lipopeptide and/or pharmaceutically acceptable salt thereof as previously explained, examples of these salts corresponding to the carboxyl group of the lipopeptide include alkaline metal salts and alkaline earth metal salts such as lithium salts, sodium salts, potassium salts or calcium salts, and in the case $R^3$ is a group having a nitrogen atom such as a group having an imidazole structure, examples of the corresponding salts include inorganic acid salts or organic acid salts such as hydrochlorides, acetates, sulfates, carbonates, phosphates, citrates or succinates.

(Production Method of Lipopeptide and Pharmaceutically Acceptable Salt Thereof)

The method used to produce the previously explained lipopeptide and pharmaceutically acceptable salt thereof is known, and for example, can be produced by linking amino acids in the direction from of the C-terminal to the N-terminal of the amino acids composing a lipopeptide by peptide solid-phase synthesis, reacting the N-terminal of the amino acid located on the end as viewed from the solid phase with the fatty acid serving as the lipid moiety (such as myristic acid, palmitic acid, stearic acid), and then forming into a salt as necessary.

In addition, a lipopeptide and pharmaceutically acceptable salt thereof can be produced by starting from a fatty acid, reacting this with an amino acid to link the amino acid in the direction from the N-terminal to the C-terminal using a liquid phase method, and then forming into a salt as necessary.

(Content of Lipopeptide and Pharmaceutically Acceptable Salt Thereof)

Although the skin external use composition of the fourth present invention comprises a lipopeptide and/or a pharmaceutically acceptable salt thereof as previously explained, the content thereof in the entire external use skin composition (100% by weight) is 0.0001% to 10% by weight, and from the viewpoint of the effect of inhibiting discoloration attributable to a time-discolored antioxidant, is preferably 0.001% to 8% by weight, more preferably 0.01% to 5% by weight, and most preferably 0.5% to 5% by weight. In the case the content of the lipopeptide and pharmaceutically acceptable salt thereof is 0.5% to 5% by weight in particular, the discoloration inhibitory effect is remarkable and a gelled state formed by this component is extremely favorable.

In addition, in the fourth present invention, one type of lipoprotein and/or pharmaceutically acceptable salt thereof may be used alone or two or more types may be used in combination.

<Polyvalent Alcohols and/or Glycol Ethers>

The external use skin composition of the fourth present invention comprises a polyvalent alcohols and/or glycol ethers, and components known in the prior art corresponding thereto can be used in the fourth present invention without any particular limitations.

As a result of conducting extensive studies to achieve the object of the fourth present invention, the inventors of the present invention found that, in addition to glycol ethers, a polyvalent alcohol is able to adequately inhibit discoloration attributable to a time-discolored antioxidant by combining with the use of the aforementioned lipopeptide and/or pharmaceutically acceptable salt thereof.

A polyvalent alcohol having 2 to 6 carbon atoms and 2 to 4 hydroxyl groups can be used for the aforementioned polyvalent alcohol. Specific examples thereof include divalent alcohols such as ethylene glycol, propylene glycol, 1,3-propanediol (trimethylene glycol), 1,2-butylene glycol, 1,3-butylene glycol, 2,3-butylene glycol, 1,4-butanediol (tetramethylene glycol), 2-butene-1,4-diol, 1,5-pentanediol (pentamethylene glycol), 1,2-pentanediol, isoprene glycol (isopentyldiol), hexylene glycol, diethylene glycol or dipropylene glycol, trivalent alcohols such as glycerin or trimethylolpropane, and tetravalent alcohols such as diglycerin, pentaerythritol or 1,2,6-hexanetriole.

Among these, 1,3-butyleneglycol, 1,2-pentanediol, dipropylene glycol, propylene glycol and glycerin are preferable, while 1,3-butylene glycol, 1,2-pentanediol, dipropylene glycol and propylene glycol are more preferable, from the viewpoint of the effect of inhibiting discoloration attributable to a time-discolored antioxidant as a result of combining with the use of a lipopeptide and/or pharmaceutically acceptable salt thereof.

Examples of the aforementioned glycol ether include diethylene glycol monomethyl ether, diethylene glycol monoethyl ether (ethoxydiglycol), diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether and dipropylene glycol monopropyl ether.

Among these, diethylene glycol monomethyl ether, diethylene glycol monoethyl ether (ethoxydiglycol), diethylene glycol monopropyl ether, diethylene glycol monobutyl ether, diethylene glycol monoisobutyl ether, diethylene glycol dimethyl ether, ethylene glycol monobutyl ether, ethylene glycol monomethyl ether, ethylene glycol monoethyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether and dipropylene glycol monopropyl ether are preferable from the viewpoint of the action of inhibiting discoloration attributable to a time-discolored antioxidant as a result of combining with the use of a lipopeptide and/or pharmaceutically acceptable salt thereof.

From the same viewpoint, diethylene glycol monomethyl ether, diethylene glycol monoethyl ether (ethoxydiglycol), diethylene glycol monopropyl ether, ethylene glycol monobutyl ether, triethylene glycol monobutyl ether, tetraethylene glycol monobutyl ether, propylene glycol monomethyl ether, propylene glycol monoethyl ether, propylene glycol monopropyl ether, dipropylene glycol monomethyl ether, dipropylene glycol monoethyl ether and dipropylene glycol monopropyl ether are more preferable, while diethylene glycol monoethyl ether (ethoxydiglycol) is even more preferable.

The polyvalent alcohol and/or glycol ether explained above is more preferably at least one type selected from the group consisting of ethoxydiglycol, 1,3-butylene glycol, propylene glycol, dipropylene glycol and glycerin, and is particularly preferably ethoxydiglycol, from the viewpoint of the effect of inhibiting discoloration attributable to a time-discolored antioxidant as a result of combining with the use of a lipopeptide and/or pharmaceutically acceptable salt thereof.

Although there are no particular limitations on the content of the previously explained polyvalent alcohol and/or glycol ether in the external use skin composition of the fourth present inventions, the content thereof in the external use skin composition (100% by weight) is normally a total of 4% by weight or more, preferably 5% by weight or more, more preferably 10% by weight or more and even more preferably 20% by weight or more. In addition, the content thereof in the entire skin external use composition (100% by weight) of the fourth present invention is normally a total of 90% by weight or less, preferably 85% by weight or less and even more preferably 80% by weight or less.

Furthermore, in the fourth present invention, as a result of combining the use of a polyvalent alcohol and/or glycol ether with a lipopeptide and/or a pharmaceutically acceptable salt thereof, discoloration attributable to a time-discolored antioxidant can be adequately inhibited even if the incorporated amount of the former is decreased.

Consequently, in the fourth present invention, the incorporated amount of glycol ethers, which has the potential to impair feel during use of the external use skin composition when incorporated in a large amount, can be reduced to a low level. More specifically, the content of glycol ether in the external use skin composition (100% by weight) of the fourth present invention can preferably be 60% by weight or less, more preferably 55% by weight or less, and even more preferably 50% by weight or less. If within these ranges, a favorable feel during use of the external use skin composition can be ensured while inhibiting discoloration attributable to a time-discolored antioxidant. Furthermore, the lower limit of glycol ethers content is the same as described above.

<Antioxidant that Discolors Over Time>

The external use skin composition of the fourth present invention comprises an antioxidant that undergoes discoloration over time (time-discolored antioxidant) and demonstrates superior antioxidative activity. Although this time-discolored antioxidant is a component that becomes discolored due to deterioration caused by heat and light, in the fourth present invention, the aforementioned discoloration is adequately inhibited due to the combined use of the previously explained prescribed lipopeptide and/or pharmaceutically acceptable salt thereof with a polyvalent alcohol and/or glycol ether.

There are no particular limitations on the time-discolored antioxidant provided it is an antioxidant that becomes discolored due to deterioration by some form of cause as described above. In addition, "discoloration" refers to a change in color and includes color fading. In addition, this type of discoloration appears as a change in color of the appearance of the entire external use skin composition, can be confirmed with the naked eye, and as indicated in the examples to be subsequently described, can also be confirmed in the form of a change in a prescribed parameter.

The time-discolored antioxidant may be water-soluble or oil-soluble. Examples of water-soluble time-discolored antioxidants include vitamin C (ascorbic acid), hydroquinone and arbutin. Examples of oil-soluble time-discolored antioxidants include astaxanthin, dibutylhydroxytoluene and coenzyme Q10. Among these, a water-soluble time-discolored antioxidant is preferable since water-soluble antioxidants have lower toxicity.

Although there are no particular limitations on the content of the time-discolored antioxidant in the skin external use composition of the fourth present invention, since the discoloration inhibitory effect resulting from the combined use of the lipopeptide and/or pharmaceutically acceptable salt thereof and the polyvalent alcohol and/or glycol ethers is extremely high, a large amount of time-discolored antioxidant can be incorporated in the fourth present invention, thereby resulting in a highly concentrated skin external use composition for which that function has been enhanced.

More specifically, although the content of time-discolored antioxidant in the skin external use composition (100% by weight) of the fourth present invention is normally 1% by weight or more, it is preferably 3% by weight or more, more preferably 5% by weight or more and even more preferably 10% by weight or more. In addition, the content of time-discolored antioxidant in the entire skin external use composition (100% by weight) of the fourth present invention in total is preferably 30% by weight or less, more preferably 25% by weight or less and even more preferably 20% by weight or less.

In addition, there are some derivatives of time-discolored antioxidants that do not become discolored over time. In the external use skin composition of the fourth present invention, the time-discolored antioxidant may be incorporated as such a derivative and may be generated from that derivative. In this case, the aforementioned derivative may release a time-discolored antioxidant and be converted thereto after the passage of a certain amount of time.

In the fourth present invention,
(1) a time-discolored antioxidant generated by that release and conversion alone, or
(2) a time-discolored antioxidant generated by that release and conversion and a separately incorporated time-discolored antioxidant in total
may be present in an amount that makes the skin external use composition discolored time-dependently to a degree that such discoloration presents a problem.

In the external use skin composition of the fourth present invention, the aforementioned discoloration is adequately inhibited due to incorporation of the previously explained lipopeptide and/or pharmaceutically acceptable salt thereof and the polyvalent alcohol and/or glycol ethers.

<Other Components>

The skin external use composition of the fourth present invention comprises the previously explained lipopeptide and/or pharmaceutically acceptable salt thereof, polyvalent alcohol and/or glycol ethers, and time-discolored antioxidant, and may also contain in addition thereto other components, such as disinfectant component, anti-inflammatory component, anti-inflammatory analgesic component, antipruritic component, vitamins, local anesthetic component, moisturizing component, whitening component, antioxidant component other than a time-discolored antioxidant, anti-aging component, keratin softening component, cell activating component, circulation promoting component, component having action that prevents and/or repairs damaged DNA, ultraviolet absorbing component, ultraviolet scattering component, cleansing component, astringent component, hair growth component, antihistamine component or antiseptic component, within a range that does not impair the effects of the fourth present invention. Furthermore, although there are examples of the other components that correspond to time-discolored antioxidants, these components demonstrate various actions as other components in addition to being time-discolored antioxidants.

Furthermore, one type of these other components may be used alone or two or more types may be used in combination, and the incorporated amounts thereof are suitably selected from ranges known among persons with ordinary skill in the art. In addition, in the fourth present invention, components corresponding to the following plurality of components, or components corresponding to bases or carriers to be subsequently described, demonstrate the actions of each type of component corresponding thereto. Furthermore, the action of all corresponding components may not be demonstrated in the case, for example, each component is not incorporated in the amount required for the component to function.

Examples of the aforementioned disinfectant component include terbinafine and salts thereof, butenafine and salts thereof, sulconazole nitrate, luliconazole, miconazole, amorphin hydrochloride, clotrimazole, ketoconazole, bifonazole, neticonazole hydrochloride, lanoconazole, liranaftate, efinaconazole, chlorhexidine, benzalkonium chloride, acrinol, ethanol, benzethonium chloride, cresol, gluconic acid and derivatives thereof, povidone iodine, potassium iodide, iodine, isopropyl methylphenol, triclocarban, triclosan, photosensitizer 101, photosensitizer 201, paraben, phenoxyethanol and alkyldiaminoglycine hydrochloride. Among these, terbinafine and salts thereof, butenafine and salts thereof, benzalkonium chloride, benzethonium chloride, gluconic acid and derivatives thereof, isopropyl methylphenol, triclocarban, triclosan, photosensitizer 101, photosensitizer 201, paraben, phenoxyethanol and alkyldiaminoglycine hydrochloride are preferable, while terbinafine and salts thereof, butenafine and salts thereof, benzalkonium chloride, gluconic acid and derivatives thereof, benzethonium chloride and isopropyl methylphenol are more preferable.

Examples of the aforementioned anti-inflammatory component include components derived from plants (such as comfrey), allantoin, calamine, glycyrrhizic acid and derivatives thereof, glycyrrhetic acid and derivatives thereof, zinc oxide, guaiazulene, pyridoxine hydrochloride and terpene oil. Among these, comfrey leaf extract, allantoin, dipotassium glycyrrhizate and stearyl glycyrrhetinate are preferable.

Examples of the aforementioned anti-inflammatory analgesic component include indomethacin, felbinac, ibuprofen, ibuprofenpiconol, bufexamac, butyl fulfenamate, bendazac, piroxicam and ketoprofen.

Examples of the aforementioned antipruritic component include crotamiton, chlorpheniramine, chlorpheniramine maleate, diphenhydramine, diphenhydramine hydrochloride, diphenhydramine salicylate, nonylic acid vanillylamide, mequitazine, thymol, eugenol, polyoxyethylene lauryl ether and perilla extract.

Examples of the aforementioned vitamins include vitamin A compounds such as retinol, retinol derivatives (such as retinol acetate or retinol palmitate), retinal, retinoic acid, methyl retinoate, ethyl retinoate, retinol retinoate, d-δ-tocopheryl retinoate, α-tocopheryl retinoate or β-tocopheryl retinoate, provitamin A compounds such as β-carotene, α-carotene, γ-carotene, δ-carotene, lycopene, zeaxanthin, cryptoxanthin or echinenone, vitamin E compounds such as α-tocopherol, β-tocopherol, dl-α-tocopherol succinate, calcium dl-α-tocopherol succinate, 6-tocopherol or tocopherol nicotinate, vitamin B2 compounds such as riboflavin, flavin mononucleotide, flavin adenine dinucleotide, riboflavin butyrate, riboflavin tetrabutyrate, riboflavin 5'-phosphate sodium or riboflavin tetranicotinate, and nicotinic acids such as methyl nicotinate, nicotinic acid or nicotinic acid amide.

Moreover, examples of the aforementioned vitamin include vitamin C compounds such as ascorbyl stearate, L-ascorbyl dipalmitate, ascorbyl tetraisopalmitate (ascorbyl tetra-2-hexyldecanoate), sodium ascorbate, dehydroascorbic acid, sodium ascorbyl phosphate, magnesium ascorbyl phosphate and ascorbyl glucoside.

Additional examples of the aforementioned vitamins include vitamin D compounds such as methyl hesperidin, ergocalciferol or cholecalciferol, vitamin K compounds such as phylloquinone or farnoquinone, vitamin B1 compounds such as dibenzoylthiamine, dibenzoylthiamine hydrochloride, thiamine hydrochloride, thiamine cetyl hydrochloride, thiamine thiocyanate, thiamine lauryl hydrochloride, thiamine nitrate, thiamine monophosphate, thiamine diphosphate, thiamine triphosphate, thiamine monophosphate ester phosphate, thiamine monophosphate ester, thiamine diphosphate ester, thiamine triphosphate ester hydrochloride, thiamine triphosphate ester or thiamine triphosphate ester monophosphate, vitamin B6 compounds such as pyridoxine hydrochloride, pyridoxine acetate, pyridoxal hydrochloride, pyridoxal 5'-phosphate or pyridoxamine hydrochloride, vitamin B12 compounds such as cyanocobalamin, hydroxocobalamin or deoxyadenosylcobalamin, folic acid compounds such as folic acid or pteroylglutamic acid, pantothenates such as pantothenic acid, calcium pantothenate, pantothenyl alcohol (panthenol), D-pantetheine, D-pantethine, coenzyme A or pantothenyl ethyl ether, biotins such as biotin or biocytin, and vitamin-like agents such as carnitine, ferulic acid, α-lipoic acid, orotic acid or γ-oryzanol.

Among the vitamins listed above, vitamin C compounds such as sodium ascorbyl phosphate, magnesium ascorbyl phosphate or ascorbyl tetraisopalmitate (ascorbyl tetra-2-hexyldecanoate) are preferable.

Examples of the aforementioned local anesthetic component include lidocaine, lidocaine hydrochloride, dibucaine, dibucaine hydrochloride, ethyl aminobenzoate, eucalyptus oil, eugenol and chlorobutanol.

Examples of the aforementioned moisturizing component include components derived from plants (such as lavender, glasswort or cogon), amino acids and derivatives thereof such as alanine, serine, leucine, isoleucine, threonine, glycine, proline, hydroxyproline, glucosamine or theanine, proteins, peptides and hydrogenated forms thereof such as collagen, gelatin or elastin, sugar-alcohols such as sorbitol, phospholipids such as lecithin or hydrogenated lecithin, mucopolysaccharides such as hyaluronic acid, sodium hyaluronate, acetylhyaluronic acid, sodium acetylhyaluronate, heparin or chondroitin, NMF-derived components such as lactic acid, sodium pyrrolidone carboxylate or urea, polyglutamic acid, polymers having a phospholipid polar group such as MPC polymers (such as Lipidure®), polyoxypropylene methyl glucoside, trimethylglycine (betaine), hydroxyethyl urea, acrylic acid-acrylamide-dimethylallyl ammonium chloride copolymers and sorbitol.

Among these, lavender oil, glasswort extract, cogon grass extract, hydrolyzed collagen, hydrolyzed elastin, MPC polymers, trimethylglycine (betaine), hydroxyethyl urea, acrylic acid-acrylamide-dimethylallyl ammonium chloride copolymers, hydrogenated lecithin, hyaluronic acid, sodium hyaluronate, acetylhyaluronic acid, sodium acetylhyaluronate and sorbitol are preferable.

Examples of the aforementioned whitening component include arbutin, hydroquinone, kojic acid, ellagic acid, phytic acid, 4-n-butylresorcinol, chamomile extract, ascorbic acid or derivatives thereof (such as alkyl ethers of ascorbic acid), vitamin E or derivatives thereof, pantothenic acid or derivatives thereof, tranexamic acid and plant components having whitening action (including plant extracts such as grapefruit extract, witch hazel extract, iris root extract or aloe extract, components derived from marine plants such as brown algae extract or Sakhalin kelp extract, and refined oils). Among these, arbutin, hydroquinone, kojic acid and tranexamic acid are preferable.

Examples of the aforementioned antioxidant component other than a time-discolored antioxidant include components derived from plants (such as grape, Asian ginseng or comfrey), proanthocyanidin, tocopherol and derivatives thereof, ascorbic acid derivatives, hesperidin, glucosyl hesperidin, ergothioneine, sodium hydrogen sulfite, erythorbic acid and salts thereof, flavonoids, glutathione, glutathione peroxidase, glutathione-S-transferase, catalase, superoxide dismutase, thioredoxin, taurine, thiotaurine and hypotaurine.

Among these, grape seed extract, grape leaf extract, Asian ginseng extract, comfrey leaf extract, proanthocyanidin, tocopherol and derivatives thereof (and particularly δ-tocopherol and α-tocopherol), ascorbic acid derivatives (and particularly sodium ascorbyl phosphate, magnesium ascorbyl phosphate and ascorbyl tetraisopalmitate (ascorbyl tetra-2-hexyldecanoate)), hesperidin, glucosyl hesperidin and ergothioneine are preferable.

Examples of the aforementioned anti-aging component include hydrolyzed soybean protein, retinoids (such as retinol and derivatives thereof, retinoic acid or retinal), pangamic acid, kinetin, ursolic acid, turmeric extract, sphingosine derivatives, silicon, silicic acid, N-methyl-L-serine and mevalonolactone. Among these, artemia extract, hydrolyzed soybean protein, retinol, retinol acetate and retinol palmitate are preferable.

Examples of the aforementioned keratin softening component include lanolin, urea, phytic acid, lactic acid, lactate, glycolic acid, salicylic acid, malic acid and citric acid.

Among these, lactic acid, sodium lactate, glycolic acid and phytic acid are preferable.

Examples of the aforementioned cell activating component include components derived from plants (such as bilberry), amino acids such as γ-aminobutyric acid or ε-aminocaproic acid, vitamins such as retinol and derivatives thereof, thiamine, riboflavin, pyridoxine hydrochloride or pantothenates, α-hydroxy acids such as glycolic acid or lactic acid, tannin, flavonoids, saponin, allantoin and photosensitizer 301. Among these, bilberry leaf extract, retinol, retinol acetate and retinol palmitate are preferable.

Examples of the aforementioned circulation promoting component include components derived from vegetable oils (such as Asian ginseng, Angelica keiskei, mountain arnica, gingko, fennel, Isodonis japonicus, Dutch oak, chamomile, Roman chamomile, Daucus carota sativa, gentian, burdock, rice, Japanese hawthorn, shiitake mushroom, English hawthorn, juniper, cnidium, thyme, clove, citrus unshiu, angelica root, peach kernel, spruce, carrot, garlic, butcher's broom, grape, peony, horse chestnut, lemon balm, yuzu, coix, rosemary, rose hip, citrus unshiu, angelica, spruce, peach, apricot, walnut or corn), tocopherol nicotinate, glucosyl hesperidin and hesperidin.

Among these, Asian ginseng extract, tocopherol nicotinate, glucosyl hesperidin and hesperidin are preferable.

Examples of the aforementioned component having action that prevents and/or repairs damaged DNA include components derived from animals (such as artemia), components derived from plants (such as cat's claw), and nucleic acid components such as DNA, DNA salts, RNA and RNA salts. Among these, artemia extract and DNA-Na are preferable.

Examples of the aforementioned ultraviolet absorbing component include 2-ethylhexyl para-methoxycinnamate, hexylethyl 2-[4-(diethylamino)-2-hydroxybenzoyl]benzoate, 2,4,6-tris[4-(2-ethylhexyloxycarbonyl)anilino]-1,3,5-triazine, 2-ethylhexyl dimethoxybenzylidene oxoimidazolidine propionate and 2,4-bis[{4-(2-ethylhexyloxy)-2-hydroxy}-phenyl]-6-(4-methoxyphenyl)-1,3,5-triazine.

Among these, 2-ethylhexyl para-methoxycinnamate, hexylethyl 2-[4-(diethylamino)-2-hydroxybenzoyl]benzoate and 2,4,6-tris[4-(2-ethylhexyloxycarbonyl)anilino]-1,3,5-triazine are preferable.

Examples of the aforementioned ultraviolet scattering component include inorganic compounds such as zinc oxide, titanium oxide, iron oxide, cerium oxide, zirconium oxide, titanium silicate, zinc silicate, silicic anhydride, cerium silicate or hydrated silicic acid, ultraviolet scattering components obtained by coating these inorganic compounds with an inorganic powder such as hydrated silicic acid, aluminum hydroxide, mica or talc, ultraviolet scattering components obtained by compounding into a resin powder such as polyamide, polyethylene, polyester, polystyrene or nylon, and ultraviolet scattering components obtained by treating these inorganic compounds with silicone oil or fatty acid aluminum salts. Among these, inorganic compounds such as zinc oxide, titanium oxide or iron oxide, and these inorganic compounds coated with an inorganic powder, such as aluminum hydroxide, hydrated silicic acid, mica or talc, or silicone oil are preferable.

Examples of the aforementioned cleansing component include anionic surfactants in the manner of polyoxyalkylene alkyl (or alkenyl) ether sulfates, alkyl (or alkenyl) sulfates, higher fatty acid salts, ether carboxylates, amide ether carboxylates, alkyl phosphate esters salts, N-acylamino acid salts, polyoxyalkylene fatty acid amide ether sulfates, acylated isethionates or acylated taurates, nonionic surfactants such as amine oxides, glycerin fatty acid esters, sorbitan fatty acid esters, alkyl saccharides, polyoxyalkylene alkyl ethers, fatty acid alkanol amides or polyoxyalkylene hydrogenated castor oil, cationic surfactants such as mono- or di-long chain alkyl quaternary ammonium salts having a linear or branched long chain alkyl group to which alkylene oxide may or may not be added, and amphoteric surfactants such as carbobetaine, sulfobetaine, imidazolinium betaine or betaine amide.

Among these, anionic surfactants, nonionic surfactants and amphoteric surfactants are preferable. Among anionic surfactants, higher fatty acid salts (and particularly salts of higher fatty acids such as palmitic acid, lauric acid, myristic acid or stearic acid) and N-acylamino acid salts (and particularly sodium N-lauroyl aspartate, potassium hydroxide-potassium N-cocoylacyl glutamate, sodium cocoylacyl glycine or myristyl glutamic acid) are preferable. Among nonionic surfactants, fatty acid alkanol amides (and particularly cocoyl diethhanolamide or cocoyl monoethanolamide) and amine oxides (and particularly cocoyl alkyldimethylamine oxides or lauryl dimethylamine oxides) are preferable. Among amphoteric surfactants, imidazolinium betaines (and particularly 2-alkyl-N-carboxymethyl-N-hydroxyethyl imidazolinium betaine or disodium N-cocoylacyl-N-carboxymethoxyethyl-N-carboxymethyl-ethoxydiamine) are preferable.

Examples of the aforementioned astringent component include metal salts such as alum, aluminum chlorohydrate, aluminum chloride, allantoin aluminum salt, zinc sulfate or potassium aluminum sulfate, and organic acids such as tannic acid, citric acid, lactic acid or succinic acid.

Among these, alum, aluminum chlorohydrate, aluminum chloride, allantoin aluminum salt, potassium aluminum sulfate and tannic acid are preferable.

Examples of the aforementioned hair growth component include procyanidin, dipotassium glycyrrhizate, carpronium chloride, cephalothin, menthol, hinokitiol, L-hydroxyproline, acetyl hydroxyproline, fucoidan, capsicum tincture, cephalothin, sueruchianin, panax ginseng, flavonosteroid, minoxidil, FGF-10, Isodonis japonicus extract, Swertia herb extract, ribbon weed extract, five-leaf ginseng extract, St. John's wort extract, gentian extract, sage extract, peppermint extract, hop extract, coix extract, persimmon leaf extract, rehmannia root extract, carrot extract, Bohdi tree extract, moutan bark extract and tree bark extract.

Examples of the aforementioned antihistamine component include ethanolamine-based compounds such as diphenhydramine, diphenhydramine hydrochloride or dimenhydrinate, propylamine-based compounds such as chlorpheniramine maleate, phenothiazine-based compounds such as promethazine hydrochloride, piperazine-based compounds such as hydroxyzine, piperidine-based compounds such as cyproheptadine hydrochloride, epinastine hydrochloride, loratadine and fexofenadine hydrochloride. In addition, pharmaceutically acceptable salts of each compound can also be used in addition to hydrochloride forms thereof. Among these, diphenhydramine, diphenhydramine hydrochloride and chlorpheniramine maleate are preferable.

Examples of the aforementioned antiseptic component include benzoic acid, sodium benzoate, dehydroacetic acid, sodium dehydroacetate, isobutyl paraoxybenzoate, isopropyl paraoxybenzoate, butyl paraoxybenzoate, ethyl paraoxybenzoate, propyl paraoxybenzoate, benzyl paraoxybenzoate, methyl paraoxybenzoate and phenoxyethanol. Among these, methyl paraoxybenzoate, propyl paraoxybenzoate and phenoxyethanol are preferable.

<Property>

The skin external use composition of the fourth present invention comprises the previously explained lipopeptide and/or pharmaceutically acceptable salt thereof, polyvalent alcohol and/or glycol ether, time-discolored antioxidant, other components as previously described as necessary, and a base, carrier or additives to be subsequently described.

The aforementioned lipopeptide and/or pharmaceutically acceptable salt thereof is a superior gelling agent, and a prescribed viscosity can be imparted to the skin external use composition of the fourth present invention by the incorporation thereof. As a result, dripping of applied composition can be prevented and the feel during use of the composition can be enhanced.

Embodiments of Formulation of Skin External Use Composition

The external use skin composition of the fourth present invention can be an external use skin composition in the form of a pharmaceutical, quasi drug or cosmetic by mixing essential components thereof and other components as previously explained in accordance with ordinary methods together with a base, carrier and, as necessary, an additive to be subsequently described, that are normally used in pharmaceuticals, quasi drugs or cosmetics.

Examples of the aforementioned base or carrier include hydrocarbons such as liquid paraffin, squalane, Vaseline, gelling hydrocarbons (such as plastibase), ozokerite, α-olefin oligomers or light liquid paraffin, silicone oils such as methylpolysiloxane, highly polymerized methylpolysiloxane, cyclic silicone, alkyl-modified silicone, amino-modified silicone, polyether-modified silicone, polyglycerin-modified silicone, silicone-alkyl chain co-modified polyether-modified silicone, silicone-alkyl chain co-modified polyglycerin-modified silicone, polyether-modified branched silicone, polyglycerin-modified branched silicone, acrylsilicone, phenyl-modified silicone or silicone resin, oils such as palm oil, olive oil, rice bran oil or shea butter, waxes such as jojoba oil, beeswax, candelilla wax or lanolin, higher alcohols such as cetanol, cetostearyl alcohol, stearyl alcohol, behenyl alcohol, octyl dodecanol, isostearyl alcohol, phytosterol or cholesterol, cellulose derivatives such as ethyl cellulose, hydroxypropyl cellulose or hydroxypropyl methyl cellulose, polyvinylpyrrolidone, carrageenan, polyvinylbutyrate, polyethylene glycol, dioxane, butylene glycol polyester adipate, esters such as diisopropyl adipate, isopropyl myristate, octyldodecyl myristate, isopropyl palmitate, cetyl palmitate, isononyl isononanoate or pentaerythritol tetra(2-ethylhexanoate), polysaccharides such as dextrin or maltodextrin, vinyl-based polymers such as carboxyvinyl polymer or alkyl-modified carboxyvinyl polymer, lower alcohols such as ethanol or isopropanol, and water.

In the case the external use skin composition of the fourth present invention comprises a polyvalent alcohol, the polyvalent alcohol may also fulfill the role of a base or carrier.

In the case the external use skin composition of the fourth present invention comprises a base or carrier other than water, the base or carrier is preferably a higher alcohol, hydrocarbon, oil, ester, silicone oil or waxes, and more preferably a higher alcohol, ester or silicone oil. Among these components, cetanol, cetostearyl alcohol, stearyl alcohol, behenyl alcohol, glyceryl tri-2-ethylhexanoate, dimethicone, cyclomethicone, polyether-modified silicone and polyglycerin-modified silicone are more preferable.

In the case the external use skin composition of the fourth present invention comprises water, the content thereof in the skin external use composition (100% by weight) of the fourth present invention is preferably 3% by weight or more, more preferably 5% by weight or more and more preferably 10% by weight or more. In addition, the content of water in the entire external use skin composition (100% by weight) of the fourth present invention in total is preferably 50% by weight or less, more preferably 40% by weight or less, and even more preferably 20% by weight or less.

One type of the previously explained base or carrier can be used alone or two more types can be used in combination, and the amounts used thereof are suitably selected from known ranges by a person with ordinary skill in the art.

<Form>

There are no particular limitations on the form of the external use composition of a pharmaceutical preparation, and examples thereof include an ointment, liquid, suspension, emulsion (milky lotion and cream), gel, liniment, lotion, aerosol, tape or poultice. These preparations can be produced in accordance with methods described in the general rules of preparations of the 16th edition of the Japanese Pharmacopoeia.

There are no particular limitations on the form of the external use composition of a quasi drug or cosmetic preparation, and examples thereof include a beauty lotion, essence, milky lotion, cream, gel, ointment, spray, hand cream, body lotion, body cream, lip cream or sunscreen. These preparations can be produced in accordance with ordinary methods.

<Additives>

Additives known to be added to a pharmaceutical, quasi drug or cosmetic, such as a surfactant, stabilizer, antioxidant other than a time-discolored antioxidant, colorant, pearling agent, dispersant, chelating agent, pH adjuster, preservative, thickener or irritation reducing agent, can be added to the external use skin composition of the fourth present invention within a range that does not impair the effects of the fourth present invention. Furthermore, although there are examples of substances among the following additives that correspond to time-discolored antioxidants, these components demonstrate various actions as additives in addition to being time-discolored antioxidants.

One type of these additives can be used alone or two or more types can be used in combination. Moreover, although the following additives corresponding to a plurality of components demonstrate the action of that plurality of components, they may not demonstrate a plurality of actions in certain cases.

Examples of the aforementioned surfactant include amines such as stearylamine or oleylamine, and silicone-based surfactants such as polyoxyethylene-methylpolysiloxane copolymer, lauryl PEG-9 polydimethylsiloxyethyl dimethicone or PEG-9 polydimethylsiloxyethyl dimethicone.

Examples of the aforementioned stabilizer include magnesium sulfate, sodium polyacrylate, dibutylhydroxytoluene and butylhydroxyanisole.

Examples of the aforementioned antioxidant other than a time-discolored antioxidant include butylhydroxyanisole, sorbic acid, sodium sulfite, erythorbic acid and L-cysteine hydrochloride.

Examples of the aforementioned colorant include inorganic pigments and natural pigments.

Examples of the aforementioned pearling agent include ethylene glycol distearate, ethylene glycol monostearate and triethylene glycol distearate.

Examples of the aforementioned dispersant include sodium pyrophosphate, sodium hexametaphosphate, polyvinyl alcohol, polyvinylpyrrolidone, methyl vinyl ether-maleic anhydride copolymer and organic acids.

Examples of the aforementioned chelating agent include EDTA-2Na, EDTA-Ca2Na, etc.

Examples of the aforementioned pH adjuster include inorganic acids (such as hydrochloric acid or sulfuric acid), organic acids (such as lactic acid, sodium lactate, citric acid, sodium citrate, succinic acid or sodium succinate), inorganic bases (such as potassium hydroxide or sodium hydroxide), and organic bases (such as triethanolamine, diisopropanolamine or triisopropanolamine).

Examples of the aforementioned preservative include benzoic acid, sodium benzoate, dehydroacetic acid, sodium dehydroacetate, isobutyl paraoxybenzoate, isopropyl paraoxybenzoate, butyl paraoxybenzoate, ethyl paraoxybenzoate, propyl paraoxybenzoate, benzyl paraoxybenzoate, methyl paraoxybenzoate and phenoxyethanol.

Examples of the aforementioned thickener include cellulose-based thickeners such as methyl cellulose, ethyl cellulose, hydroxyethyl cellulose, hydroxymethyl cellulose, hydroxypropyl cellulose, hydroxypropyl methyl cellulose, carboxymethyl cellulose or carboxyethyl cellulose, gua gum, pectin, pullulan, gelatin, locust bean gum, carrageenan, agar, gellan gum, xanthan gum, polyvinyl alcohol, polyvinylpyrrolidone, carboxyvinyl polymer, acrylic acid-alkyl methacrylate copolymer, polyethylene glycol, bentonite, alginic acid, propylene glycol alginate, Macrogol, sodium chondroitin sulfate, hyaluronic acid, sodium hyaluronate, hydroxyethyl acrylate-sodium acryloyldimethyl taurate copolymer and ammonium acryloyldimethyl taurate-vinylpyrrolidone copolymer.

Examples of the aforementioned irritation reducing agent include licorice extract, gum arabic, polyvinylpyrrolidone and sodium alginate.

<Preparation Method of Skin External Use Composition>

There are no particular limitations on the method used to prepare the external use skin composition of the fourth present invention, and can be produced in accordance with ordinary methods by suitably selecting and incorporating essential components as well as other components and various types of components required to produce the external use skin composition (such as the aforementioned base, carrier or additives). Forms of the resulting skin external use composition of the fourth present invention are as previously described.

Furthermore, in the external use skin composition of the fourth present invention, discoloration attributable to a time-discolored antioxidant is inhibited by combining the use of a lipopeptide represented by the aforementioned formula (i), and/or a pharmaceutically acceptable salt thereof, and a polyvalent alcohol and/or glycol ether. For this reason, from a different viewpoint, the fourth present invention can be perceived to be a method for inhibiting discoloration of a skin external use composition that comprises the incorporation of a lipopeptide represented by the aforementioned formula (i), and/or a pharmaceutically acceptable salt thereof, and a polyvalent alcohol and/or glycol ether in a skin external use composition comprising an antioxidant that undergoes discoloration over time.

Furthermore, although a "lipopeptide represented by formula (i), and/or pharmaceutically acceptable salt thereof, and a polyvalent alcohol and/or glycol ether" are incorporated in the method for inhibiting discoloration, there are no particular limitations on the method used to incorporate this component or the time-discolored antioxidant (with respect to the order and conditions thereof). It is only required that the time-discolored antioxidant, lipopeptide and/or pharmaceutically acceptable salt thereof, and polyvalent alcohol and/or glycol ether be present together in the external use skin composition as a result of carrying out the aforementioned method for inhibiting discoloration. For example, these three components (and other components as necessary) may be incorporated (mixed) simultaneously or these components may be incorporated sequentially in any arbitrary order.

[Cosmetic]

Since the external use skin composition of the fourth present invention comprises a lipopeptide, and/or pharmaceutically acceptable salt thereof, which enhances sense of use of the composition by imparting a prescribed viscosity and inhibits discoloration attributable to a time-discolored antioxidant, then it is able to keep the appearance of the composition unchanged while also to incorporate various types of cosmetic components, it can be preferably used as a cosmetic.

In addition to those examples of preparation forms exemplified as preparation forms of the external use skin composition of the fourth present invention that apply to preparation forms of cosmetics, various types of conventionally known preparation forms used for the preparation form of a cosmetic can be used without any particular limitations for the preparation form of the cosmetic of the fourth present invention.

Examples of the Fourth Present Invention

Although the following provides a more detailed explanation of the fourth present invention through examples thereof, the fourth present invention is not limited thereby. Furthermore, the units of numerical values are in percent by weight unless specifically indicated otherwise.

Examples 4-1 to 4-3 and Comparative Examples 4-1 to 4-3

Method for Preparing Compositions of Examples 4-1 to 4-3 and Comparative Examples 4-1 to 4-3

The compositions of Examples 4-1, 4-2 and 4-3 were prepared as described in the following Table 4-1 so that 0.5% of palmitoyl-Gly-His (to be referred to as Pal-GH) was contained and the final concentration of ascorbic acid (VC) was 3%, 10% or 20%.

In addition, the compositions of Comparative Examples 4-1, 4-2 and 4-3 were prepared as described in the following Table 4-2 so that the final concentration of ascorbic acid was 3%, 10% or 20% and palmitoyl-Gly-His was not contained.

TABLE 4-1

|  | Example 4-1 | Example 4-2 | Example 4-3 |
|---|---|---|---|
| Pal-GH | 0.5 | 0.5 | 0.5 |
| Ethoxydiglycol | 20 | 20 | 20 |
| VC | 20 | 10 | 3 |
| Water | 20 | 20 | 20 |
| BG | 39.5 | 49.5 | 56.5 |
| Total | 100 | 100 | 100 |

\* BG indicates 1,3-butylene glycol, and to apply similarly hereinafter.

TABLE 4-2

|  | Comp. Ex. 4-1 | Comp. Ex. 4-2 | Comp. Ex. 4-3 |
|---|---|---|---|
| Pal-GH | — | — | — |
| Ethoxydiglycol | 20 | 20 | 20 |
| VC | 20 | 10 | 3 |
| Water | 20 | 20 | 20 |
| BG | 40 | 50 | 57 |
| Total | 100 | 100 | 100 |

20 ml aliquots of the compositions of the examples and comparative examples were filled into a glass bottle followed by determination of the initial $\Delta E^*ab(0)$ value with a color difference meter (Spectrophotometer Model CM-5, Konica Minolta). At this time, purified water was used for the reference color. $\Delta E^*ab(0)$ values are represented by the equation indicated below and used as an indicator to represent the degree of coloring of the compositions of the examples and comparative examples.

$$\Delta E^*ab=\{(\Delta L^*)^2+(\Delta a^*)^2+(\Delta b^*)^2\}^{1/2} \qquad \text{[Equation 1]}$$

The L* value ($\Delta L^*$) is a value relating to lightness, the a* value ($\Delta a^*$) is a value relating to red/green opponent colors in both directions, and the b* value ($\Delta b^*$) is a value relating to blue/yellow opponent colors in both directions. The compositions of the aforementioned examples and comparative examples were each stored (under protection from light) at 40° C., 50° C. and 60° C. and then taken out after 4 days followed by determination of the $\Delta E^*ab(4)$ value with the aforementioned color difference meter.

The rate of increase in the $\Delta E^*ab$ values attributable to being stored for 4 days at the aforementioned temperatures was determined using the equation indicated below. The term "(D65)" in the equation indicates the use of Illuminant D65.

$$\text{Rate of increase in } \Delta E^*ab(D65)=\Delta E^*ab(65)(4)/\Delta E^*ab(D65)(1)$$

The results are shown in FIGS. 4-1 to 4-3. A lower value for the rate of increase in ΔE*ab indicates a smaller degree of coloration. According to FIGS. 4-1 to 4-3, compositions of the examples comprising a prescribed lipopeptide and polyvalent alcohol and/or glycol ether were determined to stably contain vitamin C at various concentrations, including the case of a high concentration, without any discoloration in comparison with the compositions of the comparative examples not comprising lipopeptide.

Examples 4-4 and 4-5 and Comparative Examples 4-4 and 4-5

The compositions described in the following Tables 4-3 and 4-4 were prepared in the same manner as in the case of Examples 4-1 to 4-3 and Comparative Examples 4-1 to 4-3.

TABLE 4-3

| Component | Example 4-4 Incorporated Amount (%) | Example 4-5 Incorporated Amount (%) |
|---|---|---|
| Pal-GH | 0.50 | 0.50 |
| 1,3-butylene glycol | 39.50 | 39.50 |
| PG | 20.00 | 0.00 |
| Dipropylene glycol | 0.00 | 20.00 |
| Purified water | 20.00 | 20.00 |
| Ascorbic acid | 20.00 | 20.00 |
| Total | 100.00 | 100.00 |

* PG indicates propylene glycol, and to apply similarly hereinafter.

TABLE 4-4

| Component | Comp. Ex. 4-4 Incorporated Amount (%) | Comp. Ex. 4-5 Incorporated Amount (%) |
|---|---|---|
| Pal-GH | 0.00 | 0.00 |
| 1,3-butylene glycol | 40.00 | 40.00 |
| PG | 20.00 | 0.00 |
| Dipropylene glycol | 0.00 | 20.00 |
| Purified water | 20.00 | 20.00 |
| Ascorbic acid | 20.00 | 20.00 |
| Total | 100.00 | 100.00 |

The resulting compositions were stored (under protection from light) at 50° C. and 60° C. and then taken out after 4 days followed by determining the rate of increase in ΔE*ab attributable to being stored for 4 days in the same manner as in the case of Examples 4-1 to 4-3 and Comparative Examples 4-1 to 4-3.

Figures 2, 3, 4, 5:
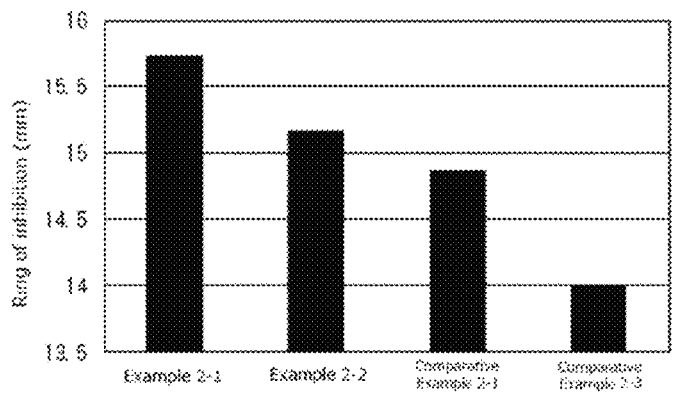

The results are shown in FIGS. 4-4 and 4-5. According to FIGS. 4-4 and 4-5, compositions of the examples comprising a prescribed lipopeptide and polyvalent alcohol and/or glycol ether were determined to stably contain a high concentration of vitamin C at 20% by weight without any discoloration in comparison with the compositions of the comparative examples not comprising lipopeptide.

Examples 4-6 to 4-9 and Comparative Examples 4-6 to 4-9

The compositions described in the following Tables 4-5 and 4-6 were prepared in the same manner as in the case of Examples 4-1 to 4-3 and Comparative Examples 4-1 to 4-3.

TABLE 4-5

| | Example 4-6 | Example 4-7 | Example 4-8 | Example 4-9 |
|---|---|---|---|---|
| Pal-GH | 0.5 | 0.5 | 0.5 | 0.5 |
| Ethoxydiglycol | 20 | 20 | 15 | 4.5 |
| Ascorbic acid | 10 | 10 | 10 | 10 |
| Water | 40 | 50 | 70 | 85 |
| BG | 29.5 | 19.5 | 4.5 | 0 |
| Total | 100 | 100 | 100 | 100 |

TABLE 4-6

| | Comp. Ex. 4-6 | Comp. Ex. 4-7 | Comp. Ex. 4-8 | Comp. Ex. 4-9 |
|---|---|---|---|---|
| Pal-GH | — | — | — | — |
| Ethoxydiglycol | 20 | 20 | 20 | 5 |
| Ascorbic acid | 10 | 10 | 10 | 10 |
| Water | 40 | 50 | 70 | 85 |
| BG | 30 | 20 | 0 | 0 |
| Total | 100 | 100 | 100 | 100 |

The resulting compositions were stored (under protection from light) at 50° C. and 60° C. and then taken out after 4 days followed by determining the rate of increase in ΔE*ab attributable to being stored for 4 days in the same manner as in the case of Examples 4-1 to 4-3 and Comparative Examples 4-1 to 4-3.

Figures 2, 3, 4, 5, 6:
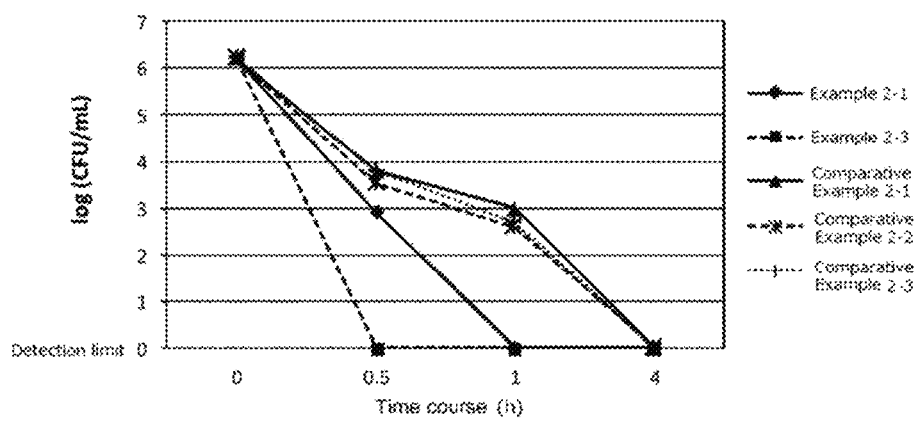
Figures 2, 3, 4, 5, 6, 7:
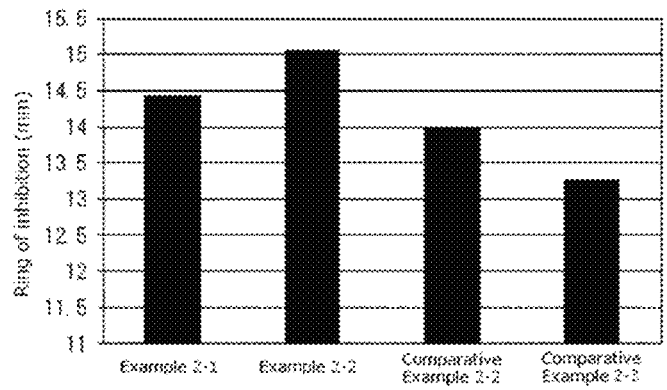
Figures 1, 3:
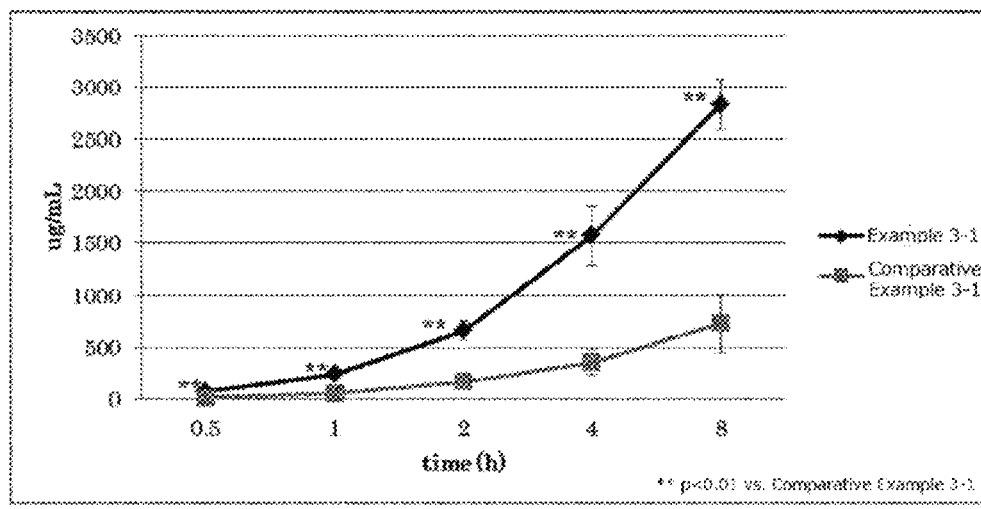
Figures 2, 3:
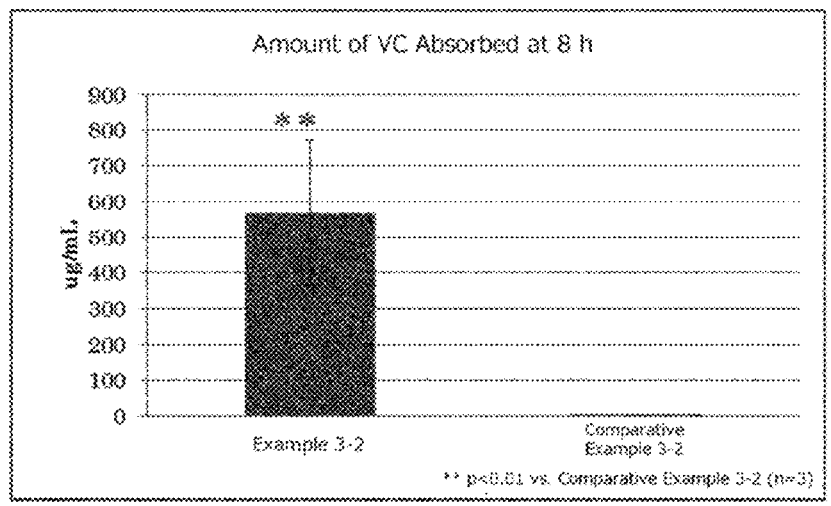
Figure 3:
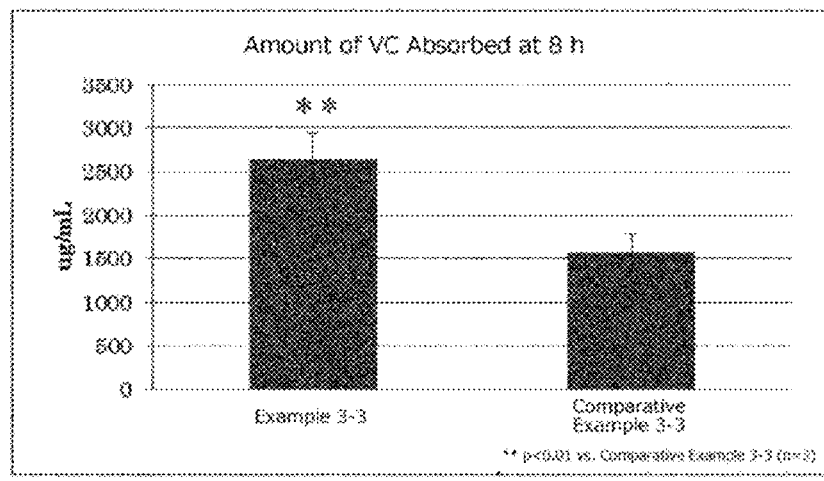
Figures 3, 4:
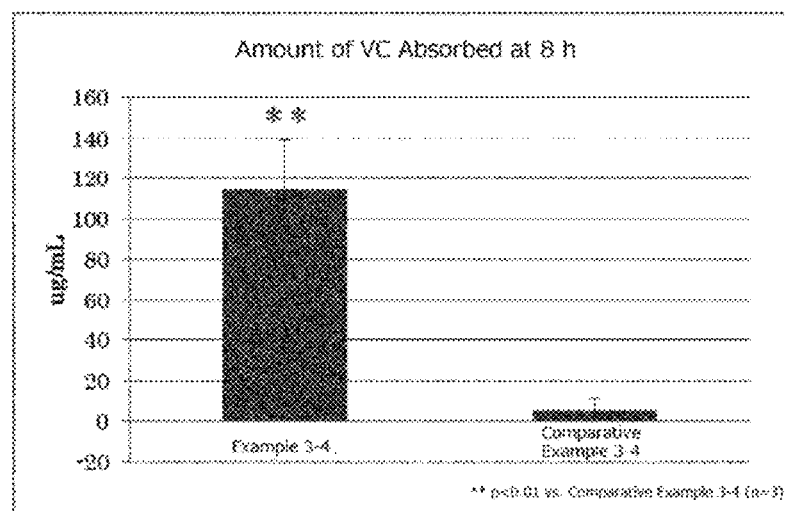
Figures 3, 4, 5:
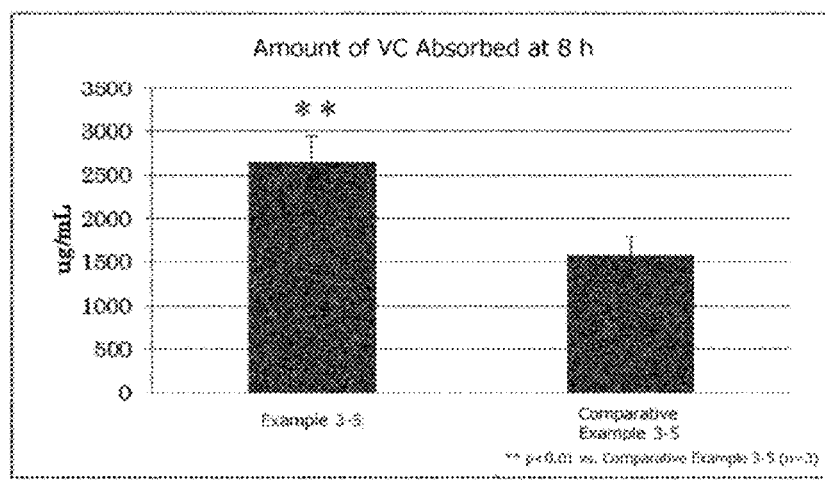
Figures 3, 4, 5, 6:
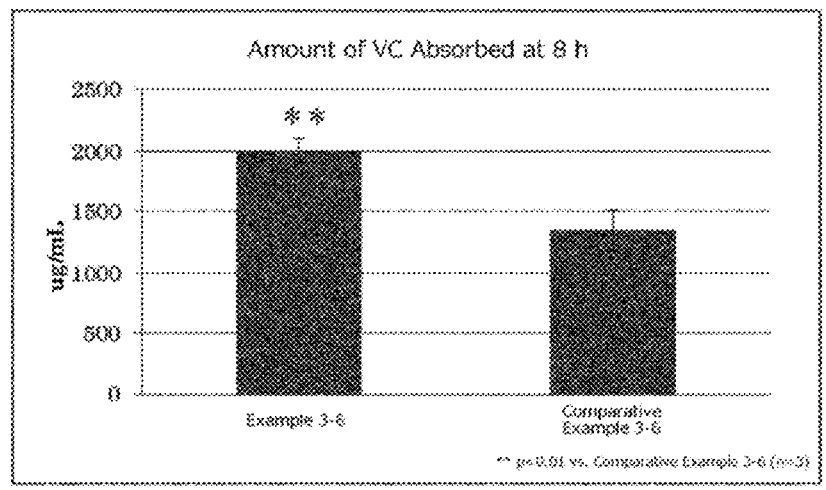
Figures 3, 4, 5, 6, 7:
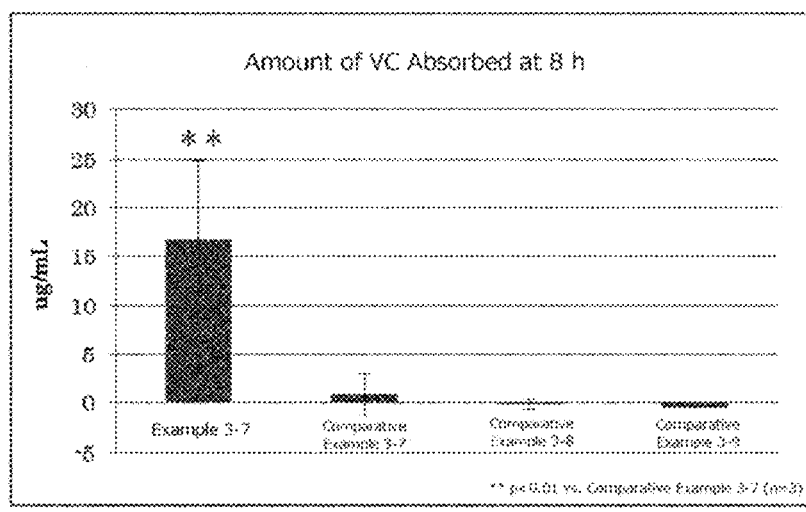
Figures 3, 4, 5, 6, 7, 8:
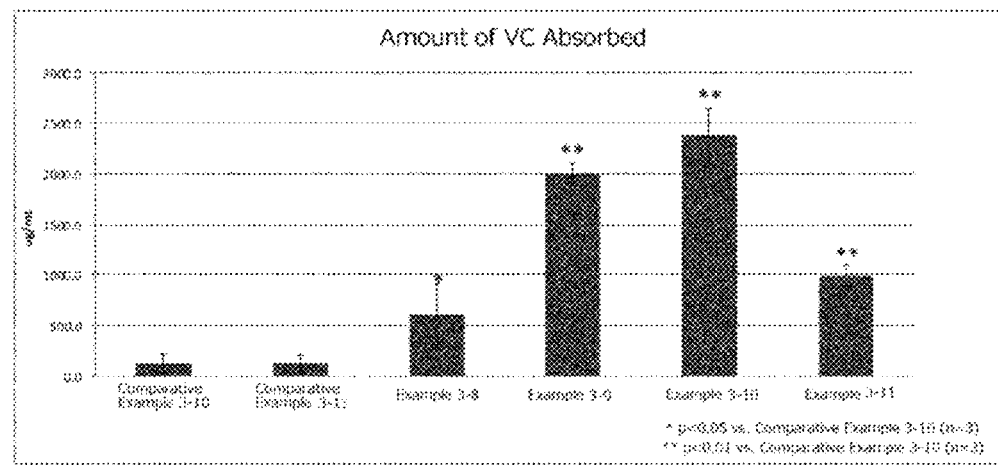
Figures 3, 4, 5, 6, 7, 8, 9:
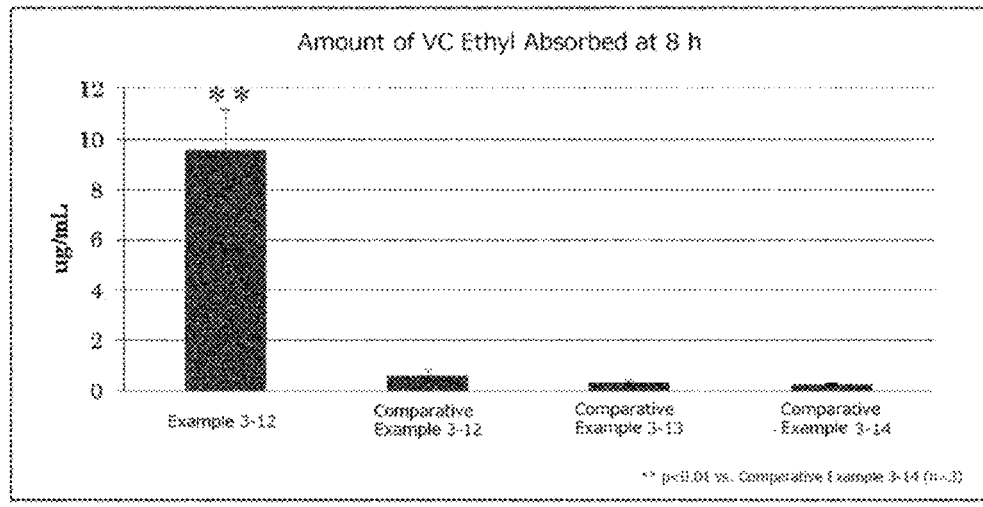
Figures 3, 4, 5, 6, 7, 8, 9, 10:
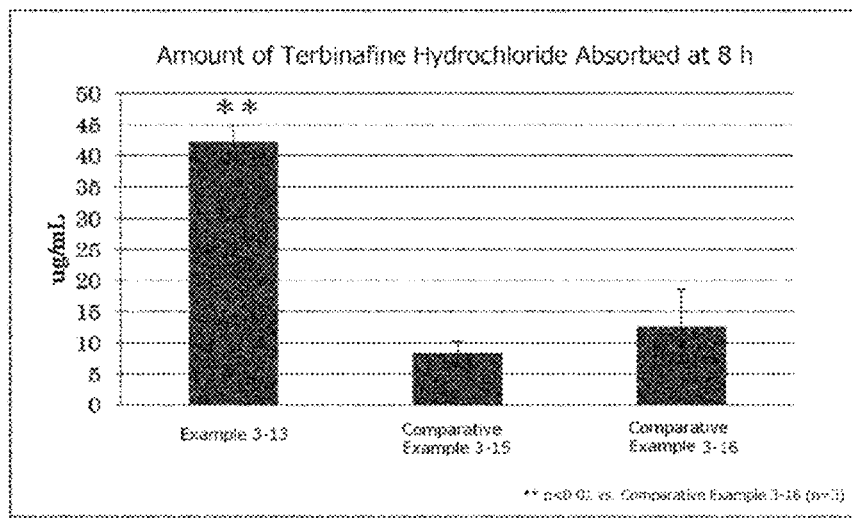
Figures 3, 4, 5, 6, 7, 8, 9, 10, 11:
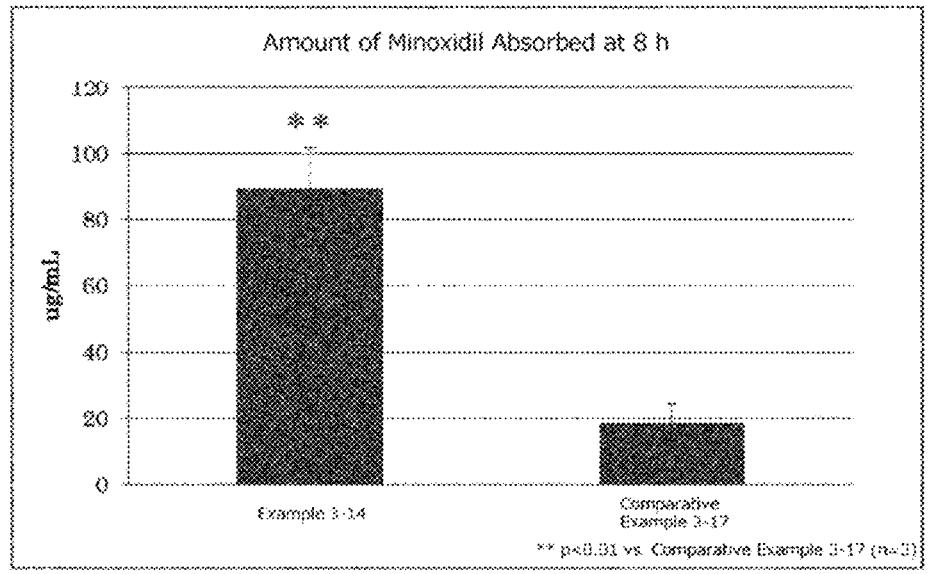
Figures 1, 4:
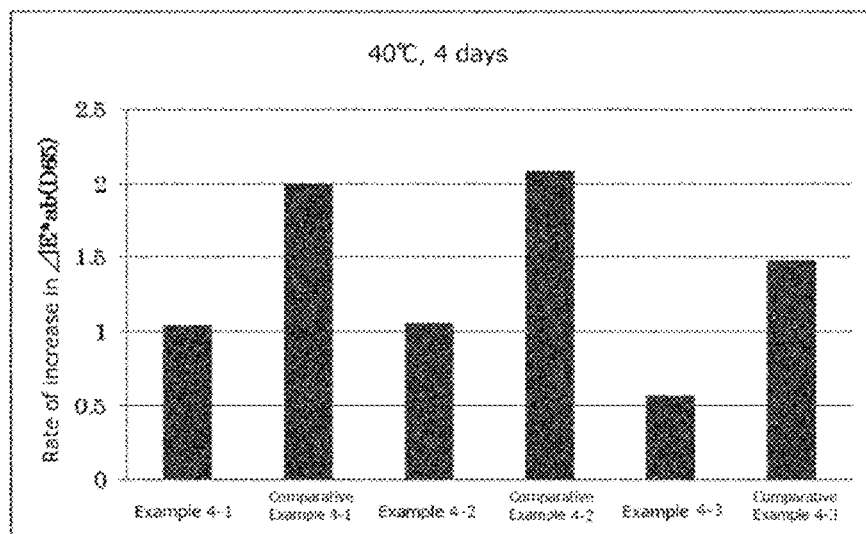
Figures 2, 4:
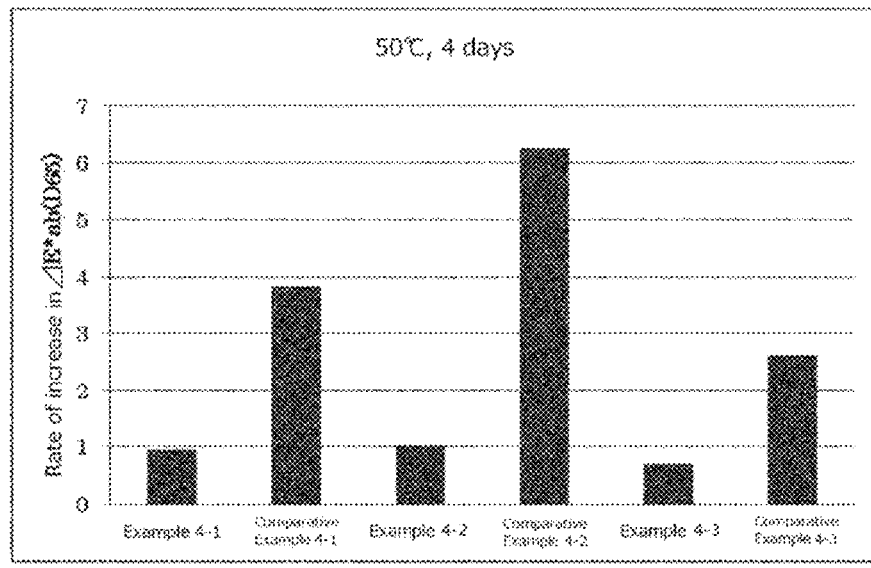
Figures 3, 4:
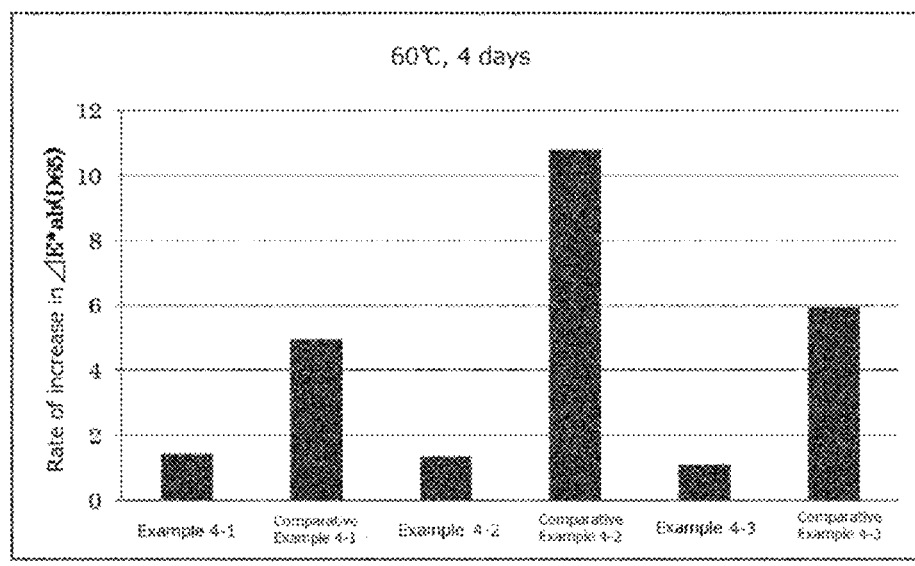
Figure 4:
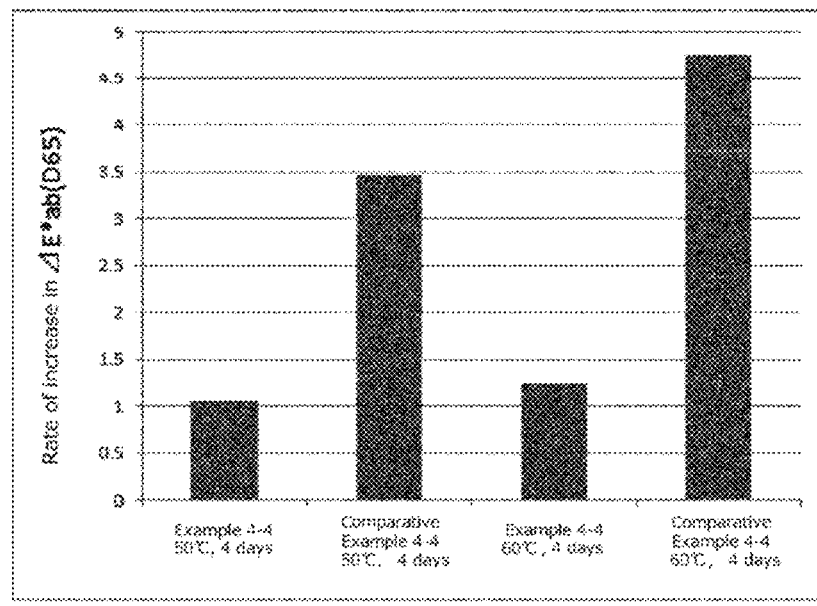
Figures 4, 5:
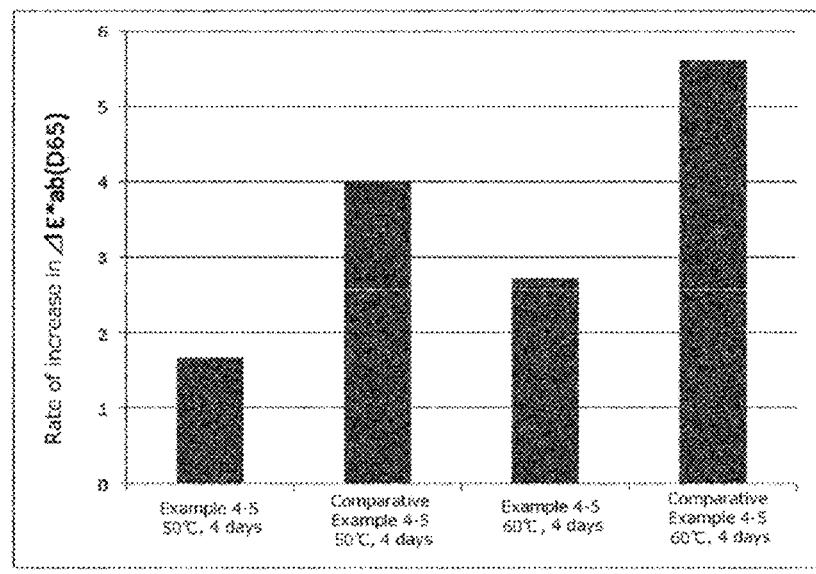
Figures 4, 5, 6:
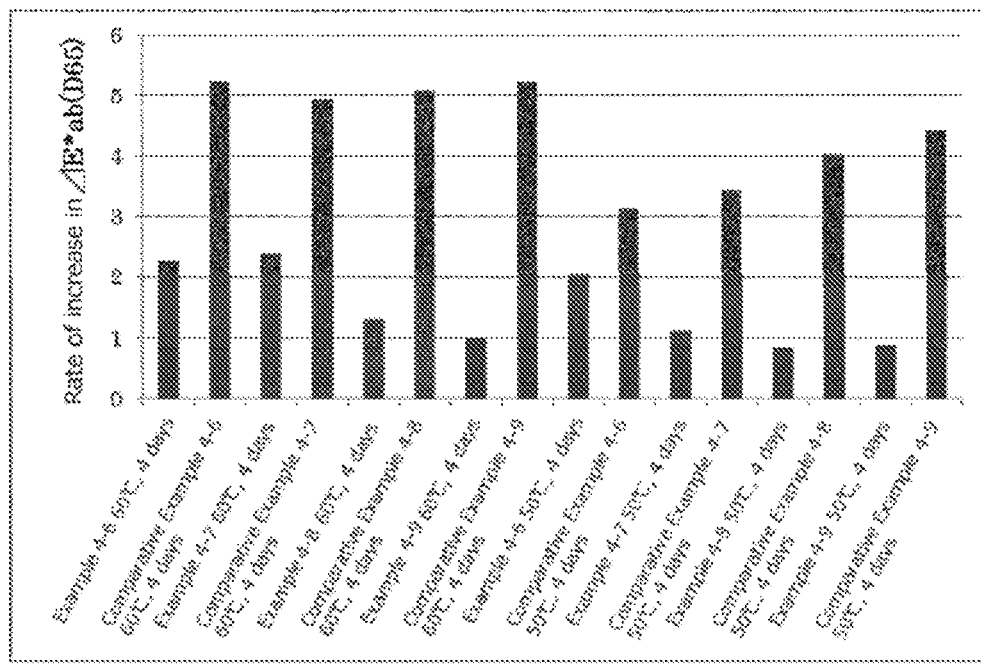
Figures 4, 5, 6, 7:
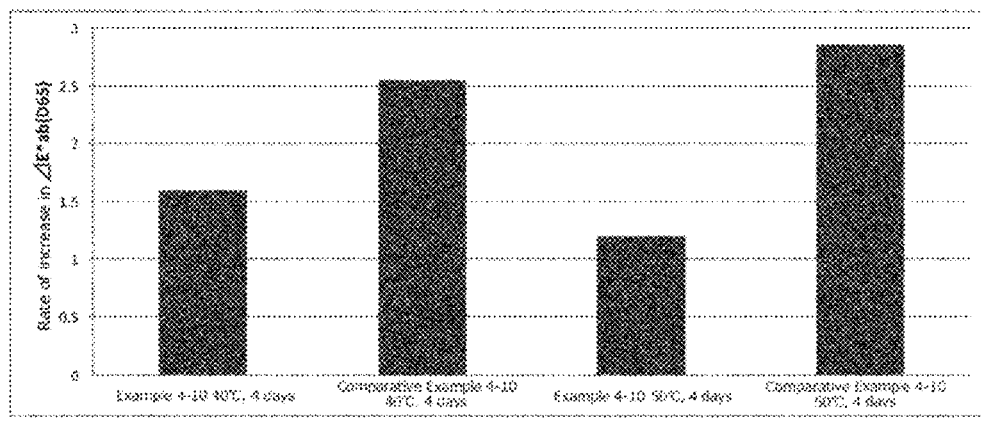
Figures 4, 5, 6, 7, 8:
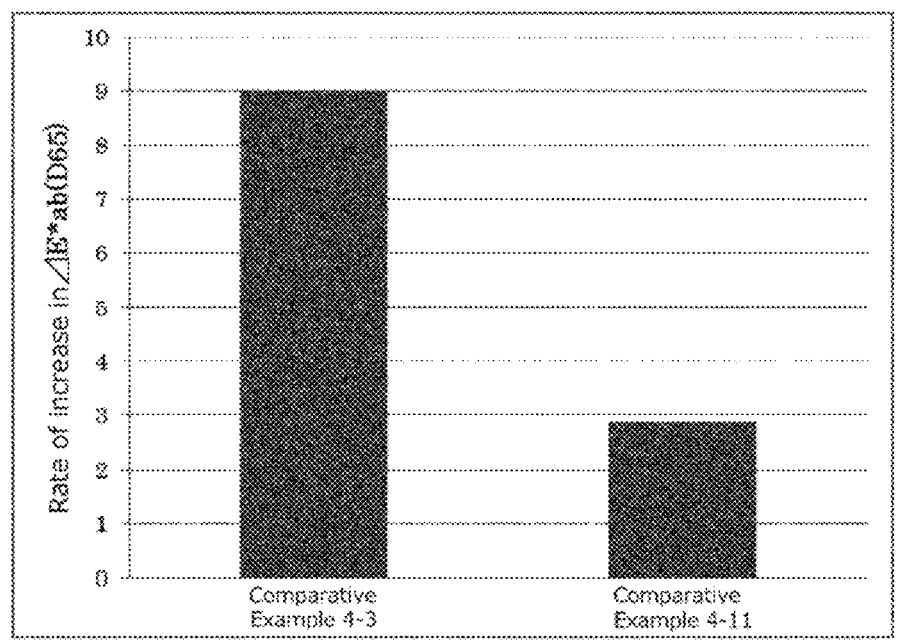

The results are shown in FIG. 4-6. According to FIG. 4-6, compositions of the examples comprising a prescribed lipopeptide and various incorporated concentrations of polyvalent alcohol and/or glycol ether were determined to stably contain a high concentration of vitamin C at 10% by weight without any discoloration in comparison with the compositions of the comparative examples not comprising lipopeptide.

Example 4-10 and Comparative Example 4-10

The compositions described in the following Table 4-7 were prepared in the same manner as in the case of Examples 4-1 to 4-3 and Comparative Examples 4-1 to 4-3.

TABLE 4-7

| | Example 4-10 | Comp. Ex. 4-10 |
|---|---|---|
| Pal-GH | 0.5 | — |
| Ethoxydiglycol | 20 | 20 |
| Hydroquinone | 4 | 4 |
| Water | 20 | 20 |
| BG | 55.5 | 56 |
| Total | 100 | 100 |

The resulting compositions were stored (under protection from light) at 40° C. and 50° C. and then taken out after 4 days followed by determining the rate of increase in ΔE*ab attributable to being stored for 4 days in the same manner as in the case of Examples 4-1 to 4-3 and Comparative Examples 4-1 to 4-3.

The results are shown in FIG. 4-7. According to FIG. 4-7, discoloration was determined to be able to be inhibited by combining a prescribed lipopeptide with a polyvalent alcohol and/or glycol ether even in the case of using hydroquinone for the antioxidant that undergoes discoloration over time. In addition, according to FIG. 4-7, discoloration of hydroquinone was determined to be unable to be inhibited in the composition of the comparative example not comprising lipopeptide.

Comparative Example 4-11

The compositions described in the following Table 4-8 were prepared in the same manner as in the case of Examples 4-1 to 4-3 and Comparative Examples 4-1 to 4-3. Furthermore, the composition of Comparative Example 4-3 was prepared again.

TABLE 4-8

|  | Comp. Ex. 4-3 | Comp. Ex. 4-11 |
|---|---|---|
| Pal-GH | — | — |
| Ethoxydiglycol | 20 | — |
| Ascorbic acid | 3 | — |
| Ascorbyl glucoside | — | 3 |
| Water | 20 | 20 |
| BG | 57 | 73.7 |
| Triethanolamine | — | 3.3 |
| Total | 100 | 100 |

The resulting compositions were stored (under protection from light) at 60° C. and then taken out after 4 days followed by determining the rate of increase in ΔE*ab attributable to being stored for 4 days in the same manner as in the case of Examples 4-1 to 4-3 and Comparative Examples 4-1 to 4-3.

The results are shown in FIG. 4-8. According to FIG. 4-8, since ascorbyl glucoside is not an antioxidant that undergoes discoloration over time, discoloration was determined to not occur even after storing for 4 days at 60° C.

Formulation Examples

The following indicates formulation examples of the skin external use composition of the fourth present invention.

TABLE 4-9

Whitening Essence 1

|  | (%) |
|---|---|
| L-ascorbic acid | 20 |
| Diethylene glycol monoethyl ether | 30 |
| Propylene glycol | 20 |
| Glycerin | 4 |
| Lactic acid | 1.5 |
| Iris root extract | 0.01 |
| Grapefruit extract | 0.5 |
| Glasswort extract | 0.5 |
| Fragrance | 0.1 |
| Pal-GH | 0.5 |
| Purified water | Balance |
| Total | 100 |

TABLE 4-10

Spray Cosmetic

|  | (%) |
|---|---|
| L-ascorbic acid | 8 |
| Ethylene glycol monoethyl ether | 50 |
| Ethanol | 10 |
| Aloe extract | 0.1 |
| Pal-GH | 1 |
| Purified water | Balance |
| Total | 100 |

TABLE 4-11

Whitening Milky Lotion

|  | (%) |
|---|---|
| L-ascorbic acid | 20 |
| Polyglyceryl stearate | 1 |
| Ethylene glycol monoethyl ether | 40 |
| Sodium lactate | 0.1 |
| Stearyl alcohol | 1 |
| Squalane | 1 |
| Lavender oil | 0.5 |
| Chamomile extract | 0.5 |
| Sakhalin kelp extract | 0.5 |
| Pal-GH | 0.5 |
| Purified water | Balance |
| Total | 100 |

TABLE 4-12

External Skin Preparation

|  | (%) |
|---|---|
| L-ascorbic acid | 5 |
| Dipropylene glycol monopropyl ether | 40 |
| Polyoxyethylene sorbitan fatty acid ester | 1 |
| Jojoba oil | 5 |
| Witch hazel extract | 0.1 |
| Carboxyvinyl polymer | 0.5 |
| Triethanolamine | 0.3 |
| Pal-GH | 1 |
| Purified water | Balance |
| Total | 100 |

TABLE 4-13

Whitening Cream

|  | (%) |
|---|---|
| L-ascorbic acid | 20 |
| Ethylene glycol monoethyl ether | 30 |
| Sorbitan stearate | 0.7 |
| PEG sorbitan stearate | 1 |
| Paraffin | 5 |
| Cetanol | 2 |
| Glycerin | 3 |
| 1,3-butylene glycol | 5 |
| Allantoin | 0.1 |
| Xanthan gum | 0.1 |
| Pal-GH | 0.5 |
| Purified water | Balance |
| Total | 100 |

TABLE 4-14

Sunscreen

|  | (%) |
|---|---|
| Arbutin | 3 |
| Trimethylglycine | 1 |
| 2-ethylhexyl para-methoxycinnamate | 10 |
| Decamethylcyclopentasiloxane | 20 |
| Octyl palmitate | 10 |
| Polyoxyethylene-methylpolysiloxane copolymer | 3 |
| Methyl hydrogenpolysiloxane-treated low temperature-fired zinc oxide | 15 |
| Alkyl polyacrylate | 5 |
| Concentrated glycerin | 5 |
| Absolute ethanol | 5 |
| 1,3-butylene glycol | 3 |
| Panthenol | 0.1 |
| Fragrance | 0.1 |
| Phytic acid | 0.05 |
| Pal-GH | 0.5 |
| Purified water | Balance |
| Total | 100 |

TABLE 4-15

Whitening Cream

|  | (%) |
|---|---|
| Arbutin | 3 |
| Trimethylglycine | 2 |
| Lauryl dimethicone polyglycerin-3 crosspolymer-glyceryl tri(2-ethylhexanoate) | 5 |
| Crosslinked methylpolysiloxane-methylpolysiloxane | 5 |
| Crosslinked alkyl-modified silicon-glyceryl tri(2-ethylhexanoate) | 3 |
| Decamethylcyclopentasiloxane | 15 |
| Polymethylsilsesquioxane | 3 |
| (Dimethicone-vinyl dimethicone-methicone) crosspolymer | 1 |
| Alkyl polyacrylate | 5 |
| Concentrated glycerin | 10 |
| Magnesium sulfate | 0.1 |
| Sodium edetate | 0.05 |
| Cyanocobalamin | 0.01 |
| Methyl paraoxybenzoate 0.05 | 0.2 |
| Pal-GH | 0.5 |
| Purified water | Balance |
| Total | 100 |

TABLE 4-16

Whitening Milky Lotion

|  | (%) |
|---|---|
| Arbutin | 3 |
| Trimethylglycine | 2 |
| Polyglyceryl-10 isostearate | 2 |
| Polyoxyethylene hydrogenated castor oil (HCO-10) | 0.5 |
| Squalane | 5 |
| Carboxyvinyl polymer | 0.2 |
| Triethanolamine | 0.1 |
| Concentrated glycerin | 5 |
| Magnesium sulfate | 0.1 |
| Sodium edetate | 0.05 |
| Methyl paraoxybenzoate | 0.2 |
| Pal-GH | 0.5 |
| Purified water | Balance |
| Total | 100 |

TABLE 4-17

Whitening Essence

|  | (%) |
|---|---|
| Hydroquinone | 1 |
| Diethylene glycol monoethyl ether | 30 |
| Hyaluronic acid | 0.05 |
| 1,3-butylene glycol | 50 |
| Methyl paraoxybenzoate | 0.05 |
| Pal-GH | 0.5 |
| Purified water | Balance |
| Total | 100 |

TABLE 4-18

Aging Care Cream

|  | (%) |
|---|---|
| Astaxanthin | 0.1 |
| Trimethylglycine | 0.1 |
| Pentaerythritol tetra(2-ethylhexanoate) | 5 |
| White Vaseline | 2 |
| Polyoxyethylene sorbitan stearate | 2 |
| Carboxyvinyl polymer | 0.1 |
| 1,3-butylene glycol | 5 |
| Cetanol | 0.5 |
| Concentrated glycerin | 5 |
| Cyanocobalamin | 0.01 |
| L-arginine | 0.1 |
| Xanthan gum | 0.1 |
| Hydroxyethyl cellulose | 0.1 |
| Sodium alginate | 0.1 |
| Methyl paraoxybenzoate | 0.2 |
| Propyl paraoxybenzoate | 0.05 |
| Pal-GH | 1 |
| Purified water | Balance |
| Total | 100 |

TABLE 4-19

Aging Care Essence

|  | (%) |
|---|---|
| Astaxanthin | 0.5 |
| Trimethylglycine | 3 |
| Sodium ascorbate | 10 |
| Hyaluronic acid | 0.05 |
| 1,3-butylene glycol | 5 |
| Polyoxyethylene hydrogenated castor oil 80 | 1 |
| Methyl paraoxybenzoate | 0.05 |
| Pal-GH | 0.5 |
| Purified water | Balance |
| Total | 100 |

The invention claimed is:

1. A method for anti-aging, comprising the use of: (A) a lipopeptide represented by the following formula (1) or a pharmaceutically acceptable salt thereof:

111

Chemical 24

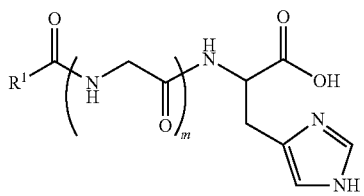

(1)

(wherein, $R^1$ represents a saturated aliphatic group, or aliphatic group having a single unsaturated bond, having 9 to 19 carbon atoms, and m represents 1).

2. The method according to claim 1, further comprising the use of vitamin C.

3. The method according to claim 1, which is for suppressing, improving or preventing wrinkling, or sagging of the skin, or decreases in skin resiliency and elasticity.

4. The method according to claim 1, which is for promoting collagen production.

5. A method for antibacterial, comprising: the use of (A2) a compound represented by the following formula (2-1) or a pharmaceutically acceptable salt thereof:

Chemical 26

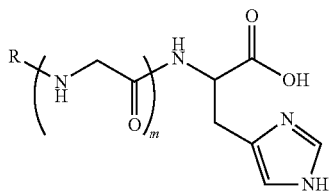

(2-1)

(wherein, R represents a hydrogen atom or a group represented by C(O)$R^1$, $R^1$ represents a saturated aliphatic group, or aliphatic group having a single unsaturated bond, having 9 to 19 carbon atoms, and m represents 1).

6. The method according to claim 5, which is for antibacterial against *Propionibacterium acnes*.

7. An external use composition, comprising:
(A) a lipopeptide represented by the following formula (i) and/or a pharmaceutically acceptable salt thereof,
(B) a polyvalent alcohol and/or a glycol ether, and
an antioxidant selected from the group consisting of vitamin C, hydroquinone, arbutin, astaxanthin, dibutylhydroxytoluene, and coenzyme Q1;
wherein the content of the Component (A) in the external use composition is 0.05% by weight or more:

[Chemical 30]

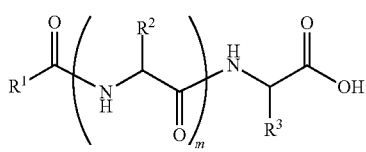

(i)

(wherein, $R^1$ represents an aliphatic group having 9 to 23 carbon atoms, $R^2$ and $R^3$ respectively and independently

112 represent a hydrogen atom, methyl group, ethyl group, alkyl group having 3 to 7 carbon atoms that may have a branched chain having 1 to 3 carbon atoms, phenylmethyl group, phenylethyl group or —(CH$_2$)$_n$—X group and at least one of $R^2$ or $R^3$ represents a (CH$_2$)$_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ may be the same or different in the case m is 2 or more).

8. The external use composition according to claim 7, further comprising an active ingredient (C) which is at least one type selected from the group consisting of a disinfectant component, anti-inflammatory component, anti-inflammatory analgesic component, antipruritic component, vitamins, local anesthetic component, moisturizing component, whitening component, antioxidant component, anti-aging component, keratin softening component, cell activating component, circulation promoting component, component having action that prevents and/or repairs damaged DNA, ultraviolet absorbing component, ultraviolet scattering component, astringent component, hair growth component, antihistamine component and antiseptic component.

9. The external use composition according to claim 7, wherein $R^2$ in the formula (i) represents a hydrogen atom, a methyl group, i-propyl group, i-butyl group or sec-butyl group.

10. The external use composition according to claim 7, further comprising terpenes (D).

11. The external use composition according to claim 7, wherein the content of the Component (B) in the external use composition is 0.0001% to 75% by weight.

12. The external use composition according to claim 7, wherein $R^1$ in the formula (i) represents an aliphatic group having 13 to 17 carbon atoms, $R^2$ represents a hydrogen atom, methyl group or i-propyl group, and $R^3$ represents a 4-aminobutyl group, 4-imidazolemethyl group or 3-methylindole group.

13. An external use skin composition comprising a lipopeptide represented by the following formula (i), and/or a pharmaceutically acceptable salt thereof, a polyvalent alcohol and/or glycol ether, and an antioxidant that undergoes discoloration over time, wherein the antioxidant that undergoes discoloration over time is at least one type selected from the group consisting of vitamin C, hydroquinone, arbutin, astaxanthin, dibutylhydroxytoluene and coenzyme Q10:

[Chemical 35]

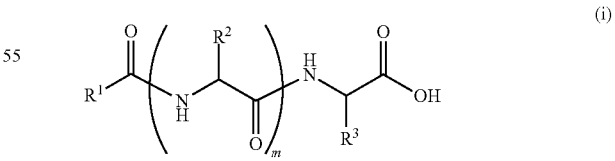

(i)

(wherein, $R^1$ represents an aliphatic group having 9 to 23 carbon atoms, $R^2$ and $R^3$ respectively and independently represent a hydrogen atom, methyl group, ethyl group, alkyl group having 3 to 7 carbon atoms that may have a branched chain having 1 to 3 carbon atoms, phenylmethyl group, phenylethyl group or —(CH$_2$)$_n$—X group and at least one of $R^2$ or $R^3$ represents a —$(CH_2)_n$—X group, n represents an integer of 1 to 4, X represents an amino group, guanidino group, carbamoyl group, 5-membered cyclic group or 6-membered cyclic group that may have 1 to 3 nitrogen atoms or condensed cyclic group composed of a 5-membered ring and 6-membered ring, m represents an integer of 1 to 3, and a plurality of $R^2$ present may be the same or different in the case m is 2 or more).

14. The external use skin composition according to claim 13, wherein $R^2$ in the formula (i) represents a hydrogen atom, methyl group, i-propyl group, i-butyl group or sec-butyl group.

15. The external use skin composition according to claim 13, wherein $R^1$ in the formula (i) represents an aliphatic group having 13 to 17 carbon atoms, $R^2$ represents a hydrogen atom, methyl group or i-propyl group, and $R^3$ represents a 4-aminobutyl group, 4-imidazolemethyl group or 3-methylindole group.

16. The external use skin composition according to claim 13, wherein the content of the antioxidant that undergoes discoloration over time in the external use skin composition is 3% to 30% by weight.

17. The external use skin composition according to claim 13, wherein the content of the polyvalent alcohol and/or glycol ether in the external use skin composition is 5% to 90% by weight.

18. The external use skin composition according to claim 13, wherein the polyvalent alcohol and/or glycol ether is at least one type selected from the group consisting of ethoxydiglycol, 1,3-butylene glycol, dipropylene glycol, propylene glycol and glycerin.

* * * * *